US005358946A

United States Patent [19]

Wilde

[11] Patent Number: 5,358,946
[45] Date of Patent: Oct. 25, 1994

[54] HETEROCYCLE-SUBSTITUTED AMIDES, CARBAMATES AND UREAS AS AGENTS FOR THE TREATMENT OF ATHEROSCLEROSIS

[75] Inventor: Richard G. Wilde, New Castle, Del.

[73] Assignee: The Du Pont Merck Pharmaceutical Company, Wilmington, Del.

[21] Appl. No.: 889,896

[22] Filed: May 29, 1992

[51] Int. Cl.$^5$ ............... A61K 31/535; A61K 31/415; C07D 413/02; C07D 265/28; C07D 233/66; C07D 233/00

[52] U.S. Cl. ................... 514/235.8; 514/255; 514/326; 514/394; 514/397; 514/398; 514/399; 514/400; 544/139; 544/370; 546/210; 548/314.7; 548/320.1; 548/320.5; 548/319.1; 548/324.1; 540/603

[58] Field of Search ............ 548/337, 316.4, 319.1, 548/320.5, 324.1, 320.1, 314.7, 331.5; 544/139, 370; 514/235.8, 398, 394, 400, 397, 255, 32 C, 394; 540/210, 603

[56] References Cited

U.S. PATENT DOCUMENTS

| | | | |
|---|---|---|---|
| 3,950,353 | 4/1976 | Durant et al. | 548/331.5 X |
| 4,228,291 | 10/1980 | Durant et al. | 548/138 |
| 4,413,130 | 11/1983 | White | 548/324.1 X |
| 5,025,015 | 6/1991 | Patoiseau et al. | 548/324.1 X |
| 5,179,117 | 1/1993 | Maduskie | 548/324.1 X |

FOREIGN PATENT DOCUMENTS

| | | |
|---|---|---|
| 0372445 | 6/1990 | European Pat. Off. |
| 9113876 | 9/1991 | PCT Int'l Appl. |
| 91-18885 | 12/1991 | World Int. Prop. O. ....... 548/335.1 |

OTHER PUBLICATIONS

Haust, M. D., Reaction Patterns of Intimal Mesenchyme To Injury, and Repair in Atherosclerosis, *Adv. Exp. Med. Biol*, 43, pp. 35–57 (1974).

Pike et al., Nutrition An Integrated Approach, 3rd Edition, John Wiley and Sons, Inc., New York, pp. 531–535 (1984).

Clarkson et al., Differences in Atherosclerotic Development, *Annals of the New York Academy of Sciences*, vol. 454, pp. 28–43 (1985).

*Primary Examiner*—Floyd D. Higel
*Attorney, Agent, or Firm*—Raymond G. Arner

[57] ABSTRACT

This invention relates to imidazoles, namely, heterocycle-substituted amides, carbamates and ureas as inhibitors of acyl-CoA: cholesterol acyltransferase (ACAT), pharmaceutical compositions containing them, and their use as antihypercholesterolemic and/or antiatherosclerotic agents for the treatment of atherosclerosis.

12 Claims, No Drawings

HETEROCYCLE-SUBSTITUTED AMIDES, CARBAMATES AND UREAS AS AGENTS FOR THE TREATMENT OF ATHEROSCLEROSIS

FIELD OF THE INVENTION

This invention relates to imidazoles as inhibitors of acyl-CoA: cholesterol acyltransferase (ACAT), pharmaceutical compositions containing them, processes for their preparation, and their use as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There are an increasing number of patents in the literature disclosing compounds which are useful as ACAT inhibitors in particular and antiatherosclerotic agents in general. For example, U.S. Pat. No. 4,623,662, issued to DeVries on November 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol. U.S. Pat. No. 4,824,843, issued to Hoefle, et al. on Apr. 25, 1989, and the related U.S. Pat. No. 4,882,357, issued to Creger et al. on Nov. 21, 1989, disclose a series of substituted N-phenyl-2,2-dimethyl-5-aryloxypentanamides, which prevent the intestinal absorption of cholesterol in mammals by inhibiting ACAT. European Patent Application 325,397, filed by Ito on Jul. 26, 1989, discloses a series of compounds consisting of two N-cycloalkyl-N'-arylurea units linked at nitrogen by a dialkylphenyl unit, which are inhibitors of the ACAT enzyme. U.S. Pat. No. 4,868,210, issued to Trivedi on Sep. 19 1989, and the related European Patent Applications 335,374 filed by Trivedi on Mar. 30, 1988, and 386,487, filed by Trivedi on Feb. 9, 1989, disclose certain N-2,6-dialkyl- or N-2,6-dialkoxyphenyl-N'arylalkyl ureas as potent inhibitors of ACAT. European Patent Application 354,994, filed by Meguro and Ikeda on Feb. 21, 1990, discloses certain N-aryl-N'-quinolin-4-yl ureas as ACAT inhibitors. European Patent Application 370,740, filed by Jackson et al. on Nov. 21, 1988, discloses ACAT inhibitors similar in composition to those of deVries (vide supra) but different in constitution. European Patent Application EP-A-372,445, filed by Billheimer et al. on Dec. 3, 1989, discloses compounds of formulae

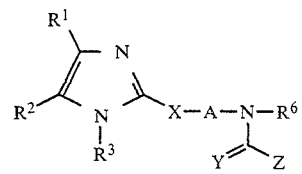

wherein $R^1$ and $R^2$ are selected independently from H, $C_1$–$C_8$ alkyl, $C_3$–$C_8$ branched alkyl, $C_3$–$C_7$ cycloalkyl, $C_4$–$C_{10}$ cycloalkylalkyl, $C_7$–$C_{14}$ araalkyl, 2-, 3- or 4-pyridinyl, 2-thienyl, 2-furanyl, phenyl optionally substituted with 1 to 3 groups selected from F, Cl, Br, OH, $C_1$–$C_4$ alkoxy, $C_1$–$C_4$ alkyl, $C_3$–$C_8$ branched alkyl, $CH_3S(O)_r$, $NO_2$, $CF_3$, or $NR^7R^8$; or $R^1$ and $R^2$ can also be taken together as

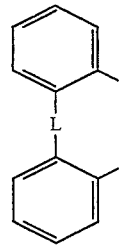

where L is O, $O(CH_2)_{m+1}O$, or $(CH_2)_m$ where m is 0–4;

$R^3$ is H, $C_1$–$C_6$ alkyl, allyl, benzyl, or phenyl optionally substituted with F, Cl, $CH_3$, $CH_3O$, or $CF_3$;

$R^4$ is straight chain $C_1$–$C_8$ alkyl optionally substituted with F; $C_3$–$C_8$ branched alkyl, $C_3$–$C_7$ cycloalkyl, $C_4$–$C_{10}$ cycloalkylalkyl, $C_7$–$C_{14}$ araalkyl where the aryl group is optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$ or $NCOR^7$; $C_3$–$C_6$ alkenyl or alkynyl, $C_1$–$C_3$ perfluoroalkyl, phenyl optionally substituted with 1 to 3 groups selected from $C_1$–$C_4$ alkyl, $C_3$–$C_8$ branched alkyl, $C_1$–$C_4$ alkoxy, F, Br, Cl, $NH_2$, OH, CN, $CO_2H$, $CF_3$, $NO_2$, $C_1$–$C_4$ carboalkoxy, $NR^7R^8$ or $NCOR^7$; pentafluorophenyl, benzyl optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$, or $NCOR^7$; 2-, 3- or 4-pyridinyl, pyrimidinyl, or biphenyl;

$R^5$ is H, $C_1$–$C_6$ alkyl, or benzyl;

$R^6$ is $C_1$–$C_8$ alkyl, $C_3$–$C_8$ branched alkyl, $C_3$–$C_7$ cycloalkyl, $C_3$–$C_8$ alkenyl or alkynyl, phenyl optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$ or $NCOR^7$; pentafluorophenyl, benzyl optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$, or $NCOR^7$;

$R^7$ and $R^8$ are selected independently from H or $C_1$–$C_4$ alkyl;

X is S(O) r, O, $NR^5$ $CH_2$;

A is $C_2$–$C_{10}$ alkyl, $C_3$–$C_{10}$ branched alkyl, $C_3$–$C_{10}$ alkenyl, or $C_3$–$C_{10}$ alkynyl;

Y is O, S, $H_2$, NH;

Z is $NHR^4$, $OR^4$ or $R^4$;

r is 0–2, or a pharmaceutically acceptable salt thereof.

These compounds are potent in vitro inhibitors of ACAT and are therefore potential antihypercholesterolemic agents.

U.S. Pat. No. 4,460,598, issued to Lautenschläger et al. on Jul. 17, 1984, discloses compounds of the formula:

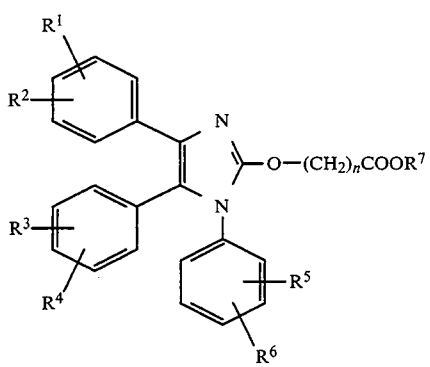

wherein $R^1$, $R^2$, $R^3$, $R^4$, $R^5$ and $R^6$ independently are H, F, Cl, Br, I, alkyl, alkoxy, or $CF_3$, with the proviso that one or several of $R^1$ and $R^2$, $R^3$ and $R^4$, or $R^5$ and $R^6$ taken together represent methylenedioxy;

$R^7$ is H, alkali metal ion, alkyl of 1 to 6 carbon atoms, or benzyl; and n is 0 to 10.

The synthesis and the use of these compounds in the treatment of thromboembolic, inflammatory and/or atherosclerotic diseases is disclosed. U.S. Pat. No. 4,900,744, issued to Billheimer, et al. on Feb. 13, 1990, discloses antihypercholesterolemic thioimidazoles of the formula

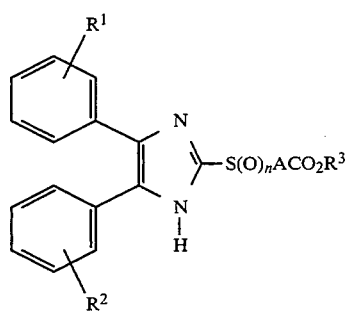

or a pharmaceutically acceptable salt thereof, wherein $R^1$ and $R^2$ independently are H, F, Cl, $CF_3$, alkyl of 1 to 4 carbon atoms, or alkoxy of 1 to 4 carbon atoms;

A is alkylene of 7–20 carbon atoms or an alkenyl residue thereof with no more than 2 double bonds;

$R^3$ is H, $CH_3$ OR $C_2H_5$; and n is 0, 1 or 2, such as 8-(4,5-diphenyl-1H-imidazol-2-ylthio)octanoic acid ethyl ester.

U.S. Pat. No. 4,654,358, issued to Lautenschläger et al. on Mar. 31, 1987, discloses compounds of the formula:

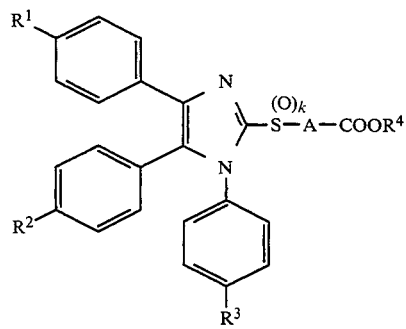

wherein k is 0, 1, or 2, $R^1$, $R^2$ and $R^3$ independently are H, F, Cl, $CH_3$, $CH_3O$, or $CF_3$;

$R^4$ is H, Na, K, $CH_3$, $CH_3CH_2$, $(CH_3)_2CH$, $CH_3(CH_2)_2$, or butyl;

A is $C(CH_3)_2$, $CH(CH_2)_mCH_3$, $(CH_2)_n$, or $(CH_2)_{n-2}CH(CH_3)$;

m is 0 to 8; and n is 2 to 10.

The synthesis and the use of these compounds in the treatment of inflammatory diseases, diseases of lipid metabolism, and/or hyperlipidemic diseases is disclosed.

German Laid Open Application No. DE 3504679, Lautenschläger et al., published Aug. 14, 1986, discloses compounds of the formula:

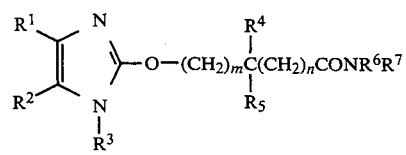

wherein $R^1$ $R^2$ and $R^3$ independently are H, alkyl of 1 to 6 carbon atoms, cycloalkyl of 1 to 6 carbon atoms, or

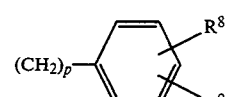

$R^4$ and $R^5$ independently are H, $C_6H_5$, or alkyl of 1 to 9 carbon atoms;

$R^6$ and $R^7$ independently are H, OH, saturated or unsaturated alkyl, cycloalkyl, or hydroxyalkyl of 1 to 10 carbon atoms,

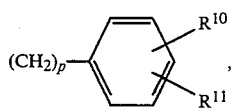

-continued

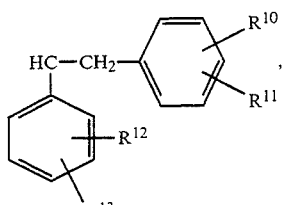

or

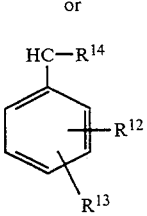

$R^8$, $R^9$, $R^{10}$, $R^{11}$, $R^{12}$ and $R^{13}$ independently are H, F, Cl, Br, $NO_2$, $CH_3CONH$, OH, alkyl of 1 to 3 carbon atoms, $CF_3$, and alkoxy of 1 to 3 carbon atoms, with the proviso that $R^8$ and $R^9$, $R^{10}$ and $R^{11}$, or $R^{12}$ and $R^{13}$ taken together represent methylenedioxy;

$R^{14}$ is alkyl of 1 to 2 carbon atoms;

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

German Laid Open Application No. DE 3504680, Lautenschläger et al., published Aug. 14, 1986, discloses compounds of the formula:

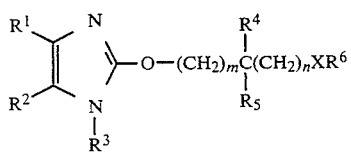

wherein $R^1$, $R^2$ and $R^3$ independently are H, alkyl of 1 to 6 carbon atoms, cycloalkyl of 1 to 6 carbon atoms, or

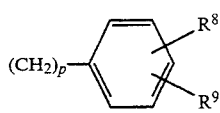

$R^1$ and $R^2$ can be taken together with the carbon atoms in the 4 and 5 position of the imidazole ring to represent a carbocyclic five- or six-membered aromatic or partially hydrogenated ring which may be substituted by $R^8$ or $R^9$;

$R^4$ and $R^5$ independently are H, $C_6H_5$, or alkyl of 1 to 9 carbon atoms;

$R^6$ is alkyl, cycloalkyl, or hydroxyalkyl of 1 to 20 carbon atoms, H, alkali metal if X is —COO—, 1-phenethyl, or

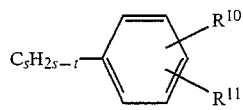

$R^7$ is H, OH if X is —$CONR^7$—, or alkyl of 1 to 4 carbon atoms;

$R^8$, $R^9$, $R^{10}$ and $R^{11}$ are independently H, Cl, F, Br, $NO_2$, $CH_3CONH$, OH, alkyl of 1 to 3 carbon atoms, $CF_3$, or alkoxy of 1 to 3 carbons, or $R^8$ and $R^9$ or $R^{10}$ and $R^{11}$ taken together represent methylenedioxy;

X is a bond, O, OC(=O)O, C(=O)O, $CONR^7$, OC(=O), or OC(=O)$NR^7$;

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

Durant et al., U.S. Pat. No. 4,228,291, issued Oct. 14, 1980, teaches compounds of the formula:

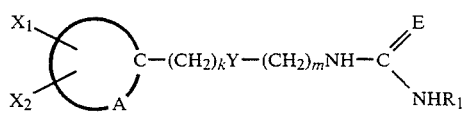

wherein A together with the carbon atom form an unsaturated heterocyclic nucleus which may be an imidazole, pyrazole, pyrimidine, pyrazine, pyridazine, thiazole, isothiazole, oxazole, isoxazole, triazole, thiadiazole, benzimidazole, or 5, 6, 7,8-tetrahydroimidazol[1,5-a]pyridine ring; $X_1$ is H, lower alkyl, hydroxyl, trifluoromethyl, benzyl, halogen, amino, or

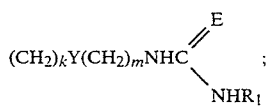

$X_2$ is H, or when $X_1$ is lower alkyl, lower alkyl or halogen; k is 0 to 2 and m is 2 or 3, provided that the sum of k and m is 3 or 4; Y is O, S, or NH; E is $NR^2$; $R^1$ is H, lower alkyl or di-lower alkyl amino-lower alkyl; and $R^2$ is H, nitro, or cyano. The compounds are said to be antihistamines of the H2 receptor blocking type, as well as having anti-inflammatory activity.

White, U.S. Pat. No. 4,413,130, Nov. 1, 1983, discloses histamine $H_2$ receptor antagonists of the formula:

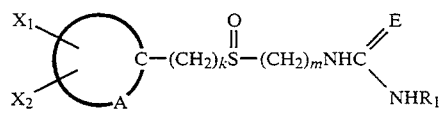

where A together with the carbon atom form an unsaturated heterocyclic nucleus which may be an imidazole, pyridine, thiazole, isothiazole, oxazole, isoxazole, pyrazole, triazole, thiadiazole, pyrimidine, pyrazine or pyridazine; $X_1$ and $X_2$ may be H, lower alkyl, trifluoromethyl, hydroxyl, halogen, amino, or $X_1$ and $X_2$ and at least two of the atoms comprising A may form a further ring; k is 0 to 2 and m is 2 or 3, provided that the sum of k and m is 3 or 4; E is 0, S, or $NR^2$; $R^1$ is H, lower alkyl, acyl, or dialkylamino-alkyl; and $R^2$ is H, $NO_2$, CN, alkansulphonyl or arenesulphonyl.

There are no known literature references disclosing the imidazoles of this invention, their use as ACAT inhibitors, or their use to lower cholesterol or in the treatment of atherosclerosis.

SUMMARY OF THE INVENTION

The present invention provides novel compounds of Formula (I), processes for their preparation, pharmaceutical compositions containing such heterocyclic compounds, and therapeutic methods for their use as antihypercholesterolemic and/or antiatherosclerotic agents.

This invention provides compounds of Formula (I):

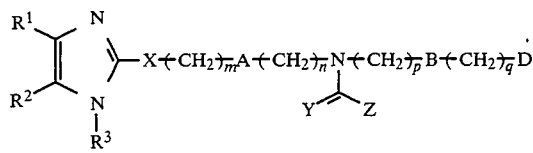

wherein
A and B are selected independently from the groups —$CH_2$—, O, $NR^6$, $S(O)_r$, —C(=O)O—, —C(=O)N($R^6$)—, —OC(=O)=, and —N($R^6$)C(=O)—;
D is selected from the groups
—$(CH_2)_tH$, —$O(CH_2)_tH$, —$NR^7R^8$, and

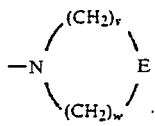

wherein
t is 0–4, E is $CH_2$, $O, NR^7$, C=O, —C(=O)$NR^7$—, or —C(=O)O—, and v and w are independently 0–4, with the proviso that v and w cannot both be 0;
X is $S(O)_r$, $CH_2$, or $NR^5$, where r is 0–2;
Y is O, S, $H_2$ or $NR^5$;
Z is $NHR^4$, $OR^4$ or $R^4$;
$R^1$ and $R^2$ are selected independently from H, $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ aralkyl, 2-, 3- or 4-pyridinyl, 2-thienyl, 2-furanyl, phenyl (optionally substituted with 1 to 3 groups selected from F, Cl, Br, OH, $C_1$-$C_4$ alkoxy, $C_1$-$C_4$ alkyl, $C_3$-$C_8$ branched alkyl, $CH_3S(O)_r$, $NO_2$, $CF_3$, or $NR^7R^8$);
$R^3$ is H, $CH_3$ or phenyl;
$R^4$ is $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ aralkyl, phenyl (optionally substituted with 1 to 3 groups selected from $C_1$-$C_4$ alkyl, $C_3$-$C_8$ branched alkyl, F, Cl, $C_1$-$C_4$ alkoxy, or CN), benzyl (optionally substituted with 1 to 3 groups selected from $CH_3$, $CH_3O$, F, Cl, or CN), pyridyl, pyrrolyl, pyrimidyl, or imidazolyl;
$R^5$ is H, $CH_3$, or phenyl;
$R^6R^7$ and $R^8$ are selected independently from H or $C_1$-$C_4$ alkyl;
m, n, p and q are independently 0–4;

with the proviso that when A is $CH_2$ and B is $CH_2$, then D cannot be $CH_2$.

Preferred are compounds of Formula (I) wherein
A is selected from the groups $CH_2$, O, $NR^6$, —C(=O)O—, and —C(=O)$R^6$;
B is selected from the groups $CH_2$, O, $NR^6$ or $S(O)_r$;
X is S $(O)_r$ or $CH_2$;
Y is O or $H_2$;
$R^1$ and $R^2$ are selected independently from H, $C_1$-$C_8$ alkyl, $C_3$-$C_8$ branched alkyl, $C_3$-$C_7$ cycloalkyl, phenyl (optionally substituted with 1–3 groups selected from $C_1$-$C_4$ alkoxy, $C_1$-$C_4$ alkyl, $C_3$-$C_8$ branched alkyl, $CH_3S(O)r$, F, or $NR^7R^8$), pyridyl, thienyl, or furanyl.

More preferred are compounds of Formula (I) wherein:
A and B are selected independently from the groups —$CH_2$—, O, and $NR^6$;
D is selected from the groups —$(CH_2)_tH$, —$O(CH_2)_tH$, —$NR^7R^8$, and

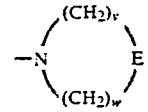

wherein t is 0–4, E is $CH_2$, O or $NR^7$ and v and w are independently 2–4;
X is $S(O)_r$;
Y is O;
$R^1$ and $R^2$ are selected independently from H, $C_1$-$C_8$ alkyl, $C_3$-$C_8$ branched alkyl, $C_3$-$C_7$ cycloalkyl, and phenyl (optionally substituted with 1 to 3 groups selected from $C_1$-$C_4$ alkoxy, $C_1$-$C_4$ alkyl, $C_3$-$C_8$ branched alkyl, $CH_3S(O)_r$, or $NR^7R^8$);
$R^3$ is H.

Specifically preferred because of their biological activity are compounds of Formula (I) wherein:
$R^1$ and $R^2$ are selected independently from H or phenyl (optionally substituted with 1 to 3 groups selected from $CH_3O$, $CH_3S(O)_r$ or $(CH_3)_2N$);
$R^4$ is $C_1$-$C_8$ alkyl, $C_3$-$C_8$ branched alkyl, or phenyl (optionally substituted with 1 to 3 groups selected from $CH_3$, $CH(CH_3)_2$, F, $CH_3O$, or CN);
Z is $NHR^4$ or $R^4$;
m, n and p are 2.

Specific compounds of interest are:
N-[2-(diethylamino)ethyl]-N-[5-(4,5-diphenyl-1H-imidazol-2-ylthio)pentyl]-N'-(1-methylethyl)-urea
N-[2-[2-[4,5-bis(4-methoxyphenyl)-1H-imidazol-2-ylthio]ethoxy]ethyl]-N-heptyl-N'-(1-methylethyl)-urea
N-(2-butoxyethyl)-N-[5-(4,5-diphenyl-1H-imidazol-2-ylthio)pentyl]-N'-(1-methylethyl)-urea
N-[5-[4,5-bis(4-methoxyphenyl)-1H-imidazol-2-ylthio]pentyl]-N '-(2,4-difluorophenyl)-N-[2-(2-hydroxyethoxy) ethyl]-urea
N'-(2,4-difluorophenyl)-N-[5-(4,5-diphenyl-1H-imidazol-2-ylthio) pentyl]-N-[2-(4-morpholinyl)ethyl]-urea
N-[5-[4,5-bis(4-methoxyphenyl)-1H-imidazol-2-ylthio]pentyl]-N '-(2,4-difluorophenyl)-N-[2-(2-methoxyethoxy)ethyl]-urea
N-[5-[4,5-bis(4-methoxyphenyl)-1H-imidazol-2-ylthio]-pentyl]-N-[2-(2-methoxyethoxy)-ethyl]-N'-(1-methylethyl)-urea or a pharmaceutically acceptable salt thereof.
Included within the family of compounds of Formula I are the tautomeric forms of the described compounds, isomeric forms including diastereoisomers and individual enantiomers, and the pharmaceutically-acceptable salts thereof. The term "pharmaceutically-acceptable salts" embraces salts commonly used to form alkali metal salts and to form addition salts of free acids or free bases. Since the compounds contain basic nitrogen atoms, such salts are typically acid addition salts. The phrase "pharmaceutically-acceptable salts" is intended to embrace alkyl quaternary ammonium salts and n-oxides. The nature of the salt is not critical, provided that it is pharmaceutically acceptable, and acids which may be employed to form such salts are, of course, well known to those skilled in this art. Examples of acids which may be employed to form pharmaceuically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of the invention.

Also embraced within this invention is a class of pharmaceutical compositions comprising one or more of the described compounds in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alchohol, and then tableted or encapsulated for cenvenient administration. Such capsules or tablets may contain a controlled release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

DETAILED DESCRIPTION OF THE INVENTION

Synthesis

The novel compounds of Formula (I) may be prepared using the reactions and techniques described in this section. The reactions are performed in solvents appropriate to the reagents and materials employed and suitable for the transformation being effected. It is understood by those skilled in the art of organic synthesis that the functionality present on the imidazole and other portions of the molecule must be compatible with the reagents and reaction conditions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternate methods described must then be used.

Several suitable methods of synthesis of compounds of Formula (I) exist, and one can be chosen which best accounts for the particular compound structure. One such method is depicted in Scheme I, which can be used to prepare compounds of Formula (I) wherein X is S. The requisite 4-imidazolin-2-thione (2) wherein X is S and $R^3$ is defined above can be converted into the corresponding alkali metal salt by the addition of a base such as sodium hydride in an appropriate polar aprotic solvent such as N,N-dimethylformamide. Reaction with compounds of Formula (3), which bear a suitable leaving group such as chloride, bromide, iodide, mesylate or rosylate, in a polar aprotic solvent such as N,N-dimethylformamide, at temperatures at or below the boiling point of the solvent, then afford compounds of Formula (4). Alternatively, compounds of Formula (1) wherein X is S can be allowed to react with compounds of Formula (3) in the presence of a proton-scavenging base such as potassium carbonate in a solvent such as acetone or tetrahydrofuran, at reflux temperature. In the case wherein M is not iodide, a catalyst can be used to provide iodide ions, which is chosen so as to be soluble in the chosen solvent.

The strategy shown in Scheme I can be employed for imidazoles for Formula (I) wherein X is NH and $R^3$ is not H. For the corresponding compounds wherein X is NH and $R^3$ is H, it is usually necessary to protect the ring nitrogen atom, due to the preference for such compounds to alkylate at a ring nitrogen atom. The protecting group is preferably stable under basic conditions and easily removed under acidic conditions. The protected 2-aminoimidazole can then be used to prepare compounds of Formula (4) wherein $R^3$ is a protecting group. The protecting group can be removed in a subsequent step.

Scheme I

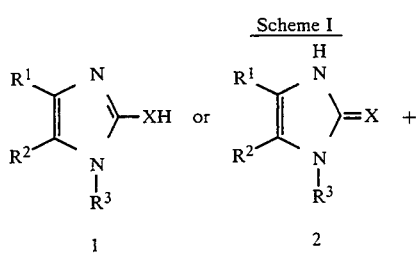

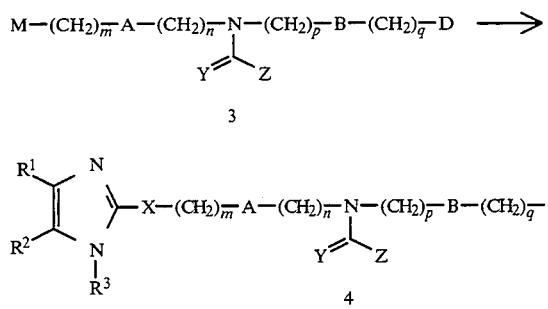

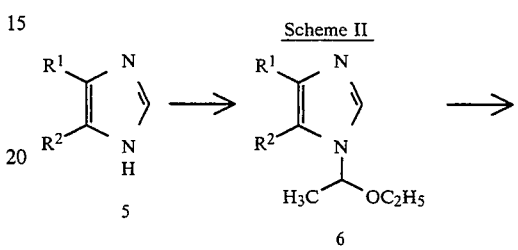

For the cases wherein X═CH₂, the strategy employed in Scheme II is recommended. A 2-unsubstituted imidazole, compound (5), is protected with such groups as the ethoxyethyl (according to the procedure of Manoharan and Brown, *J. Org. Chem.* 1988, 53, 1107–1110) as an example. This protected compound of Formula (6) can be converted to the 2-lithio derivative of Formula (7) by the treatment at low temperatures with an organolithium reagent in an aprotic solvent with or without the presence of a suitable cosolvent. The 2-lithio compound of Formula (7) is then treated with an electrophilic reagent (8) to afford the 2-substituted imidazole (9) upon workup and imidazole deprotection. The compound of Formula (9) is then further elaborated to give compounds of Formula (4) wherein X is CH₂.

Compounds of Formula (4) wherein X is S(O)$_r$ and r is 1 or greater can be made from compounds of Formula (4) wherein X is S, by the treatment in a suitable solvent at cold or ambient temperatures with an oxidizing agent, such as 3-chloroperoxybenzoic acid, potassium peroxomonosulfate, potassium permanganate, etc. The oxidation state of sulfur can be specified by careful control of stoichiometry and temperature in this reaction.

It may prove convenient to attach the heterocycle unit at an earlier stage of the synthesis, in which case the method of Scheme III may be employed. An alkylation reaction employing heterocycles of Formula (1) or (2) and (3) (vide supra). The product amide of formula (1) is then treated with a suitable reducing agent such as lithium aluminum hydride, diisobutylaluminum hydride or sodium bis(methoxyethoxy) aluminum hydride in solvents such as tetrahydrofuran or toluene at temperatures ranging from sub-zero to the boiling point of the solvent.

Scheme II

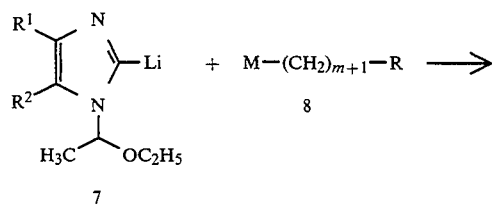

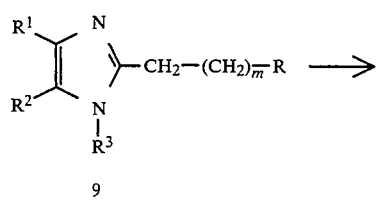

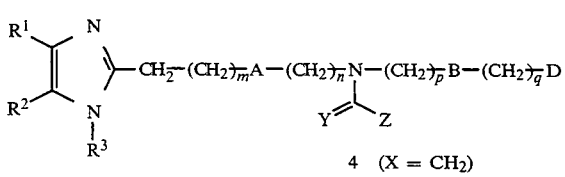

Scheme III

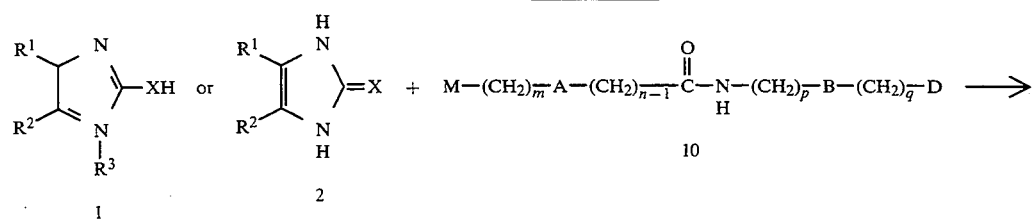

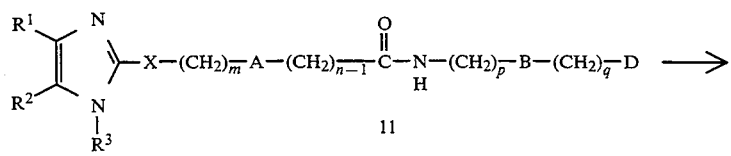

-continued
Scheme III

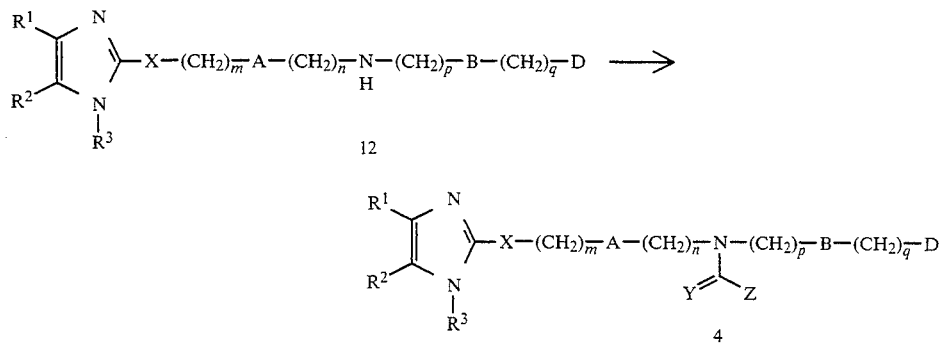

The compounds of Formula (4) wherein Y is O and Z is NR[4], OR[4] or R[4] are prepared by the reaction of the secondary amines of Formula (12) with the requisite isocyanates, chloroformates, acid chlorides, activated urea or activated carboxylic acid derivatives in an appropriate solvent such as hexane, toluene, diethyl ether, diphenyl ether, methylene chloride or tetrahydrofuran at a temperature at or below the boiling point of the solvent. The guanidines of Formula (4), wherein Y is NH and Z is NR[4], are prepared by the reaction of the secondary amines of Formula (12) with an appropriately substituted S-methyl carbamimidothioate salt (Rasmussen and Villani, *Synthesis* 1988, 460) in acetonitrile or dioxane at reflux. The amines of Formula (4), wherein Y is H$_2$, are prepared by the reaction of the corresponding ureas or amides of Formula (4) wherein Y is O with a reducing agent such as lithium aluminum hydride or other such reagents in an appropriate aprotic solvent such as hexane, toluene, diethyl ether or tetrahydrofuran at temperatures at or below the boiling point of the solvent. The thioureas of Formula (4) wherein X is S, O or NH, Y is S and Z is NHR[4] can be prepared in an analogous manner by the reaction of the secondary amines of Formula (12) with the requisite isothiocyanate. Alternatively, the thioureas or thioamides of Formula (4) wherein Y is S and Z is R[4] can be prepared from the ureas or amides of Formula (4) by the reaction with Lawesson's reagent or diphosphorus pentasulfide in an appropriate solvent such as toluene.

The imidazole compounds of Formulae (1), (2) or (5) needed for the above-described syntheses may be prepared using standard heterocyclic technology familiar to those skilled in the art.

An alternative route to that of Scheme III is portrayed in Scheme IV. The amides of Formula (13) are reacted with the heterocycles of Formula (1) or (2) in a manner analogous to that for the amides of Formula (10). The amides of Formula (14) are then reduced exactly as for the reduction of compounds of Formula (11) to obtain the previously described amines of Formula (12).

Scheme IV

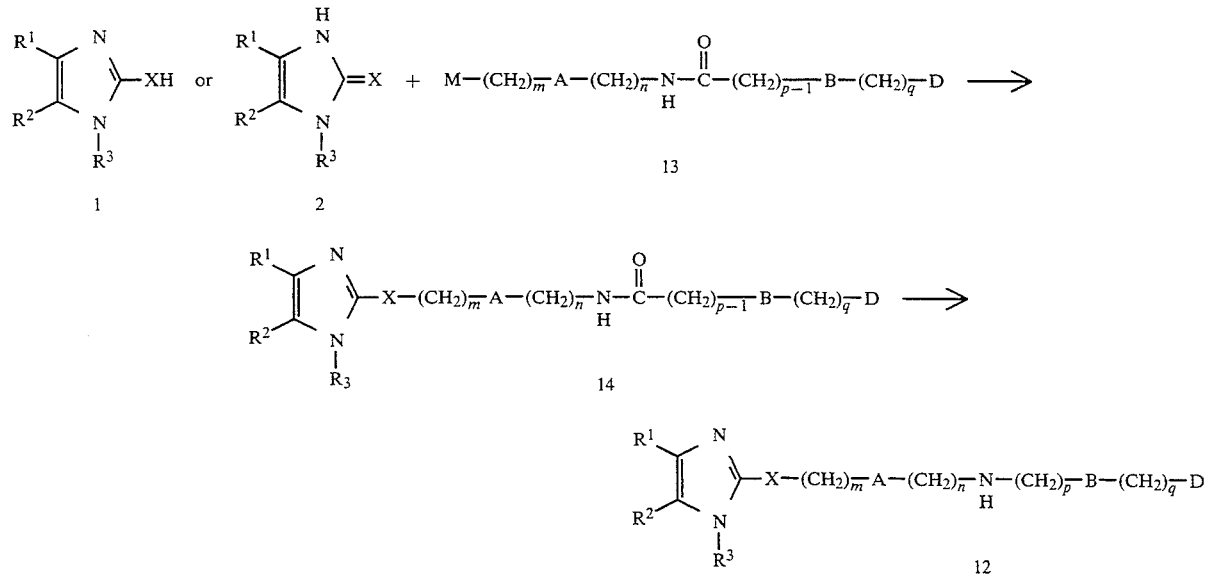

One method for the preparation of compounds of Formula (3) is shown in Scheme V. Amino alcohols of Formula (15) are coupled with compounds of Formula (16), wherein Q is OH, using amide bond-forming reactions which are well known in the chemical literature. One method for amide bond formation is to use a coupling reagent which generates a reactive intermediate such as a mixed anhydride or active ester. Examples of such coupling agents are disubstituted carbodiimides, N,N'-carbonyldiimidazole, diphenylphosphoryl azide and the like. For example, the coupling can be carried out with a disubstituted carbodiimide such as dicyclohexylcarbodiimide in an appropriate solvent such as methylene chloride, acetonitrile, toluene or N,N-dimethylformamide. Nucleophilic hydroxy compounds such as 1-hydroxy-1H-benzotriazole, which form highly active esters, may be added to catalyze the reaction. Another approach is to employ carboxylic acid chlorides for Formula (16) wherein Q is Cl, which are allowed to react with a primary amine in the presence of a base such as triethylamine to afford the amides of Formula (17).

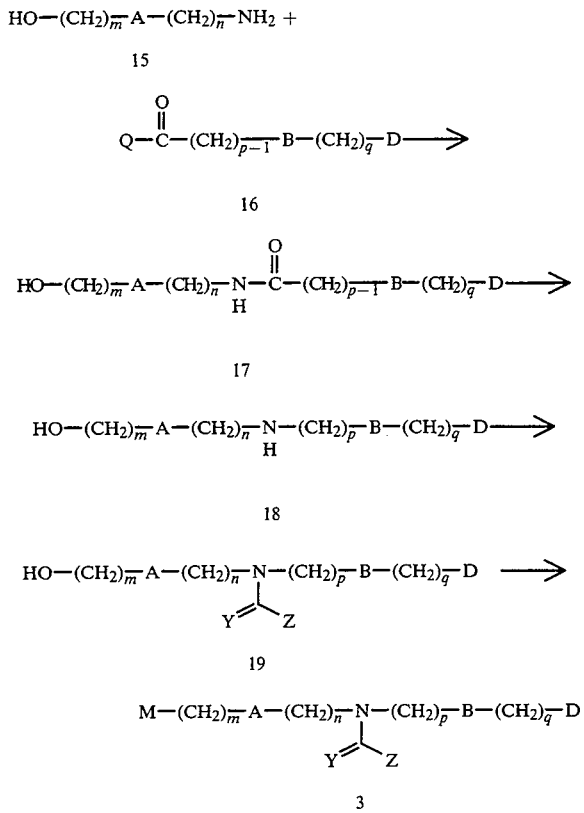

Reduction of the amides of Formula (17) using the above-described reduction methods affords the amines of Formula (18), which are functionalized as described above to yield hydroxy compounds of Formula (19). The hydroxyl group can be converted to halide by a number of methods: directly, by the action of triphenylphosphine/carbon tetrabromide or triphenylphosphine/iodine; or indirectly, by first converting the hydroxyl group to the tosylate group (via the treatment with toluenesulfonyl chloride and pyridine in an appropriate solvent) or mesylate group (via the treatment with methanesulfonyl chloride and triethylamine), and then displacement with iodide ion by the treatment of the rosylate or mesylate derivative with sodium iodide in refluxing acetone. The halide compound of Formula (3) is thus produced.

In the case wherein A is (C=O) O or (C=O)NR$^6$, the route shown in Scheme VI, can be used. Carboxylic acids of Formula (20) wherein A' is O or NR$^6$ can be coupled with amines of Formula (21) in the manner described above to prepare amides of Formula (22). Reduction to amines of Formula (23) as usual, followed by amine functionalization, affords compounds of Formula (24). These are then treated with a halo carboxylic acid chloride in the presence of a base such as triethylamine in an appropriate solvent to give compounds of Formula (26). These compounds are then subjected to the chemistry shown in Scheme I.

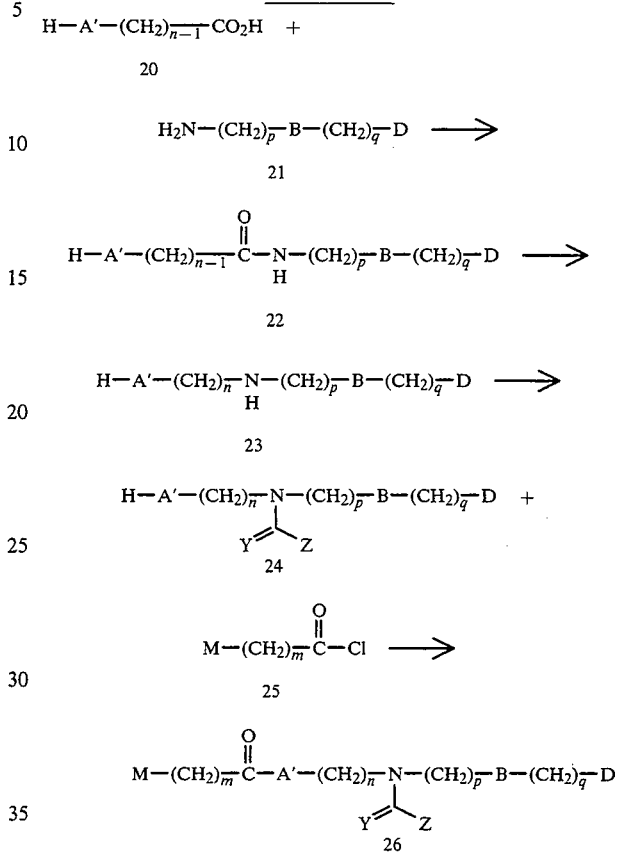

Alternatively, compounds of Formula (23) may be prepared by the amide coupling reaction of amines of Formula (27), shown in Scheme VII. The amides of Formula (28) are then reduced in the usual manner to yield amines of Formula (23).

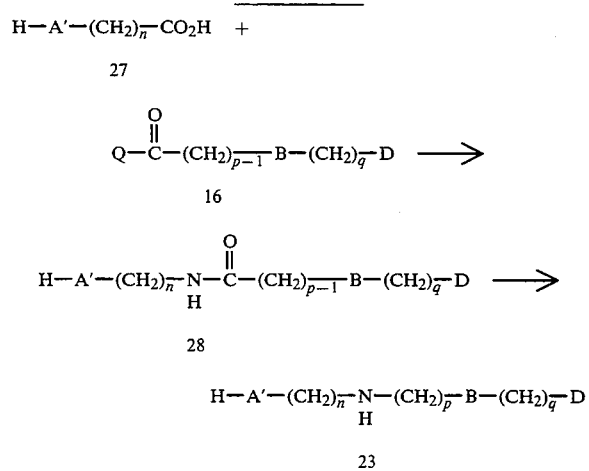

Compounds of Formula (11) can be prepared in alternative methods, which are depicted in Schemes VIII and IX. The alkylation of heterocycles of Formula (1) or (2) with a halo ester of Formula (29) is performed exactly as for compounds (3), (10), or (13) above. The esters of Formula (3) are hydrolyzed to the corresponding acids of Formula (31) by methods which are well known in the chemical literature. For example, the hydrolysis can be accomplished by reaction with an alkali metal hydroxide in aqueous or organic solvents such as water, alcohols, ethers or mixtures thereof, followed by acidification with a mineral acid. Carboxylic acids of Formula (31) can be coupled with amines of Formula (21) in the usual manner to give amides of Formula (11). Alternatively, halo acid derivatives of Formula (32), wherein Q is either OH or Cl, can be coupled with amines of Formula (21) to afford amides of Formula (11) directly.

-continued

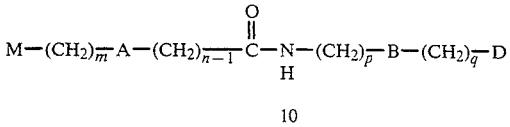

A special synthesis can be used for compounds of Formula (12) wherein A is $NR^7$. Scheme X shows the coupling reaction of the amino acid compounds (34) and the halo acid chloride compounds (33), which, due to possible solubility problems in organic solvents, can

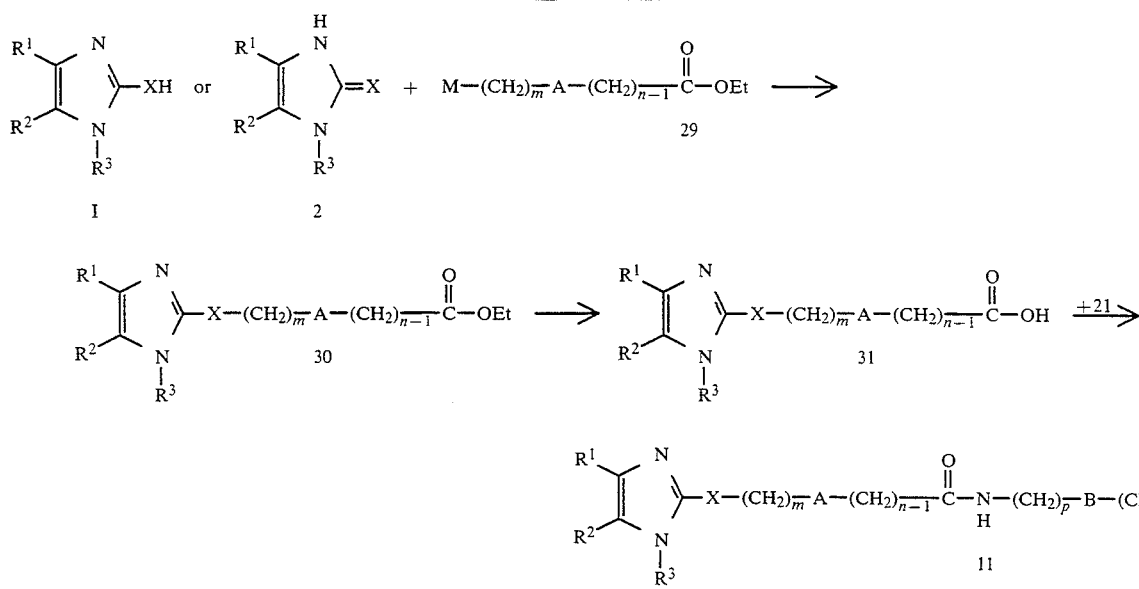

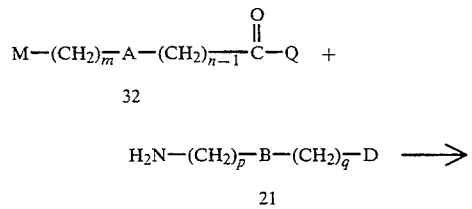

be performed by the method of Schotten and Baumann (*Ber. Deut. Chem. Ges.* 1884, 17, 2545), namely in concentrated aqueous sodium hydroxide. The halo amide compounds of Formula (35) can be alkylated with heterocycles of Formula (1) or (2) to afford an amide-acid compound of Formula (36). This compound can be coupled using the usual amide-forming methodology to give the dipeptide compound of Formula (37). Treatment with a large excess of one of the usual reducing agents, in the manner used throughout, affords the diamine compound of Formula (38), which is equivalent to Formula (12) wherein $A=NR^7$.

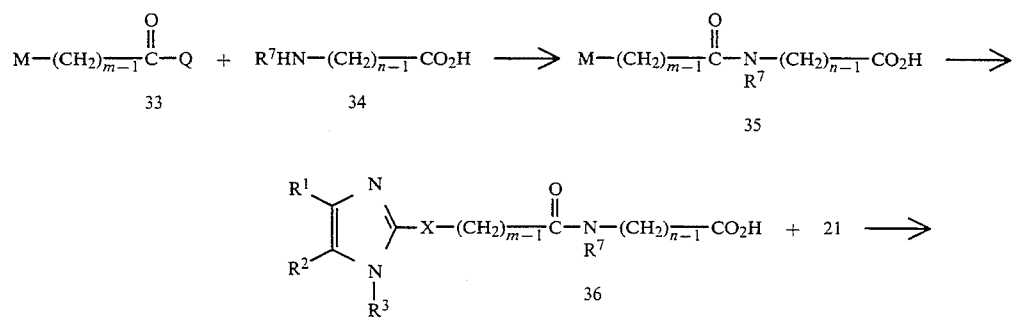

-continued
Scheme X

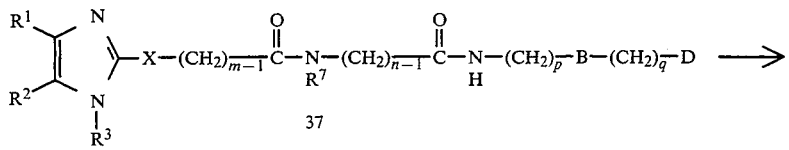

37

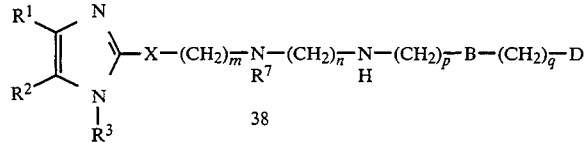

38

Scheme XI

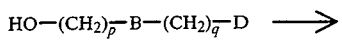
39

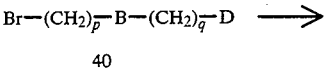
40

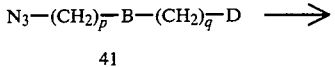
41

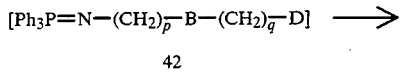
42

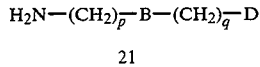
21

In the event wherein compounds of Formula (21) are not commercially available or readily prepared, a route for their synthesis from the corresponding alcohol compound of Formula (39) can be used (Scheme XI). Methods for the conversion of the hydroxy group to bromide can be accomplished by the treatment with such reagents as triphenylphosphine/carbon tetrabromide or phosphorus tribromide in solvents such as methylene chloride or benzene. The bromide can be displaced by azide ion by the treatment of compounds of Formula (40) with alkali azide salts in polar solvents such as N,N-dimethylformamide or dimethylsulfoxide at temperatures at or below the boiling point of the solvent. The azide compounds of Formula (41) are then subjected to treatment with triphenylphosphine in etheric solvents. The intermediate triphenylphosphine imine compounds of Formula (42) are not isolated, but are hydrolyzed in situ by the addition of water at ambient temperature, which produces the amine compounds of Formula (21).

Preparation of pharmaceutically suitable salts of Formula (I) can be carried out in accordance with well known techniques for forming salts. Physiologically acceptable salts include acid addition salts, e.g., hydrochloric, sulfuric, acetic, trifluoroacetic, succinic, citric, and benzene sulfonic acid salts.

The compounds of this invention and their preparation can be further understood by the following examples, which exemplify but do not constitute a limitation of the invention. In these examples, unless otherwise indicated, all temperatures are in degrees centigrade and parts and percentages are by weight.

EXAMPLE 1

Preparation of
N-[2-(diethylamino)ethyl]-N-[5-(4,5-diphenyl-1H-imidazol-2-ylthio)pentyl]-N'-(1-methylethyl)-urea Part A 5-(4,5-diphenyl-1H-imidazol-2-ylthio)-pentanoic acid (3.73 g, 10.58 retool) was dissolved in 40 mL dry dimethylformamide, and treated with solid hydroxybenzotriazole hydrate (1.77 g, 13.10 retool). Then, a 20 mL dimethylformamide solution of N,N-diethylethylenediamine (2.00 mL, 14.24 mmol) was added dropwise. The mixture was cooled to 0° C., and solid dicyclohexylcarbodiimide (2.81 g, 13.62 mmol) was added in small portions over 20 minutes. The mixture was allowed to slowly warm and stirred for 48 hours, then poured into 150 mL ethyl acetate. This mixture was washed with water (3×150 mL), and the water washings were back-extracted in sequence with ethyl acetate (150 mL). The organic phases were combined, dried over anhydrous sodium sulfate, and evaporated to afford a pale yellow oil. The oil was separated by flash chromatography (1:4 methanol-methylene chloride) to afford N-[2-(diethylamino)ethyl]-5-(4,5-diphenyl-1H-imidazol-2-ylthio)-pentanamide (3.77 g, 8.37 mmol, 79%). $^1$H NMR (300 MHz, CDCl$_3$): 7.56–7.49 (4H, m); 7.33–7.17 (6H, m); 6.91 (1H, br s); 3.16 (2H, br d, J=6 Hz); 2.97 (2H, t, J=7 Hz); 2.68–2.49 (6H, m); 2.29 (2H, t, J=6 Hz); 2.00–1.57 (4H, m); 1.02 (6H, t, J=7 Hz).

Part B

A 20 mL toluene solution of Red-Al ™ (3.0 mL of 3.7M soln. in toluene, 11.1 mmol) was stirred at ambient temperature under nitrogen atmosphere, while a 20 mL toluene solution of the amide prepared above was added dropwise over 20 minutes. After stirring for 18 hours, the mixture was cooled to 0° C., and treated dropwise with 12 mL 1N aqueous sodium hydroxide. The phases were separated, and the aqueous phase was saturated with sodium chloride and extracted with methylene chloride (3×100 mL). The organic phases were combined, dried over anhydrous potassium carbonate, and evaporated to afford N-[2-(diethylamino)ethyl]-5-(4,5-diphenyl-1H-imidazol-2-ylthio)-pentanamine, sufficiently pure for the next step. $^1$H NMR (300 MHz, CDCl$_3$): 7.50–7.07 (10H, m); 3.00 (2H, t, J=7.0 Hz); 2.58–2.37 (10H, m); 1.65–1.18 (6H, m); 0.89 (6H, t, J=7.0 Hz).

Part C

The diamine prepared above (1.01 g, 2.30 mmol) was dissolved in 30 mL toluene, cooled to 0° C., and treated with isopropyl isocyanate (0.23 mL, 2.34 mmol). After warming to ambient temperature and stirring for 18 h, the reaction mixture was evaporated and separated by flash chromatography to afford the product (1.13 g, 2.17 mmol, 94%). A portion was recrystallized to afford analytically pure N-[2-(diethylamino) ethyl]-N-[5-(4,5-diphenyl-1H-imidazol-2-ylthio)pentyl]-N'-(1-methylethyl)-urea; melting point: 58°–59° C. (ethyl acetate-hexane); $^1$H NMR (300 MHz, CDCl$_3$): 7.57–7.53 (4H, m); 7.33–7.18 (6H, m); 3.81–3.70 (1H, m); 3.38–3.24 (4H, m); 2.98 (2H, t, J=6.4 Hz); 2.65–2.62 (6H, m); 1.85–1.68 (2H, m); 1.59–1.46 (4H, m); 1.10 (6H, t, J=6.9 Hz); 1.06 (6H, d, J=6.6 Hz).

EXAMPLE 32

Preparation of
N-[2-(2-(4,5-bis(4-methoxyphenyl)-1H-imidazol-2-ylthio)
ethoxy)ethyl]-N-[2-(N-butyl-N-methylamino)ethyl]-N'-(2,4-difluorophenyl) urea Part A Sarcosine (14.93 g, 168 mmol) was treated with 4N aqueous sodium hydroxide solution (42 mL, 168 mmol) at −10° C. Then, butyryl cholride (20 mL, 193 mmol) and additional 4N aqueous sodium hydroxide solution (42 mL, 168 mmol) were added dropwise simultaneously over 30 minutes. After stirring and slow warming to 20° C. overnight, the mixture was poured into water (400 mL), neutralized to pH 4 with concentrated hydrochloric acid, and saturated with sodium chloride. This mixture was extracted with ethyl acetate (2×400 mL), and the extracts were combined, dried over anhydrous magnesium sulfate and evaporated. The residual oil (19.65 g, 123 mmol, 74%) was sufficiently pure N-butyrylsarcosine. $^1$H NMR (CDCl$_3$): 11.10 (1H, br s); 4.17 (2H, s); 3.10 (3H, s); 2.33 (2H, t, J=7.3 Hz); 1.75–1.61 (2H, m); 0.97 (3H, t, J=7.3 Hz).

Part B

The carboxylic acid prepared in Part A above was dissolved in anhydrous tetrahydrofuran (100 mL), and cooled to 0° C. This solution was treated with 1-hydroxy-1H-benzotriazole hydrate (10.5 g, 77.7 mmol) and 2-(2-hydroxyethoxy)ethylamine (6.0 mL, 83.3 mmol). Then, dicyclohexylcarbodiimide (20.3 g, 98.4 mmol) was added in small portions to the reaction mixture over 15 minutes. The solution was allowed to stir for 48 hours, then poured into water (200 mL) and extracted with methylene chloride (200 mL). The aqueous phase was saturated with sodium chloride and reextracted with methylene chloride (200 mL). The extracts were combined, dried over anhydrous magnesium sulfate and evaporated. The residual oil was separated by flash chromatography (1:19 methanol-methylene chloride) to afford N-butyryl-N'-[2-(2-hydroxyethoxy)ethyl]sarcosinamide (3.98 g, 16.2 mmol, 24%). $^1$H NMR (CDCl$_3$): 6.55 (1H, br s); 5.92 (1H, br s); 3.99 (2H, s); 3.78–3.71 (2H, m); 3.60–3.52 (4H, m); 3.50–3.40 (2H, s); 3.12 (3H, s); 2.35 (2H, t, J=7.5 Hz); 1.71–1.57 (2H, m); 0.95 (3H, t, J=7.3 Hz).

Part C

The alcohol prepared in Part B above (3.04 g, 12.3 mmol) was dissolved in methylene chloride (50 mL), and carbon tetrabromide (4.95 g, 14.9 mmol) was added. This solution was stirred while a solution of triphenylphosphine (3.92 g, 14.9 mmol) in methylene chloride (20 mL) was added dropwise over 30 minutes. After stirring an additional 18 hours, the reaction mixture was evaporated, and the oily residue was separated by flash chromatography (1:1 acetone-hexane) to afford N'-[2-(2-bromoethoxy) ethyl]-N-butyryl-sarcosinamide (2.05 g, 6.67 mmol, 54%) as an oil, which was used directly in the next step.

This bromide, 4,5-bis(4-methoxyphenyl)-1H-imidazole-2-thiol (2.08 g, 6.66 mmol), potassium carbonate (1.20 g, 8.68 mmol) and tetra-n-butylammonium iodide (490 mg) were mixed in 20 mL anhydrous tetrahydrofuran, and heated to reflux under nitrogen atmosphere for 18 hours. After cooling, the mixture was poured into water (100 mL), and extracted with methylene chloride (100 mL). The aqueous phase was neutralized to pH 6 with dropwise addition of 6N aqueous sodium hydroxide solution, saturated with sodium chloride, and reextracted with methylene chloride (100 mL). The extracts were combined, dried over anhydrous magnesium sulfate and evaporated. The oily residue was separated by flash chromatography (1:4 isopropanol-ethyl acetate) to afford N'-N-butyryl-[2-(2-(4,5-bis(4-methoxyphenyl)- 1H-imidazol-2-ylthio)ethoxy)ethyl]-sarcosinamide (2.68 g, 4.96 mmol, 74%). $^1$H NMR (CDCl$_3$): 7.50–7.40 (4H, m); 6.91–6.80 (4H, m); 4.02 (1.53H, s); 4.01 (0.47H, s); 3.81 (6H, s); 3.80–3.25 (8H, m); 3.10 (2.30H, s); 3.06 (0.70H, s); 2.32 (1.53H, t, J=7.3 Hz); 2.30 (0.47H, t, J=6.9 Hz); 1.75–1.60 (2H, m); 1.02 (0.70H, t, J=7.3 Hz); 0.88 (2.30H, t, J=7.3 Hz).

Part D

A solution of sodium bis(methoxyethoxy)aluminum hydride in toluene (9.0 mL, 3.4M, 30.6 mmol) was added to 50 mL toluene, and cooled to 0° C. A solution of the amide from Part C above in tetrahydrofuran (50 mL) was added dropwise over 30 minutes. The mixture was then heated to 80° C. for 18 hours, and cooled to 0° C. Excess hydride was quenched by the slow addition of 2M aqueous sodium hydroxide solution (20 mL). This mixture was poured into 100 mL water, and extracted with methylene chloride (2×200 mL). The organic extracts were combined, dried over anhydrous potassium carbonate and evaporated. Separation by flash chromatography (1:9 methanol-methylene chloride) afforded the product, N-[2-(2-(4,5-bis(4-methoxyphenyl)-1H-imidazol-2-ylthio) ethoxy)ethyl]-N'-butyl-N'-methyl-ethylenediamine (870 mg, 1.70 mmol, 34%) as a gum. $^1$H NMR (CDCl$_3$): 7.43 (4H, d, J=8.8 Hz); 6.84 (4H, d, J=8.8 Hz); 3.80 (6H, s); 3.77–3.67 (4H, m); 3.12 (2H, t, J=5.3 Hz); 2.88 (2H, t, J=5.0 Hz); 2.66 (2H, t, J=6.9 Hz); 2.53–2.43 (2H, m); 2.37 (2H, t, J=5.9 Hz); 2.10 (3H, s); 1.55–1.41 (1H, m); 1.38–1.18 (4H, m); 0.85 (3H, t, J=7.4 Hz).

Part E

The amine from Part D above (811 mg, 1.58 mmol) was dissolved in methylene chloride (10 mL), and cooled to 0° C. Neat 2,4-difluorophenylisocyanate (0.20 mL, 1.69 mmol) was added via syringe, and the mixture was stirred and warmed slowly to 20° C. over 18 hours. The reaction mixture was evaporated, and the oily residue separated by flash chromatography (1:19 methanol-methylene chloride) to afford the product, N-[2-(2-(4,5-bis(4-methoxyphenyl) -1H-imidazol-2-ylthio)ethoxy)ethyl]-N-[2-(N-butyl-N-methylamino)ethyl]-N'-(2,4-difluorophenyl)-urea, as an oil (606 mg, 0.91 mmol, 57%). $^1$H NMR (CDCl$_3$): 7.64–7.55 (1H, m); 7.54–7.23 (4H, br s); 6.82 (4H, d, J=8.4 Hz); 6.72–6.63 (1H, m); 6.62–6.55 (1H, m); 3.80 (6H, s); 3.79–3.70 (4H, m); 3.60 (2H, br t, J=4.8 Hz); 3.49–3.40 (2H, m); 3.12 (2H, t, J=5.3 Hz); 2.64 (2H, br s); 2.45 (2H, br t, J=7.7 Hz); 2.33 (3H, s); 1.52–1.40 (2H, m); 1.33–1.21 (2H, m); 0.86

(3H, t, J=7.4 Hz). High-resolution mass spectrum: for M-C$_7$H$_3$F$_2$NO (C$_{28}$H$_{40}$N$_4$O$_3$S), calculated 512.2821, observed 512.2827, difference 1.2 ppm.

Compounds 1–100 in Table 1 were prepared or could be prepared analogously by the procedures described in Examples 1 and 32 by employing the appropriately substituted starting materials. The compounds in Table 1 represent those analogues bearing an aminoalkyl group on the trisubstituted nitrogen atom.

TABLE 1

| Example | R$^1$ | R$^2$ | R$^3$ | X | m | A | n | Y | Z | p | R$^6$ | q | D | mp |
|---|---|---|---|---|---|---|---|---|---|---|---|---|---|---|
| 1 | C$_6$H$_5$ | C$_6$H$_5$ | H | S | 2 | CH$_2$ | 2 | O | NH-i-C$_3$H$_7$ | 2 | C$_2$H$_5$ | 2 | H | 58–59 |
| 2 | C$_6$H$_5$ | C$_6$H$_5$ | H | S | 2 | CH$_2$ | 2 | O | NH-2,4-C$_6$H$_3$F$_2$ | 2 | C$_2$H$_5$ | 2 | H | 65–66 |
| 3 | C$_6$H$_5$ | C$_6$H$_5$ | H | S | 2 | CH$_2$ | 2 | O | NHC$_4$H$_9$ | 2 | C$_2$H$_5$ | 2 | H | — |
| 4 | C$_6$H$_5$ | C$_6$H$_5$ | H | S | 2 | CH$_2$ | 2 | O | OCH$_2$C$_6$H$_5$ | 2 | C$_2$H$_5$ | 2 | H | — |
| 5 | C$_6$H$_5$ | C$_6$H$_5$ | H | SO$_2$ | 2 | CH$_2$ | 2 | O | NHCH$_3$ | 2 | C$_2$H$_5$ | 2 | H | — |
| 6 | C$_6$H$_5$ | C$_6$H$_5$ | H | NH | 2 | CH$_2$ | 2 | O | NHCH$_3$ | 2 | C$_2$H$_5$ | 2 | H | — |
| 7 | 4-CH$_3$OC$_6$H$_4$ | 4-CH$_3$OC$_6$H$_4$ | H | S | 2 | CH$_2$ | 2 | O | NH-i-C$_3$H$_7$ | 2 | C$_2$H$_5$ | 2 | H | — |
| 8 | 4-CH$_3$SC$_6$H$_4$ | 4-CH$_3$SC$_6$H$_4$ | H | S | 2 | CH$_2$ | 2 | O | NH-i-C$_3$H$_7$ | 2 | C$_2$H$_5$ | 2 | H | — |
| 9 | i-C$_3$H$_7$ | i-C$_3$H$_7$ | H | S | 2 | CH$_2$ | 2 | O | NH-i-C$_3$H$_7$ | 2 | C$_2$H$_5$ | 2 | H | — |
| 10 | C$_6$H$_5$ | C$_6$H$_5$ | H | S | 2 | O | 2 | O | NH-i-C$_3$H$_7$ | 2 | C$_2$H$_5$ | 2 | H | — |
| 11 | 4-CH$_3$OC$_6$H$_4$ | 4-CH$_3$OC$_6$H$_4$ | H | S | 2 | O | 2 | O | NH-i-C$_3$H$_7$ | 2 | C$_2$H$_5$ | 2 | H | — |
| 12 | 4-CH$_3$OC$_6$H$_4$ | 4-CH$_3$OC$_6$H$_4$ | H | S | 2 | O | 2 | O | NH-2,4-C$_6$H$_3$F$_2$ | 2 | C$_2$H$_5$ | 2 | H | — |
| 13 | 4-CH$_3$OC$_6$H$_4$ | 4-CH$_3$OC$_6$H$_4$ | H | S | 2 | O | 2 | O | CH$_2$C$_6$H$_5$ | 2 | C$_2$H$_5$ | 2 | H | — |
| 14 | C$_6$H$_5$ | H | H | S | 2 | CH$_2$ | 2 | O | NH-i-C$_3$H$_7$ | 2 | C$_2$H$_5$ | 2 | H | — |
| 15 | C$_6$H$_5$ | C$_6$H$_5$ | CH$_3$ | S | 2 | CH$_2$ | 2 | O | NH-i-C$_3$H$_7$ | 2 | C$_2$H$_5$ | 2 | H | — |
| 16 | C$_6$H$_5$ | C$_6$H$_5$ | H | S | 2 | CH$_2$ | 2 | O | NH-i-C$_3$H$_7$ | 2 | C$_2$H$_5$ | 2 | H | — |
| 17 | C$_6$H$_5$ | C$_6$H$_5$ | H | S | 2 | S | 2 | O | NH-i-C$_3$H$_7$ | 2 | C$_2$H$_5$ | 2 | H | — |
| 18 | C$_6$H$_5$ | C$_6$H$_5$ | H | SO$_2$ | 2 | SO$_2$ | 2 | O | NH-i-C$_3$H$_7$ | 2 | C$_2$H$_5$ | 2 | H | — |
| 19 | 4-(CH$_3$)$_2$N—C$_6$H$_4$ | 4-(CH$_3$)$_2$N—C$_6$H$_4$ | H | S | 2 | CH$_2$ | 2 | O | NH-i-C$_3$H$_7$ | 2 | C$_2$H$_5$ | 2 | H | — |
| 20 | C$_6$H$_5$ | C$_6$H$_5$ | H | S | 3 | O | 3 | O | NH-2-C$_5$H$_4$N | 2 | C$_2$H$_5$ | 2 | H | — |
| 21 | C$_6$H$_5$ | C$_6$H$_5$ | H | S | 2 | CH$_2$ | 2 | O | NH-i-C$_3$H$_7$ | 2 | CH$_3$ | 4 | H | — |
| 22 | C$_6$H$_5$ | C$_6$H$_5$ | H | S | 2 | CH$_2$ | 2 | O | NH-2,4-C$_6$H$_3$F$_2$ | 2 | CH$_3$ | 4 | H | — |
| 23 | C$_6$H$_5$ | C$_6$H$_5$ | H | OS | 2 | CH$_2$ | 2 | O | NHC$_4$H$_9$ | 2 | CH$_3$ | 4 | H | — |
| 24 | C$_6$H$_5$ | C$_6$H$_5$ | H | S | 2 | CH$_2$ | 2 | O | OCH$_2$C$_6$H$_5$ | 2 | CH$_3$ | 4 | H | — |
| 25 | C$_6$H$_5$ | C$_6$H$_5$ | H | SO$_2$ | 2 | CH$_2$ | 2 | O | NHCH$_3$ | 2 | CH$_3$ | 4 | H | — |
| 26 | C$_6$H$_5$ | C$_6$H$_5$ | H | NH | 2 | CH$_2$ | 2 | O | NHCH$_3$ | 2 | CH$_3$ | 4 | H | — |
| 27 | 4-CH$_3$OC$_6$H$_4$ | 4-CH$_3$OC$_6$H$_4$ | H | S | 2 | CH$_2$ | 2 | O | NH-i-C$_3$H$_7$ | 2 | CH$_3$ | 4 | H | — |
| 28 | 4-CH$_3$SC$_6$H$_4$ | 4-CH$_2$SC$_6$H$_4$ | H | S | 2 | CH$_2$ | 2 | O | NH-i-C$_3$H$_7$ | 2 | CH$_3$ | 4 | H | — |
| 29 | i-C$_3$H$_7$ | i-C$_3$H$_7$ | H | S | 2 | CH$_2$ | 2 | O | NH-i-C$_3$H$_7$ | 2 | CH$_3$ | 4 | H | — |
| 30 | C$_6$H$_5$ | C$_6$H$_5$ | H | S | 2 | O | 2 | O | NH-i-C$_3$H$_7$ | 2 | CH$_3$ | 4 | H | — |
| 31 | 4-CH$_3$OC$_6$H$_4$ | 4-CH$_3$OC$_6$H$_4$ | H | S | 2 | O | 2 | O | NH-i-C$_3$H$_7$ | 2 | CH$_3$ | 4 | H | — |
| 32 | 4-CH$_3$OC$_6$H$_4$ | 4-CH$_3$OC$_6$H$_4$ | H | S | 2 | O | 2 | O | NH-2,4-C$_6$H$_3$F$_2$ | 2 | CH$_3$ | 4 | H | oil$^a$ |
| 33 | 4-CH$_3$OC$_6$H$_4$ | 4-CH$_3$OC$_6$H$_4$ | H | S | 2 | O | 2 | O | CH$_2$C$_6$H$_5$ | 2 | CH$_3$ | 4 | H | — |
| 34 | C$_6$H$_5$ | H | H | S | 2 | CH$_2$ | 2 | O | NH-i-C$_3$H$_7$ | 2 | CH$_3$ | 4 | H | — |
| 35 | C$_6$H$_5$ | C$_6$H$_5$ | CH$_3$ | S | 2 | CH$_2$ | 2 | O | NH-i-C$_3$H$_7$ | 2 | CH$_3$ | 4 | H | — |
| 36 | C$_6$H$_5$ | C$_6$H$_5$ | H | S | 2 | CH$_2$ | 2 | O | NH-i-C$_3$H$_7$ | 2 | CH$_3$ | 4 | H | — |
| 37 | C$_6$H$_5$ | C$_6$H$_5$ | H | S | 2 | S | 2 | O | NH-i-C$_3$H$_7$ | 2 | CH$_3$ | 4 | H | — |
| 38 | C$_6$H$_5$ | C$_6$H$_5$ | H | SO$_2$ | 2 | SO$_2$ | 2 | O | NH-i-C$_3$H$_7$ | 2 | CH$_3$ | 4 | H | — |
| 39 | 4-(CH$_3$)$_2$N—C$_6$H$_4$ | 4-(CH$_3$)$_2$N—C$_6$H$_4$ | H | S | 2 | CH$_2$ | 2 | O | NH-i-C$_3$H$_7$ | 2 | CH$_3$ | 4 | H | — |
| 40 | C$_6$H$_5$ | C$_6$H$_5$ | H | S | 3 | O | 3 | O | NH-2-C$_5$H$_4$N | 2 | CH$_3$ | 4 | H | — |
| 41 | C$_6$H$_5$ | C$_6$H$_5$ | H | S | 2 | CH$_2$ | 2 | O | NH-i-C$_3$H$_7$ | 4 | CH$_3$ | 2 | NHC$_6$H$_5$ | — |
| 42 | C$_6$H$_5$ | C$_6$H$_5$ | H | S | 2 | CH$_2$ | 2 | O | NH-2,4-C$_6$H$_3$F$_2$ | 4 | CH$_3$ | 2 | NHC$_6$H$_5$ | — |
| 43 | C$_6$H$_5$ | C$_6$H$_5$ | H | S | 2 | CH$_2$ | 2 | O | NHC$_4$H$_9$ | 4 | CH$_3$ | 2 | NHC$_6$H$_5$ | — |
| 44 | C$_6$H$_5$ | C$_6$H$_5$ | H | S | 2 | CH$_2$ | 2 | O | OCH$_2$C$_6$H$_5$ | 4 | CH$_3$ | 2 | NHC$_6$H$_5$ | — |
| 45 | C$_6$H$_5$ | C$_6$H$_5$ | H | SO$_2$ | 2 | CH$_2$ | 2 | O | NHCH$_3$ | 4 | CH$_3$ | 2 | NHC$_6$H$_5$ | — |
| 46 | C$_6$H$_5$ | C$_6$H$_5$ | H | NH | 2 | CH$_2$ | 2 | O | NHCH$_3$ | 4 | CH$_3$ | 2 | NHC$_6$H$_5$ | — |
| 47 | 4-CH$_3$OC$_6$H$_4$ | 4-CH$_3$OC$_6$H$_4$ | H | S | 2 | CH$_2$ | 2 | O | NH-i-C$_3$H$_7$ | 4 | CH$_3$ | 2 | NHC$_6$H$_5$ | — |
| 48 | 4-CH$_3$SC$_6$H$_4$ | 4-CH$_3$SC$_6$H$_4$ | H | S | 2 | CH$_2$ | 2 | O | NH-i-C$_3$H$_7$ | 4 | CH$_3$ | 2 | NHC$_6$H$_5$ | — |
| 49 | i-C$_3$H$_7$ | i-C$_3$H$_7$ | H | S | 2 | CH$_2$ | 2 | O | NHIC$_3$H$_7$ | 4 | CH$_3$ | 2 | NHC$_6$H$_5$ | — |
| 50 | C$_6$H$_5$ | C$_6$H$_5$ | H | S | 2 | O | 2 | O | NH-i-C$_3$H$_7$ | 4 | CH$_3$ | 2 | NHC$_6$H$_5$ | — |
| 51 | 4-CH$_3$OC$_6$H$_4$ | 4-CH$_3$OC$_6$H$_4$ | H | S | 2 | O | 2 | O | NH-i-C$_3$H$_7$ | 4 | CH$_3$ | 2 | NHC$_6$H$_5$ | — |
| 52 | 4-CH$_3$OC$_6$H$_4$ | 4-CH$_3$OC$_6$H$_4$ | H | S | 2 | O | 2 | O | NH-2,4-C$_6$H$_3$F$_2$ | 4 | CH$_3$ | 2 | NHC$_6$H$_5$ | — |
| 53 | 4-CH$_3$OC$_6$H$_4$ | 4-CH$_3$OC$_6$H$_4$ | H | S | 2 | O | 2 | O | CH$_2$C$_6$H$_5$ | 4 | CH$_3$ | 2 | NHC$_6$H$_5$ | — |
| 54 | C$_6$H$_5$ | H | H | S | 2 | CH$_2$ | 2 | O | NH-i-C$_3$H$_7$ | 4 | CH$_3$ | 2 | NHC$_6$H$_5$ | — |
| 55 | C$_6$H$_5$ | C$_6$H$_5$ | CH$_3$ | S | 2 | CH$_2$ | 2 | O | NH-i-C$_3$H$_7$ | 4 | CH$_3$ | 2 | NHC$_6$H$_5$ | — |
| 56 | C$_6$H$_5$ | C$_6$H$_5$ | H | S | 2 | CH$_2$ | 2 | O | NH-i-C$_3$H$_7$ | 4 | CH$_3$ | 2 | NHC$_6$H$_5$ | — |
| 57 | C$_6$H$_5$ | C$_6$H$_5$ | H | S | 2 | S | 2 | O | NH-i-C$_3$H$_7$ | 4 | CH$_3$ | 2 | NHC$_6$H$_5$ | — |
| 58 | C$_6$H$_5$ | C$_6$H$_5$ | H | SO$_2$ | 2 | SO$_2$ | 2 | O | NH-i-C$_3$H$_7$ | 4 | CH$_3$ | 2 | NHC$_6$H$_5$ | — |
| 59 | 4-(CH$_3$)$_2$N—C$_6$H$_4$ | 4-(CH$_3$)$_2$N—C$_6$H$_4$ | H | S | 2 | CH$_2$ | 2 | O | NH-i-C$_3$H$_7$ | 4 | CH$_3$ | 2 | NHC$_6$H$_5$ | — |

TABLE 1-continued $$R^1\text{-}C(=N)\text{-}N(R^3)\text{-}C(=N)\text{-}R^2 \quad \text{--}X\text{--}(CH_2)_{\overline{m}}\text{--}A\text{--}(CH_2)_{\overline{n}}\text{--}N\text{--}(CH_2)_{\overline{p}}\text{--}N(R^6)\text{--}(CH_2)_{\overline{q}}\text{--}D$$
$$\underset{Y}{|}\;\underset{Z}{\phantom{|}}$$

| Example | R¹ | R² | R³ | X | m | A | n | Y | Z | p | R⁶ | q | D | mp |
|---|---|---|---|---|---|---|---|---|---|---|---|---|---|---|
| | $C_6H_4$ | $C_6H_4$ | | | | | | | | | | | | |
| 60 | $C_6H_5$ | $C_6H_5$ | H | S | 3 | O | 3 | O | $NH\text{-}2\text{-}C_5H_4N$ | 4 | $CH_3$ | 2 | $NHC_6H_5$ | — |
| 61 | $C_6H_5$ | $C_6H_5$ | H | S | 2 | $CH_2$ | 2 | O | $NH\text{-}i\text{-}C_3H_7$ | 2 | $CH_3$ | 2 | $OCH_3$ | — |
| 62 | $C_6H_5$ | $C_6H_5$ | H | S | 2 | $CH_2$ | 2 | O | NH-2,4-$C_6H_3F_2$ | 2 | $CH_3$ | 2 | $OCH_3$ | — |
| 63 | $C_6H_5$ | $C_6H_5$ | H | S | 2 | $CH_2$ | 2 | O | $NHC_4H_9$ | 2 | $CH_3$ | 2 | $OCH_3$ | — |
| 64 | $C_6H_5$ | $C_6H_5$ | H | S | 2 | $CH_2$ | 2 | O | $OCH_2C_6H_5$ | 2 | $CH_3$ | 2 | $OCH_3$ | — |
| 65 | $C_6H_5$ | $C_6H_5$ | H | $SO_2$ | 2 | $CH_2$ | 2 | O | $NHCH_3$ | 2 | $CH_3$ | 2 | $OCH_3$ | — |
| 66 | $C_6H_5$ | $C_6H_5$ | H | NH | 2 | $CH_2$ | 2 | O | $NHCH_3$ | 2 | $CH_3$ | 2 | $OCH_3$ | — |
| 67 | $4\text{-}CH_3OC_6H_4$ | $4\text{-}CH_3OC_6H_4$ | H | S | 2 | $CH_2$ | 2 | O | $NH\text{-}i\text{-}C_3H_7$ | 2 | $CH_3$ | 2 | $OCH_3$ | — |
| 68 | $4\text{-}CH_3SC_6H_4$ | $4\text{-}CH_3SC_6H_4$ | H | S | 2 | $CH_2$ | 2 | O | $NH\text{-}i\text{-}C_3H_7$ | 2 | $CH_3$ | 3 | $OCH_3$ | — |
| 69 | $i\text{-}C_3H_7$ | $i\text{-}C_3H_7$ | H | S | 2 | $CH_2$ | 2 | O | $NH\text{-}i\text{-}C_3H_7$ | 2 | $CH_3$ | 2 | $OCH_3$ | — |
| 70 | $C_6H_5$ | $C_6H_5$ | H | S | 2 | O | 2 | O | $NH\text{-}i\text{-}C_3H_7$ | 2 | $CH_3$ | 2 | $OCH_3$ | — |
| 71 | $4\text{-}CH_3OC_6H_4$ | $4\text{-}CH_3OC_6H_4$ | H | S | 2 | O | 2 | O | $NH\text{-}i\text{-}C_3H_7$ | 2 | $CH_3$ | 2 | $OCH_3$ | — |
| 72 | $4\text{-}CH_3OC_6H_4$ | $4\text{-}CH_3OC_6H_4$ | H | S | 2 | O | 2 | O | NH-2,4-$C_6H_3F_2$ | 2 | $CH_3$ | 2 | $OCH_3$ | — |
| 73 | $4\text{-}CH_3OC_6H_4$ | $4\text{-}CH_3OC_6H_4$ | H | S | 2 | O | 2 | O | $CH_2C_6H_5$ | 2 | $CH_3$ | 2 | $OCH_3$ | — |
| 74 | $C_6H_5$ | H | H | S | 2 | $CH_2$ | 2 | O | $NH\text{-}i\text{-}C_3H_7$ | 2 | $CH_3$ | 3 | $OCH_3$ | — |
| 75 | $C_6H_5$ | $C_6H_5$ | $CH_3$ | S | 2 | $CH_2$ | 2 | O | $NH\text{-}i\text{-}C_3H_7$ | 2 | $CH_3$ | 2 | $OCH_3$ | — |
| 76 | $C_6H_5$ | $C_6H_5$ | H | S | 2 | $CH_2$ | 2 | O | $NH\text{-}i\text{-}C_3H_7$ | 2 | $CH_3$ | 2 | $OCH_3$ | — |
| 77 | $C_6H_5$ | $C_6H_5$ | H | S | 2 | S | 2 | O | $NH\text{-}i\text{-}C_3H_7$ | 2 | $CH_3$ | 2 | $OCH_3$ | — |
| 78 | $C_6H_5$ | $C_6H_5$ | H | $SO_2$ | 2 | $SO_2$ | 2 | O | $NH\text{-}i\text{-}C_3H_7$ | 2 | $CH_3$ | 2 | $OCH_3$ | — |
| 79 | $4\text{-}(CH_3)_2N\text{-}C_6H_4$ | $4\text{-}(CH_3)_2N\text{-}C_6H_4$ | H | S | 2 | $CH_2$ | 2 | O | $NH\text{-}i\text{-}C_3H_7$ | 2 | $CH_3$ | 2 | $OCH_3$ | — |
| 80 | $C_6H_5$ | $C_6H_5$ | H | S | 3 | O | 3 | O | $NH\text{-}2\text{-}C_5H_4N$ | 2 | $CH_3$ | 2 | $OCH_3$ | — |
| 81 | $i\text{-}C_3H_7$ | $4\text{-}CH_3OC_6H_4$ | H | S | 4 | $CH_2$ | 2 | S | $NHCH_2C_6H_5$ | 2 | $C_2H_5$ | 2 | H | — |
| 82 | $i\text{-}C_3H_7$ | $4\text{-}CH_3OC_6H_4$ | H | S | 4 | $CH_2$ | 2 | S | $NHCH_2C_6H_5$ | 2 | $CH_3$ | 4 | H | — |
| 83 | $i\text{-}C_3H_7$ | $4\text{-}CH_3OC_6H_4$ | H | S | 4 | $CH_2$ | 2 | S | $NHCH_2C_6H_5$ | 4 | $CH_3$ | 2 | $NHC_6H_5$ | — |
| 84 | $i\text{-}C_3H_7$ | $4\text{-}CH_3OC_6H_4$ | H | S | 4 | $CH_2$ | 2 | S | $NHCH_2C_6H_5$ | 2 | $CH_3$ | 2 | $OCH_3$ | — |
| 85 | $3\text{-}ClC_6H_4$ | $3\text{-}ClC_6H_4$ | $CH_3$ | $NCH_3$ | 2 | O | 4 | S | $C_6H_5$ | 2 | $C_2H_5$ | 2 | H | — |
| 86 | $3\text{-}ClC_6H_4$ | $3\text{-}ClC_6H_4$ | $CH_3$ | $NCH_3$ | 2 | O | 4 | S | $C_6H_5$ | 2 | $CH_3$ | 4 | H | — |
| 87 | $3\text{-}ClC_6H_4$ | $3\text{-}ClC_6H_4$ | $CH_3$ | $NCH_3$ | 2 | O | 4 | S | $C_6H_5$ | 4 | $CH_3$ | 2 | $NHC_6H_5$ | — |
| 88 | $3\text{-}ClC_6H_4$ | $3\text{-}ClC_6H_4$ | $CH_3$ | $NCH_3$ | 2 | O | 4 | S | $C_6H_5$ | 2 | $CH_3$ | 2 | $OCH_3$ | — |
| 89 | $C_6H_{11}$ | $C_6H_{11}$ | $C_6H_5$ | $CH_2$ | 4 | S | 4 | S | $NC_6H_5$ | 2 | $C_2H_5$ | 2 | H | — |
| 90 | $C_6H_{11}$ | $C_6H_{11}$ | $C_6H_5$ | $CH_2$ | 4 | S | 4 | S | $NC_6H_5$ | 2 | $CH_3$ | 4 | H | — |
| 91 | $C_6H_{11}$ | $C_6H_{11}$ | $C_6H_5$ | $CH_2$ | 4 | S | 4 | S | $NC_6H_5$ | 4 | $CH_3$ | 2 | $NHC_6H_5$ | — |
| 92 | $C_6H_{11}$ | $C_6H_{11}$ | $C_6H_5$ | $CH_2$ | 4 | S | 4 | S | $NC_6H_5$ | 2 | $CH_3$ | 2 | $OCH_3$ | — |
| 93 | 2-furanyl | 2-furanyl | H | S | 3 | O | 3 | $H_2$ | $CH_2CH(CH_3)_2$ | 2 | $C_2H_5$ | 2 | H | — |
| 94 | 2-furanyl | 2-furanyl | H | S | 3 | O | 3 | $H_2$ | $CH_2CH(CH_3)_2$ | 2 | $CH_3$ | 4 | H | — |
| 95 | 2-furanyl | 2-furanyl | H | S | 3 | O | 3 | $H_2$ | $CH_2CH(CH_3)_2$ | 4 | $CH_3$ | 2 | $NHC_6H_5$ | — |
| 96 | 2-furanyl | 2-furanyl | H | S | 3 | O | 3 | $H_2$ | $CH_2CH(CH_3)_2$ | 2 | $CH_3$ | 2 | $OCH_3$ | — |
| 97 | $C_6H_{11}C_2H_4$ | $C_6H_{11}C_2H_4$ | $CH_3$ | $NCH_3$ | 2 | $CH_2$ | 2 | $H_2$ | $C_7H_{15}$ | 2 | $C_2H_5$ | 2 | H | — |
| 98 | $C_6H_{11}C_2H_4$ | $C_6H_{11}C_2H_4$ | $CH_3$ | $NCH_3$ | 2 | $CH_2$ | 2 | $H_2$ | $C_7H_{15}$ | 2 | $CH_3$ | 4 | H | — |
| 99 | $C_6H_{11}C_2H_4$ | $C_6H_{11}C_2H_4$ | $CH_3$ | $NCH_3$ | 2 | $CH_2$ | 2 | $H_2$ | $C_7H_{15}$ | 4 | $CH_3$ | 2 | $NHC_6H_5$ | — |
| 100 | $C_6H_{11}C_2H_4$ | $C_6H_{11}C_2H_4$ | $CH_3$ | $NCH_3$ | 2 | $CH_2$ | 2 | $H_2$ | $C_7H_{15}$ | 2 | $CH_3$ | 2 | $OCH_3$ | — |

Footnotes to Table 1
[a] $^1$H NMR (CDCl$_3$): 7.64–7.55(1H, m); 7.54–7.23(4H, br s); 6.82(4H, d, J=8.4Hz); 6.72–6.63(1H, m); 6.62–6.55(1H, m); 3.80(6H, s); 3.79–3.70(4H, m); 3.60(2H, br t, J=4.8Hz); 3.49–3.40(2H, m); 3.12(2H, t, J=5.3Hz); 2.64(2H, br s); 2.45(2H, br t, J=7.7Hz); 2.33(3H, s); 1.52–1.40(2H, m); 1.33–1.21(2H, m); 0.86(3H, t, J=7.4Hz).

EXAMPLE 101

Preparation of
N'-(2,4-difluorophenyl)-N-[2-[2-(4,5-diphenyl-1H-imidazol-2-ylthio)ethyl]-N-[methylamino]ethyl]-N-heptyl-urea Part A Sarcosine (32.38 g, 363 mmol) was dissolved in 90 mL 4N aqueous sodium hydroxide, and cooled in an ice-salt bath to −5° C. The mixture was stirred vigorously and treated simultaneously with chloroacetyl chloride (32 mL, 402 mmol) and 110 mL 4N aqueous sodium hydroxide dropwise over 20 minutes. After warming to ambient temperature and stirring for 34 hours, the solution was carefully acidified to pH 2 (concentrated hydrochloric acid), saturated with sodium chloride, and extracted with ethyl acetate (2×400 mL). The extracts were combined, dried over anhydrous magnesium sulfate and evaporated to afford N-chloroacetylsarcosine as an oil, sufficiently pure for the next step (39.34 g, 238 mmol, 65%).

A portion of this material (6.45 g, 38.95 mmol) was dissolved in 100 mL dry tetrahydrofuran, and treated with 4,5-diphenyl-1H-imidazole-2-thiol (9.83 g, 38.96 mmol) and potassium carbonate (11.84 g, 85.67 mmol). The mixture was heated to reflux for 14 hours, cooled, and poured into water (200 mL). This aqueous phase was washed with ether, acidified to pH 5, saturated with sodium chloride, and extracted with ethyl acetate (3×200 mL). The extracts were combined, dried over anhydrous magnesium sulfate and evaporated to afford an off-white solid, which was N-[(4,5-diphenyl-1H-imidazol-2-ylthio)acetyl]sarcosine (13.00 g, 34.08 mmol, 87%).

The above-described acid (6.83 g, 17.91 mmol) was dissolved in 40 mL dimethylformamide, and treated with 1-hydroxy-1H-benzotriazole hydrate (3.14 g, 23.24 mmol). Then, a 20 mL dimethylformamide solution of heptyl amine (4.00 mL, 26.96 mmol) was added slowly. The reaction mixture was cooled to 0° C., and solid dicyclohexyl-carbodiimide (5.05 g, 24.48 mmol) was added portionwise over 10 minutes. The mixture was allowed to warm to ambient temperature, stirred for 60 hours, and poured into ethyl acetate (250 mL). This mixture was filtered, washed with water (3×250 mL) and brine (250 mL), dried over anhydrous magnesium sulfate and evaporated. The residue was separated by flash chromatography to afford N-[(4,5-diphenylimidazol-2-ylthio)acetyl]-N'-heptylsarcosinamide (6.56 g, 13.70 mmol, 77%).

This product was dissolved in 100 mL dry toluene, and added dropwise to a 50 mL toluene solution of Red-Al ™ (14 mL of 3.4M, 47.6 mmol). After stirring at ambient temperature overnight, an additional 15 mL of Red-Al ™ solution was added, and the mixture was refluxed for 15 h to complete the reaction. The mixture was quenched by the addition of 60 mL 1N aqueous sodium hydroxide at 0° C. and separated. The aqueous phase was saturated with sodium chloride and reextracted with methylene chloride (3×50 mL). The organic phases were combined, dried over anhydrous potassium carbonate, and evaporated. The resulting oily residue was separated by flash chromatography to afford pure N-[2-(heptylamino)-ethyl]-N-methyl-2-(4,5-diphenyl-1H-imidazol-2-ylthio)-ethanamine (2.05 g, 4.55 mmol, 33%). $^1$H NMR (300 MHz, CDCl$_3$): 7.51 (4H, d, J=7.4 Hz); 7.32–7.21 (7H, m); 3.07–3.04 (2H, m); 2.80–2.66 (6H, m); 2.58 (2H, t, J=7.3 Hz); 2.28 (3H, s); 1.43–1.35 (2H, m); 1.33–1.11 (8H, m); 0.83 (3H, t, J=7.0 Hz).

Part B

The above diamine (1.03 g, 22.7 mmol) was dissolved in 10 mL toluene, and cooled to 0° C. 2,4-difluorophenyl isocyanate (0.30 mL, 2.53 mmol) was added via syringe, and the mixture was allowed to warm to ambient temperature and stirred for 18 hours. The mixture was evaporated and separated by flash chromatography to afford the product, N'-(2,4-difluorophenyl)-N-(2-{2-(4,5-diphenyl-1H-imidazol-2-ylthio) ethyl]-N-methylamino}ethyl)-N-heptyl-urea, which was purified by recrystallization (1.27 g, 2.10 mmol, 92%), melting point: 151°–152° C. (toluene). $^1$H NMR (300 MHz, CDCl$_3$): 7.85–7.77 (1H, m); 7.57–7.46 (4H, m); 7.32–7.18 (7H, m); 6.80–6.72 (2H, m); 3.54–3.49 (2H, m); 3.30–3.22 (4H, m); 3.07–2.99 (2H, m); 2.95–2.88 (2H, m); 2.58 (3H, s); 1.58–1.54 (2H, m); 1.30–1.17(8H, m); 0.87 (3H, t, J=7.0 Hz). Elemental analysis: calculated C 67.41, H 6.82, N 11.56; found C 67.34, H 6.65, N 11.45.

Compounds 101–160 in Table 2 were prepared or could be prepared analogously by the procedures described in Examples 101 by employing the appropriately substituted starting materials. The compounds in Table 2 represent those analogues employing an amine nitrogen atom as a linking element in the chain between the imidazole group and the trisubstituted nitrogen atom.

TABLE 2

| Example | R$^1$ | R$^2$ | R$^3$ | X | m | R$^6$ | n | Y | Z | p | B | q | D | mp |
|---|---|---|---|---|---|---|---|---|---|---|---|---|---|---|
| 101 | C$_6$H$_5$ | C$_6$H$_5$ | H | S | 2 | CH$_3$ | 2 | O | NH-2,4-C$_6$H$_3$F$_2$ | 2 | CH$_2$ | 4 | H | 151–152 |
| 102 | C$_6$H$_5$ | C$_6$H$_5$ | H | S | 2 | CH$_3$ | 2 | O | NH-i-C$_3$H$_7$ | 2 | CH$_2$ | 4 | H | 122–124 |
| 103 | 4-CH$_3$OC$_6$H$_4$ | 4-CH$_3$OC$_6$H$_4$ | H | S | 2 | CH$_3$ | 2 | O | NH-i-C$_3$H$_7$ | 2 | CH$_2$ | 4 | H | — |
| 104 | 4-CH$_3$SC$_6$H$_4$ | 4-CH$_3$SC$_6$H$_4$ | H | S | 2 | CH$_3$ | 2 | O | NH-i-C$_3$H$_7$ | 2 | CH$_2$ | 4 | H | — |
| 105 | C$_6$H$_5$ | C$_6$H$_5$ | H | S | 2 | CH$_3$ | 2 | O | NH-i-C$_3$H$_7$ | 2 | CH$_2$ | 4 | H | — |
| 106 | C$_6$H$_5$ | C$_6$H$_5$ | CH$_3$ | S | 2 | CH$_3$ | 2 | O | NH-i-C$_3$H$_7$ | 2 | CH$_2$ | 4 | H | — |
| 107 | C$_6$H$_5$ | C$_6$H$_5$ | H | NCH$_3$ | 2 | CH$_3$ | 2 | O | NH-i-C$_3$H$_7$ | 2 | CH$_2$ | 4 | H | — |
| 108 | C$_6$H$_5$ | C$_6$H$_5$ | H | CH$_2$ | 2 | CH$_3$ | 2 | O | NH-i-C$_3$H$_7$ | 2 | CH$_2$ | 4 | H | — |
| 109 | C$_6$H$_5$ | C$_6$H$_5$ | H | S | 2 | CH$_3$ | 2 | S | NHC$_6$H$_5$ | 2 | CH$_2$ | 4 | H | — |
| 110 | C$_6$H$_5$ | C$_6$H$_5$ | H | SO$_2$ | 3 | CH$_3$ | 3 | O | OCH$_2$C$_6$H$_5$ | 2 | CH$_2$ | 4 | H | — |
| 111 | C$_6$H$_5$ | C$_6$H$_5$ | H | S | 2 | CH$_3$ | 2 | O | NH-2,4-C$_6$H$_3$F$_2$ | 2 | O | 2 | OCH$_3$ | — |
| 112 | C$_6$H$_5$ | C$_6$H$_5$ | H | S | 2 | CH$_3$ | 2 | O | NH-i-C$_3$H$_7$ | 2 | O | 2 | OCH$_3$ | — |
| 113 | 4-CH$_3$OC$_6$H$_4$ | 4-CH$_3$OC$_6$H$_4$ | H | S | 2 | CH$_3$ | 2 | O | NH-i-C$_3$H$_7$ | 2 | O | 2 | OCH$_3$ | — |
| 114 | 4-CH$_3$SC$_6$H$_4$ | 4-CH$_3$SC$_6$H$_4$ | H | S | 2 | CH$_3$ | 2 | O | NH-i-C$_3$H$_7$ | 2 | O | 2 | OCH$_3$ | — |
| 115 | C$_6$H$_5$ | C$_6$H$_5$ | H | S | 2 | CH$_3$ | 2 | O | NH-i-C$_3$H$_7$ | 2 | O | 2 | OCH$_3$ | — |
| 116 | C$_6$H$_5$ | C$_6$H$_5$ | CH$_3$ | S | 2 | CH$_3$ | 2 | O | NH-i-C$_3$H$_7$ | 2 | O | 2 | OCH$_3$ | — |
| 117 | C$_6$H$_5$ | C$_6$H$_5$ | H | NCH$_3$ | 2 | CH$_3$ | 2 | O | NH-i-C$_3$H$_7$ | 2 | O | 2 | OCH$_3$ | — |
| 118 | C$_6$H$_5$ | C$_6$H$_5$ | H | CH$_2$ | 2 | CH$_3$ | 2 | O | NH-i-C$_3$H$_7$ | 2 | O | 2 | OCH$_3$ | — |
| 119 | C$_6$H$_5$ | C$_6$H$_5$ | H | S | 2 | CH$_3$ | 2 | S | NHC$_6$H$_5$ | 2 | O | 2 | OCH$_3$ | — |
| 120 | C$_6$H$_5$ | C$_6$H$_5$ | H | SO$_2$ | 3 | CH$_3$ | 3 | O | OCH$_2$C$_6$H$_5$ | 2 | O | 2 | OCH$_3$ | — |
| 121 | C$_6$H$_5$ | C$_6$H$_5$ | H | S | 2 | CH$_3$ | 2 | O | NH-2,4-C$_6$H$_3$F$_2$ | 3 | S | 3 | H | — |
| 122 | C$_6$H$_5$ | C$_6$H$_5$ | H | S | 2 | CH$_3$ | 2 | O | NH-i-C$_3$H$_7$ | 3 | S | 3 | H | — |
| 123 | 4-CH$_3$OC$_6$H$_4$ | 4-CH$_3$OC$_6$H$_4$ | H | S | 2 | CH$_3$ | 2 | O | NH-i-C$_3$H$_7$ | 3 | S | 3 | H | — |
| 124 | 4-CH$_3$SC$_6$H$_4$ | 4-CH$_3$SC$_6$H$_4$ | H | S | 2 | CH$_3$ | 2 | O | NH-i-C$_3$H$_7$ | 3 | S | 3 | H | — |
| 125 | C$_6$H$_5$ | C$_6$H$_5$ | H | S | 2 | CH$_3$ | 2 | O | NH-i-C$_3$H$_7$ | 3 | S | 3 | H | — |
| 126 | C$_6$H$_5$ | C$_6$H$_5$ | CH$_3$ | S | 2 | CH$_3$ | 2 | O | NH-i-C$_3$H$_7$ | 3 | S | 3 | H | — |
| 127 | C$_6$H$_5$ | C$_6$H$_5$ | H | NCH$_3$ | 2 | CH$_3$ | 2 | O | NH-i-C$_3$H$_7$ | 3 | S | 3 | H | — |
| 128 | C$_6$H$_5$ | C$_6$H$_5$ | H | CH$_2$ | 2 | CH$_3$ | 2 | O | NH-i-C$_3$H$_7$ | 3 | S | 3 | H | — |
| 129 | C$_6$H$_5$ | C$_6$H$_5$ | H | S | 2 | CH$_3$ | 2 | S | NHC$_6$H$_5$ | 3 | S | 3 | H | — |
| 130 | C$_6$H$_5$ | C$_6$H$_5$ | H | SO$_2$ | 3 | CH$_3$ | 3 | O | OCH$_2$C$_6$H$_5$ | 3 | S | 3 | H | — |
| 131 | C$_6$H$_5$ | C$_6$H$_5$ | H | S | 2 | C$_4$H$_9$ | 2 | O | NH-2,4-C$_6$H$_3$F$_2$ | 2 | CH$_2$ | 4 | H | — |
| 132 | C$_6$H$_5$ | C$_6$H$_5$ | H | S | 2 | C$_4$H$_9$ | 2 | O | NH-i-C$_3$H$_7$ | 2 | O | 2 | OCH$_3$ | — |

TABLE 2-continued $$R^1, R^2 \text{ (imidazole with } N-R^3\text{)} - X-(CH_2)_{\overline{m}}N(R^6)-(CH_2)_{\overline{n}}-N(Y=Z)-(CH_2)_{\overline{p}}-B-(CH_2)_{\overline{q}}-D$$

| Example | R¹ | R² | R³ | X | m | R⁶ | n | Y | Z | p | B | q | D | mp |
|---|---|---|---|---|---|---|---|---|---|---|---|---|---|---|
| 133 | 4-CH₃OC₆H₄ | 4-CH₃OC₆H₄ | H | S | 2 | C₄H₉ | 2 | O | NH-i-C₃H₇ | 3 | S | 3 | H | — |
| 134 | 4-CH₃SC₆H₄ | 4-CH₃SC₆H₄ | H | S | 2 | C₄H₉ | 2 | O | NH-i-C₃H₇ | 2 | CH₂ | 4 | H | — |
| 135 | C₆H₅ | C₆H₅ | H | S | 2 | C₄H₉ | 2 | O | NH-i-C₃H₇ | 2 | O | 2 | OCH₃ | — |
| 136 | C₆H₅ | C₆H₅ | CH₃ | S | 2 | C₄H₉ | 2 | O | NH-i-C₃H₇ | 3 | S | 3 | H | — |
| 137 | C₆H₅ | C₆H₅ | H | NCH₃ | 2 | C₄H₉ | 2 | O | NH-i-C₃H₇ | 2 | CH₂ | 4 | H | — |
| 138 | C₆H₅ | C₆H₅ | H | CH₂ | 2 | C₄H₉ | 2 | O | NH-i-C₃H₇ | 2 | O | 2 | OCH₃ | — |
| 139 | C₆H₅ | C₆H₅ | H | S | 2 | C₄H₉ | 2 | S | NHC₆H₅ | 3 | S | 3 | H | — |
| 140 | C₆H₅ | C₆H₅ | H | SO₂ | 3 | C₄H₉ | 3 | O | OCH₂C₆H₅ | 2 | CH₂ | 4 | H | — |
| 141 | i-C₃H₇ | 4-CH₃OC₆H₄ | H | S | 4 | C₂H₅ | 2 | S | NHCH₂C₆H₅ | 2 | CH₂ | 4 | H | — |
| 142 | i-C₃H₇ | 4-CH₃OC₆H₄ | H | S | 4 | CH₃ | 2 | S | NHCH₂C₆H₅ | 2 | O | 2 | OCH₃ | — |
| 143 | i-C₃H₇ | 4-CH₃OC₆H₄ | H | S | 4 | C₄H₉ | 2 | S | NHCH₂C₆H₅ | 3 | S | 3 | H | — |
| 144 | i-C₃H₇ | 4-CH₃OC₆H₄ | H | S | 4 | C₃H₇ | 2 | S | NHCH₂C₆H₅ | 4 | CH₂ | 4 | OC₃H₇ | — |
| 145 | 3-ClC₆H₄ | 3-ClC₆H₄ | CH₃ | NCH₃ | 2 | C₂H₅ | 4 | S | C₆H₅ | 2 | CH₂ | 4 | H | — |
| 146 | 3-ClC₆H₄ | 3-ClC₆H₄ | CH₃ | NCH₃ | 2 | CH₃ | 4 | S | C₆H₅ | 2 | O | 2 | OCH₃ | — |
| 147 | 3-ClC₆H₄ | 3-ClC₆H₄ | CH₃ | NCH₃ | 2 | C₄H₉ | 4 | S | C₆H₅ | 3 | S | 3 | H | — |
| 148 | 3-ClC₆H₄ | 3-ClC₆H₄ | CH₃ | NCH₃ | 2 | C₃H₇ | 4 | S | C₆H₅ | 4 | CH₂ | 4 | OC₃H₇ | — |
| 149 | C₆H₁₁ | C₆H₁₁ | C₆H₅ | CH₂ | 4 | C₂H₅ | 4 | S | NC₆H₅ | 2 | CH₂ | 4 | H | — |
| 150 | C₆H₁₁ | C₆H₁₁ | C₆H₅ | CH₂ | 4 | CH₃ | 4 | S | NC₆H₅ | 2 | O | 2 | OCH₃ | — |
| 151 | C₆H₁₁ | C₆H₁₁ | C₆H₅ | CH₂ | 4 | C₄H₉ | 4 | S | NC₆H₅ | 3 | S | 3 | H | — |
| 152 | C₆H₁₁ | C₆H₁₁ | C₆H₅ | CH₂ | 4 | C₃H₇ | 4 | S | NC₆H₅ | 4 | CH₂ | 4 | OC₃H₇ | — |
| 153 | 2-furanyl | 2-furanyl | H | S | 3 | C₂H₅ | 3 | H₂ | CH₂CH(CH₃)₂ | 2 | CH₂ | 4 | H | — |
| 154 | 2-furanyl | 2-furanyl | H | S | 3 | CH₃ | 3 | H₂ | CH₂CH(CH₃)₂ | 2 | O | 2 | OCH₃ | — |
| 155 | 2-furanyl | 2-furanyl | H | S | 3 | C₄H₉ | 3 | H₂ | CH₂CH(CH₃)₂ | 3 | S | 3 | H | — |
| 156 | 2-furanyl | 2-furanyl | H | S | 3 | C₃H₇ | 3 | H₂ | CH₂CH(CH₃)₂ | 4 | CH₂ | 4 | OC₃H₇ | — |
| 157 | C₆H₁₁C₂H₄ | C₆H₁₁C₂H₄ | CH₃ | NCH₃ | 2 | C₂H₅ | 2 | H₂ | C₇H₁₅ | 2 | CH₂ | 4 | H | — |
| 158 | C₆H₁₁C₂H₄ | C₆H₁₁C₂H₄ | CH₃ | NCH₃ | 2 | CH₃ | 2 | H₂ | C₇H₁₅ | 2 | O | 2 | OCH₃ | — |
| 159 | C₆H₁₁C₂H₄ | C₆H₁₁C₂H₄ | CH₃ | NCH₃ | 2 | C₄H₉ | 2 | H₂ | C₇H₁₅ | 3 | S | 3 | H | — |
| 160 | C₆H₁₁C₂H₄ | C₆H₁₁C₂H₄ | CH₃ | NCH₃ | 2 | C₃H₇ | 2 | H₂ | C₇H₁₅ | 4 | CH₂ | 4 | OC₃H₇ | — |

EXAMPLE 162

Preparation of N-[5-[4,5-bis(4-methoxyphenyl)-1H-imidazol-2-ylthio]-pentyl]-N'-(2,4-difluorophenyl)-N-[2-(1-morpholinyl)ethyl]-urea Part A A solution of 5-[4,5-bis(4-methoxyphenyl)-1H-imidazol-2-ylthio]pentanoic acid (1.91 g, 4.63 mmol) and 1-hydroxy-1H-benzotriazole hydrate (890 rag, 6.59 mmol) in tetrahydrofuran (20 mL) was cooled to 0° C., and treated with 2-aminoethylmorpholine (1.0 mL, 7.62 mmol). After 20 minutes, dicyclohexylcarbodiimide (1.42 g, 6.88 mmol) was added in small portions over 20 minutes. This mixture was allowed to stir an additional 48 hours, then poured into ethyl acetate (250 mL), filtered, and washed with water (200 mL). The phases were separated, and the aqueous phase was saturated with sodium chloride and reextracted with methylene chloride (200 mL). The organic phases were combined, dried over anhydrous sodium sulfate and evaporated. The mixture was separated by flash chromatography to afford the product, N-(2-morpholinyl-ethyl)-5-[4,5-bis(4-methoxyphenyl)-1H-imidazol-2-ylthio]-pentanamide, as an oil (1.77 g, 3.37 mmol, 73%). ¹H NMR (CDCl₃): 7.42 (4H, br d, J=9 Hz); 6.82 (4H, d, J=9 Hz); 6.22 (1H, br t, J=4 Hz); 3.80 (6H, s); 3.65–3.60 (4H, m); 3.15 (2H, q, J=6 Hz); 2.98 (2H, t, J=7 Hz); 2.38–2.24 (8H, m); 1.96–1.85 (2H, m); 1.70–1.60 (2H, m).

Part B

A solution of the amide prepared above in anhydrous tetrahydrofuran (20 mL) was cooled to 0° C., and treated with a solution of sodium bis(methoxyethoxy) aluminum hydride in toluene (2.2 mL, 3.4M, 7.48 mmol) via syringe. The ice bath was removed, and the reaction mixture was heated to reflux for 18 hours, then cooled back down to 0° C. and quenched by careful addition of 2M aqueous sodium hydroxide (4 mL). The mixture was poured into water (100 mL), and extracted with methylene chloride (100 mL). The aqueous phase was saturated with sodium chloride, and reextracted with methylene chloride (100 mL). The organic extracts were combined, dried over anhydrous potassium carbonate and evaporated.

The crude amine thus obtained was dissolved in methylene chloride (20 mL), cooled to 0° C., and treated with 2,4-difluorophenylisocyanate (0.50 mL, 4.22 mmol). After stirring for 18 hours, the solution was evaporated, and the oily residue separated by flash chromatography (1:1 acetone-hexane) to afford the product, N-[5-[4,5-bis(4-methoxyphenyl)-1H-imidazol-2-ylthio]pentyl]-N'-(2,4-difluorophenyl)-N-[2-(1-morpholinyl)ethyl]-urea, as a low-melting solid. ¹H NMR (CDCl₃): 9.68 (1H, s); 7.52–7.26 (5H, m); 6.79 (4H, d, J=8.8 Hz); 6.73–6.55 (2H, m); 3.79 (6H, s); 3.75–3.67

(4H, m); 3.42 (4H, br s); 2.93 (2H, t, J=6.4 Hz); 2.64–2.58 (6H, m); 1.80–1.44 (6H, m). Elemental analysis: calculated C 63.14, H 6.21, N 10.52; C 62.81, H 6.24, N 10.23.

EXAMPLE 181

Preparation of
N-[2-[2-(N-(4,5-bis(4-methoxyphenyl)-1H-imidazol-2-ylthio)-ethyl )-N-methyl-amino]-ethyl]-N'-(2,4-diflurophenyl )-N-[2-(1-morpholinyl)-ethyl]-urea Part A A solution of N-[(4,5-diphenyl-1H-imidazol-2-ylthio)acetyl]-sarcosine (see Example 81, Part A, above) (4.08 g, 10.7 mmol) in tetrahydrofuran (30 mL) was treated with 1-hydroxy-1H-benzotriazole hydrate (1.78 g, 13.2 mmol) in one portion. The solution was cooled to 0° C., and treated first with 1-(2-aminoethyl)-morpholine (2.00 mL, 15.2 mmol), then with dicyclohexylcarbodiimide (3.02 g, 14.7 mmol). The mixture was stirred for 18 hours, then poured into 200 mL ethyl acetate and filtered. The filtrate was washed with water, dried over anhydrous sodium sulfate, and evaporated. The residual oil was separated by flash chromatography (1:19 methanol-methylene chloride) to afford the product, N-[2-(4,5-diphenyl-1H-imidazol-2-ylthio)-acetyl]-N'-[2-(1-morpholinyl)-ethyl]-sarcosine (2.69 g, 5.45 mmol, 51%). $^1$H NMR spectrum complex; mass spectrum (NH$_3$-CI/DDIP): m/e 495 (M+H$^+$+i, 30%), 494 (M+H$^+$, 100%).

Part B

The product from Part A above was dissolved in anhydrous tetrahydrofuran (20 mL). This solution was added dropwise to an ice-cooled solution of sodium bis(methoxyethoxy) aluminum hydride (27.2 mmol) in toluene (36 mL). The ice bath was removed, and the mixture was heated to reflux for 18 hours. After being cooled to 0° C., the mixture was quenched with the slow addition of 2N aqueous sodium hydroxide (4 mL). This mixture was partitioned between water and methylene chloride (100 mL each), and separated. The aqueous phase was adjusted to pH 5 with 6N aqueous hydrochloric acid, saturated with sodium chloride, and reextracted with methylene chloride (100 mL). The organic phases were combined, dried over anhydrous potassium carbonate, and evaporated.

A portion of the crude triamine product obtained above (ca. 2.77 mmol) was dissolved in methylene chloride (20 mL), cooled to 0° C., and treated with a solution of 2,4-difluorophenylisocyanate (0.35 mL, 2.95 mmol) in methylene chloride (10 mL). This solution was stirred for 40 hours, then evaporated. The residual oily product was purified by flash chromatography (1:3 acetone-hexane) to afford N-[2-[2-(N-(4,5-bis(4-methoxyphenyl)-1H-imidazol-2-ylthio)-ethyl)-N-methyl-amino]-ethyl]-N'-(2,4-difluorophenyl)-N-[2-(1-morpholinyl)-ethyl]-urea (910 rag, 1.47 mmol, 54% overall). $^1$H NMR (CDCl$_3$): 9.95 (1H, br s); 7.60–7.20 (11H, m); 6.76–6.62 (3H, m); 3.64 (4H, t, J=4.6 Hz); 3.47 (2H, t, J=5.9 Hz); 3.39 (2H, t, J=5.4 Hz); 3.14 (2H, t, J=5.7 Hz); 2.85 (2H, t, J=5.9 Hz); 2.71 (2H, t, J=5.7 Hz); 2.56 (2H, t, J=5.4 Hz); 2.55–2.45 (4H, m); 2.39 (3H, s). Elemental analysis: calculated C 63.85, H 6.17, N 13.54; found C 63.74, H 6.18, N 13.49.

Compounds 161–260 in Table 3 were prepared or could be prepared analogously by the procedures described in Example 162 and 181 by employing the appropriately substituted starting materials. The compounds in Table 3 represent those analogues bearing a cyclic alkylamino group on the trisubstituted nitrogen atom.

TABLE 3

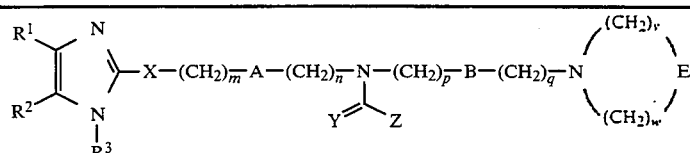

| Ex. | R$^1$ | R$^2$ | R$^3$ | X | m | A | n | Y | Z | p | B | q | v | w | E | mp |
|---|---|---|---|---|---|---|---|---|---|---|---|---|---|---|---|---|
| 161 | C$_6$H$_5$ | C$_6$H$_5$ | H | S | 2 | CH$_2$ | 2 | O | NH-2,4-C$_6$H$_3$F$_2$ | 0 | CH$_2$ | 1 | 2 | 2 | O | 70–72 |
| 162 | 4-CH$_3$OC$_6$H$_4$ | 4-CH$_3$OC$_6$H$_4$ | H | S | 2 | CH$_2$ | 2 | O | NH-2,4-C$_6$H$_3$F$_2$ | 0 | CH$_2$ | 1 | 2 | 2 | O | oil$^a$ |
| 163 | C$_6$H$_5$ | C$_6$H$_5$ | H | S | 2 | CH$_2$ | 2 | O | NH-i-C$_3$H$_7$ | 0 | CH$_2$ | 1 | 2 | 2 | O | — |
| 164 | C$_6$H$_5$ | C$_6$H$_5$ | H | S | 2 | CH$_2$ | 2 | O | OCH$_2$C$_6$H$_5$ | 0 | CH$_2$ | 1 | 2 | 2 | O | — |
| 165 | 4-(CH$_3$)$_2$NC$_6$H$_4$ | 4-(CH$_3$)$_2$NC$_6$H$_4$ | H | S | 2 | CH$_2$ | 2 | O | NH-i-C$_3$H$_7$ | 0 | CH$_2$ | 1 | 2 | 2 | O | — |
| 166 | C$_6$H$_5$ | C$_6$H$_5$ | CH$_3$ | NCH$_3$ | 2 | CH$_2$ | 2 | S | (CH$_2$)$_3$CH$_3$ | 0 | CH$_2$ | 1 | 2 | 2 | O | — |
| 167 | C$_6$H$_5$ | C$_6$H$_5$ | H | S | 3 | CH$_2$ | 3 | O | NH-i-C$_3$H$_7$ | 0 | CH$_2$ | 1 | 2 | 2 | O | — |
| 168 | C$_6$H$_5$ | C$_6$H$_5$ | H | S | 2 | CH$_2$ | 2 | O | NH-i-C$_3$H$_7$ | 2 | O | 2 | 2 | 2 | O | — |
| 169 | C$_6$H$_5$ | C$_6$H$_5$ | H | S | 2 | CH$_2$ | 2 | O | NH-i-C$_3$H$_7$ | 2 | NCH$_3$ | 2 | 2 | 2 | O | — |
| 170 | 4-CH$_3$OC$_6$H$_4$ | 4-CH$_3$OC$_6$H$_4$ | H | S | 2 | CH$_2$ | 2 | O | NH-i-C$_3$H$_7$ | 0 | CH$_2$ | 1 | 2 | 2 | NCH$_3$ | — |
| 171 | 4-CH$_3$OC$_6$H$_4$ | 4-CH$_3$OC$_6$H$_4$ | H | S | 2 | CH$_2$ | 2 | O | NH-i-C$_3$H$_7$ | 2 | CH$_2$ | 1 | 2 | 2 | O | — |
| 172 | 4-CH$_3$OC$_6$H$_4$ | 4-CH$_3$OC$_6$H$_4$ | H | S | 2 | CH$_2$ | 2 | O | NHCH$_2$C$_6$H$_5$ | 0 | CH$_2$ | 1 | 2 | 1 | CH$_2$ | — |
| 173 | 4-CH$_3$OC$_6$H$_4$ | 4-CH$_3$OC$_6$H$_4$ | H | S | 2 | CH$_2$ | 2 | O | CH$_2$C$_6$H$_5$ | 0 | CH$_2$ | 1 | 2 | 3 | CH$_2$ | — |
| 174 | 4-CH$_3$OC$_6$H$_4$ | 4-CH$_3$OC$_6$H$_4$ | H | S | 2 | CH$_2$ | 2 | O | NH-i-C$_3$H$_7$ | 0 | CH$_2$ | 1 | 2 | 2 | CO | — |
| 175 | 4-CH$_3$OC$_6$H$_4$ | 4-CH$_3$OC$_6$H$_4$ | H | S | 2 | CH$_2$ | 2 | O | NH-2-C$_5$H$_4$N | 0 | CH$_2$ | 1 | 2 | 2 | CO | — |
| 176 | 4-CH$_3$OC$_6$H$_4$ | 4-CH$_3$OC$_6$H$_4$ | H | S | 2 | CH$_2$ | 2 | O | NH-i-C$_3$H$_7$ | 0 | CH$_2$ | 1 | 3 | 0 | CO | — |
| 177 | 4-CH$_3$OC$_6$H$_4$ | 4-CH$_3$OC$_6$H$_4$ | H | S | 2 | CH$_2$ | 2 | O | NH-i-C$_3$H$_7$ | 0 | CH$_2$ | 1 | 2 | 1 | C(=O)NCH$_3$ | — |
| 178 | 4-CH$_3$OC$_6$H$_4$ | 4-CH$_3$OC$_6$H$_4$ | H | S | 2 | CH$_2$ | 2 | O | NH-2,4-C$_6$H$_3$F$_2$ | 0 | CH$_2$ | 1 | 2 | 1 | C(=O)O | — |

TABLE 3-continued

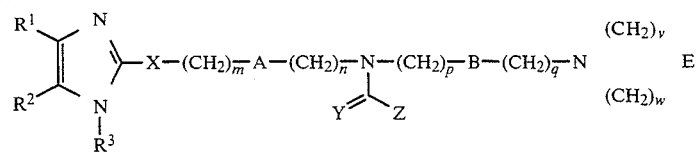

| Ex. | R¹ | R² | R³ | X | m | A | n | Y | Z | p | B | q | v | w | E | mp |
|---|---|---|---|---|---|---|---|---|---|---|---|---|---|---|---|---|
| 179 | 4-CH$_3$OC$_6$H$_4$ | 4-CH$_3$OC$_6$H$_4$ | H | S | 2 | CH$_2$ | 2 | O | NHCH$_3$ | 2 | CH$_2$ | 2 | 2 | 2 | C=O | — |
| 180 | 4-CH$_3$OC$_6$H$_4$ | 4-CH$_3$OC$_6$H$_4$ | H | S | 2 | CH$_2$ | 2 | O | NH-4-CH$_3$S—C$_6$H$_4$ | 2 | NCH$_3$ | 2 | 2 | 1 | C(=O)O | — |
| 181 | C$_6$H$_5$ | C$_6$H$_5$ | H | S | 2 | NCH$_3$ | 2 | O | NH-2,4-C$_6$H$_3$F$_2$ | 0 | CH$_2$ | 1 | 2 | 2 | O | oil[b] |
| 182 | 4-CH$_3$OC$_6$H$_4$ | 4-CH$_3$OC$_6$H$_4$ | H | S | 2 | NCH$_3$ | 2 | O | NH-2,4-C$_6$H$_3$F$_2$ | 0 | CH$_2$ | 1 | 2 | 2 | O | — |
| 183 | C$_6$H$_5$ | C$_6$H$_5$ | H | S | 2 | NCH$_3$ | 2 | O | NH-i-C$_3$H$_7$ | 0 | CH$_2$ | 1 | 2 | 2 | O | oil[c] |
| 184 | C$_6$H$_5$ | C$_6$H$_5$ | H | S | 2 | NCH$_3$ | 2 | O | OCH$_2$C$_6$H$_5$ | 0 | CH$_2$ | 1 | 2 | 2 | O | — |
| 185 | 4-(CH$_3$)$_2$NC$_6$H$_4$ | 4-(CH$_3$)$_2$NC$_6$H$_4$ | H | S | 2 | NCH$_3$ | 2 | O | NH-i-C$_3$H$_7$ | 0 | CH$_2$ | 1 | 2 | 2 | O | — |
| 186 | C$_6$H$_5$ | C$_6$H$_5$ | CH$_3$ | NCH$_3$ | 2 | NCH$_3$ | 2 | S | (CH$_2$)$_3$CH$_3$ | 0 | CH$_2$ | 1 | 2 | 2 | 0 | — |
| 187 | C$_6$H$_5$ | C$_6$H$_5$ | H | S | 3 | NCH$_3$ | 3 | O | NH-i-C$_3$H$_7$ | 0 | CH$_2$ | 1 | 2 | 2 | O | — |
| 188 | C$_6$H$_5$ | C$_6$H$_5$ | H | S | 2 | NCH$_3$ | 2 | O | NH-i-C$_3$H$_7$ | 2 | O | 2 | 2 | 2 | O | — |
| 189 | C$_6$H$_5$ | C$_6$H$_5$ | H | S | 2 | NCH$_3$ | 2 | O | NH-i-C$_3$H$_7$ | 2 | NCH$_3$ | 2 | 2 | 2 | O | — |
| 190 | 4-CH$_3$OC$_6$H$_4$ | 4-CH$_3$OC$_6$H$_4$ | H | S | 2 | NCH$_3$ | 2 | O | NH-i-C$_3$H$_7$ | 0 | CH$_2$ | 1 | 2 | 2 | NCH$_3$ | — |
| 191 | 4-CH$_3$OC$_6$H$_4$ | 4-CH$_3$OC$_6$H$_4$ | H | S | 2 | NCH$_3$ | 2 | O | NH-i-C$_3$H$_7$ | 2 | CH$_2$ | 1 | 2 | 2 | O | — |
| 192 | 4-CH$_3$OC$_6$H$_4$ | 4-CH$_3$OC$_6$H$_4$ | H | S | 2 | NCH$_3$ | 2 | O | NHCH$_2$C$_6$H$_5$ | 0 | CH$_2$ | 1 | 2 | 1 | CH$_2$ | — |
| 193 | 4-CH$_3$OC$_6$H$_4$ | 4-CH$_3$OC$_6$H$_4$ | H | S | 2 | NCH$_3$ | 2 | O | CH$_2$C$_6$H$_5$ | 0 | CH$_2$ | 1 | 2 | 3 | CH$_3$ | — |
| 194 | 4-CH$_3$OC$_6$H$_4$ | 4-CH$_3$OC$_6$H$_4$ | H | S | 2 | NCH$_3$ | 2 | O | NH-i-C$_3$H$_7$ | 0 | CH$_2$ | 1 | 2 | 2 | CO | — |
| 195 | 4-CH$_3$OC$_6$H$_4$ | 4-CH$_3$OC$_6$H$_4$ | H | S | 2 | NCH$_3$ | 2 | O | NH-2-C$_5$H$_4$ | 0 | CH$_2$ | 1 | 2 | 2 | CO | — |
| 196 | 4-CH$_3$OC$_6$H$_4$ | 4-CH$_3$OC$_6$H$_4$ | H | S | 2 | NCH$_3$ | 2 | O | NH-i-C$_3$H$_7$ | 0 | CH$_2$ | 1 | 3 | 0 | CO | — |
| 197 | 4-CH$_3$OC$_6$H$_4$ | 4-CH$_3$OC$_6$H$_4$ | H | S | 2 | NCH$_3$ | 2 | O | NH-i-C$_3$H$_7$ | 0 | CH$_2$ | 1 | 2 | 1 | C(=O)NCH$_3$ | — |
| 198 | 4-CH$_3$OC$_6$H$_4$ | 4-CH$_3$OC$_6$H$_4$ | H | S | 2 | NCH$_3$ | 2 | O | NH-2,4-C$_6$H$_3$F$_2$ | 0 | CH$_2$ | 1 | 2 | 1 | C(=O)O | — |
| 199 | 4-CH$_3$OC$_6$H$_4$ | 4-CH$_3$OC$_6$H$_4$ | H | S | 2 | NCH$_3$ | 2 | O | NHCH$_3$ | 2 | CH$_2$ | 2 | 2 | 2 | C=O | — |
| 200 | 4-CH$_3$OC$_6$H$_4$ | 4-CH$_3$OC$_6$H$_4$ | H | S | 2 | NCH$_3$ | 2 | O | NH-4-CH$_3$S—C$_6$H$_4$ | 2 | NCH$_3$ | 2 | 2 | 1 | C(=O)O | — |
| 201 | C$_6$H$_5$ | C$_6$H$_5$ | H | S | 2 | O | 2 | O | NH-2,4-C$_6$H$_3$F$_2$ | 0 | CH$_2$ | 1 | 2 | 2 | O | — |
| 202 | 4-CH$_3$OC$_6$H$_4$ | 4-CH$_3$OC$_6$H$_4$ | H | S | 2 | O | 2 | O | NH-2,4-C$_6$H$_3$F$_2$ | 0 | CH$_2$ | 1 | 2 | 2 | O | — |
| 203 | C$_6$H$_5$ | C$_6$H$_5$ | H | S | 2 | O | 2 | O | NH-i-C$_3$H$_7$ | 0 | CH$_2$ | 1 | 2 | 2 | O | — |
| 204 | C$_6$H$_5$ | C$_6$H$_5$ | H | S | 2 | O | 2 | O | OCH$_2$C$_6$H$_5$ | 0 | CH$_2$ | 1 | 2 | 2 | O | — |
| 205 | 4-(CH$_3$)$_2$NC$_6$H$_4$ | 4-(CH$_3$)$_2$NC$_6$H$_4$ | H | S | 2 | O | 2 | O | NH-i-C$_3$H$_7$ | 0 | CH$_2$ | 1 | 2 | 2 | O | — |
| 206 | C$_6$H$_5$ | C$_6$H$_5$ | CH$_3$ | NCH$_3$ | 2 | O | 2 | S | (CH$_2$)$_3$CH$_3$ | 0 | CH$_2$ | 1 | 2 | 2 | O | — |
| 207 | C$_6$H$_5$ | C$_6$H$_5$ | H | S | 3 | O | 3 | O | NH-i-C$_3$H$_7$ | 0 | CH$_2$ | 1 | 2 | 2 | O | — |
| 208 | C$_6$H$_5$ | C$_6$H$_5$ | H | S | 2 | O | 2 | O | NH-i-C$_3$H$_7$ | 2 | O | 2 | 2 | 2 | O | — |
| 209 | C$_6$H$_5$ | C$_6$H$_5$ | H | S | 2 | O | 2 | O | NH-i-C$_3$H$_7$ | 2 | NCH$_3$ | 2 | 2 | 2 | O | — |
| 210 | 4-CH$_3$OC$_6$H$_4$ | 4-CH$_3$OC$_6$H$_4$ | H | S | 2 | O | 2 | O | NH-i-C$_3$H$_7$ | 0 | CH$_2$ | 1 | 2 | 2 | NCH$_3$ | — |
| 211 | 4-CH$_3$OC$_6$H$_4$ | 4-CH$_3$OC$_6$H$_4$ | H | S | 2 | O | 2 | O | NH-i-C$_3$H$_7$ | 2 | CH$_2$ | 1 | 2 | 2 | O | — |
| 212 | 4-CH$_3$OC$_6$H$_4$ | 4-CH$_3$OC$_6$H$_4$ | H | S | 2 | O | 2 | O | NHCH$_2$C$_6$H$_5$ | 0 | CH$_2$ | 1 | 2 | 1 | CH$_2$ | — |
| 213 | 4-CH$_3$OC$_6$H$_4$ | 4-CH$_3$OC$_6$H$_4$ | H | S | 2 | O | 2 | O | CH$_2$C$_6$H$_5$ | 0 | CH$_2$ | 1 | 2 | 3 | CH$_2$ | — |
| 214 | 4-CH$_3$OC$_6$H$_4$ | 4-CH$_3$OC$_6$H$_4$ | H | S | 2 | O | 2 | O | NH-i-C$_3$H$_7$ | 0 | CH$_2$ | 1 | 2 | 2 | CO | — |
| 215 | 4-CH$_3$OC$_6$H$_4$ | 4-CH$_3$OC$_6$H$_4$ | H | S | 2 | O | 2 | O | NH-2-C$_5$H$_4$N | 0 | CH$_2$ | 1 | 2 | 2 | CO | — |
| 216 | 4-CH$_3$OC$_6$H$_4$ | 4-CH$_3$OC$_6$H$_4$ | H | S | 2 | O | 2 | O | NH-i-C$_3$H$_7$ | 0 | CH$_2$ | 1 | 3 | 0 | CO | — |
| 217 | 4-CH$_3$OC$_6$H$_4$ | 4-CH$_3$OC$_6$H$_4$ | H | S | 2 | O | 2 | O | NH-i-C$_3$H$_7$ | 0 | CH$_2$ | 1 | 2 | 1 | C(=O)NCH$_3$ | — |
| 218 | 4-CH$_3$OC$_6$H$_4$ | 4-CH$_3$OC$_6$H$_4$ | H | S | 2 | O | 2 | O | NH-2,4-C$_6$H$_3$F$_2$ | 0 | CH$_2$ | 1 | 2 | 1 | C(=O)O | — |
| 219 | 4-CH$_3$OC$_6$H$_4$ | 4-CH$_3$OC$_6$H$_4$ | H | S | 2 | O | 2 | O | NHCH$_3$ | 2 | CH$_2$ | 2 | 2 | 2 | C=O | — |
| 220 | 4-CH$_3$OC$_6$H$_4$ | 4-CH$_3$OC$_6$H$_4$ | H | S | 2 | O | 2 | O | NH-4-CH$_3$S—C$_6$H$_4$ | 2 | NCH$_3$ | 2 | 2 | 1 | C(=O)O | — |
| 221 | C$_6$H$_5$ | C$_6$H$_5$ | H | S | 2 | S | 2 | O | NH-2,4-C$_6$H$_3$F$_2$ | 0 | CH$_2$ | 1 | 2 | 2 | O | — |
| 222 | 4-CH$_3$OC$_6$H$_4$ | 4-CH$_3$OC$_6$H$_4$ | H | S | 2 | S | 2 | O | NH-2,4-C$_6$H$_3$F$_2$ | 0 | CH$_2$ | 1 | 2 | 2 | O | — |

TABLE 3-continued $$R^1, R^2\text{-N(R}^3\text{)-imidazole} =N-X-(CH_2)_m-A-(CH_2)_n-N(Y-Z)-(CH_2)_p-B-(CH_2)_q-N[(CH_2)_v, (CH_2)_w]E$$

| Ex. | $R^1$ | $R^2$ | $R^3$ | X | m | A | n | Y | Z | p | B | q | v | w | E | mp |
|---|---|---|---|---|---|---|---|---|---|---|---|---|---|---|---|---|
| 223 | $C_6H_5$ | $C_6H_5$ | H | S | 2 | S | 2 | O | NH-i-$C_3H_7$ | 0 | $CH_2$ | 1 | 2 | 2 | O | — |
| 224 | $C_6H_5$ | $C_6H_5$ | H | S | 2 | S | 2 | O | $OCH_2C_6H_5$ | 0 | $CH_2$ | 1 | 2 | 2 | O | — |
| 225 | 4-$(CH_3)_2NC_6H_4$ | 4-$(CH_3)_2NC_6H_4$ | H | S | 2 | S | 2 | O | NH-i-$C_3H_7$ | 0 | $CH_2$ | 1 | 2 | 2 | O | — |
| 226 | $C_6H_5$ | $C_6H_5$ | $CH_3$ | $NCH_3$ | 2 | S | 2 | S | $(CH_2)_3CH_3$ | 0 | $CH_2$ | 1 | 2 | 2 | O | — |
| 227 | $C_6H_5$ | $C_6H_5$ | H | S | 3 | S | 3 | O | NH-i-$C_3H_7$ | 0 | $CH_2$ | 1 | 2 | 2 | O | — |
| 228 | $C_6H_5$ | $C_6H_5$ | H | S | 2 | S | 2 | O | NH-i-$C_3H_7$ | 2 | O | 2 | 2 | 2 | O | — |
| 229 | $C_6H_5$ | $C_6H_5$ | H | S | 2 | S | 2 | O | NH-i-$C_3H_7$ | 2 | $NCH_3$ | 2 | 2 | 2 | O | — |
| 230 | 4-$CH_3OC_6H_4$ | 4-$CH_3OC_6H_4$ | H | S | 2 | S | 2 | O | NH-i-$C_3H_7$ | 0 | $CH_2$ | 1 | 2 | 2 | $NCH_3$ | — |
| 231 | 4-$CH_3OC_6H_4$ | 4-$CH_3OC_6H_4$ | H | S | 2 | S | 2 | O | NH-i-$C_3H_7$ | 2 | $CH_2$ | 1 | 2 | 2 | O | — |
| 232 | 4-$CH_3OC_6H_4$ | 4-$CH_3OC_6H_4$ | H | S | 2 | S | 2 | O | $NHCH_2C_6H_5$ | 0 | $CH_2$ | 1 | 2 | 1 | $CH_2$ | — |
| 233 | 4-$CH_3OC_6H_4$ | 4-$CH_3OC_6H_4$ | H | S | 2 | S | 2 | O | $CH_2C_6H_5$ | 0 | $CH_2$ | 1 | 2 | 3 | $CH_2$ | — |
| 234 | 4-$CH_3OC_6H_4$ | 4-$CH_3OC_6H_4$ | H | S | 2 | S | 2 | O | NH-i-$C_3H_7$ | 0 | $CH_2$ | 1 | 2 | 2 | CO | — |
| 235 | 4-$CH_3OC_6H_4$ | 4-$CH_3OC_6H_4$ | H | S | 2 | S | 2 | O | NH-2-$C_5H_4N$ | 0 | $CH_2$ | 1 | 2 | 2 | CO | — |
| 236 | 4-$CH_3OC_6H_4$ | 4-$CH_3OC_6H_4$ | H | S | 2 | S | 2 | O | NH-i-$C_3H_7$ | 0 | $CH_2$ | 1 | 3 | 0 | CO | — |
| 237 | 4-$CH_3OC_6H_4$ | 4-$CH_3OC_6H_4$ | H | S | 2 | S | 2 | O | NH-i-$C_3H_7$ | 0 | $CH_2$ | 1 | 2 | 1 | C(=O)N$CH_3$ | — |
| 238 | 4-$CH_3OC_6H_4$ | 4-$CH_3OC_6H_4$ | H | S | 2 | S | 2 | O | NH-2,4-$C_6H_3F_2$ | 0 | $CH_2$ | 1 | 2 | 1 | C(=O)O | — |
| 239 | 4-$CH_3OC_6H_4$ | 4-$CH_3OC_6H_4$ | H | S | 2 | S | 2 | O | $NHCH_3$ | 2 | $CH_2$ | 2 | 2 | 2 | C=O | — |
| 240 | 4-$CH_3OC_6H_4$ | 4-$CH_3OC_6H_4$ | H | S | 2 | S | 2 | O | NH-4-$CH_3S-C_6H_4$ | 2 | $NCH_3$ | 2 | 2 | 1 | C(=O)O | — |
| 241 | i-$C_3H_7$ | 4-$CH_3OC_6H_4$ | H | S | 4 | $CH_2$ | 2 | S | $NHCH_2C_6H_5$ | 0 | $CH_2$ | 1 | 2 | 2 | O | — |
| 242 | i-$C_3H_7$ | 4-$CH_3OC_6H_4$ | H | S | 4 | $NCH_3$ | 2 | S | $NHCH_2C_6H_5$ | 0 | $CH_2$ | 1 | 2 | 2 | O | — |
| 243 | i-$C_3H_7$ | 4-$CH_3OC_6H_4$ | H | S | 4 | O | 2 | S | $NHCH_2C_6H_5$ | 0 | $CH_2$ | 1 | 2 | 2 | O | — |
| 244 | i-$C_3H_7$ | 4-$CH_3OC_6H_4$ | H | S | 4 | S | 2 | S | $NHCH_2C_6H_5$ | 0 | $CH_2$ | 1 | 2 | 2 | O | — |
| 245 | 3-$ClC_6H_4$ | 3-$ClC_6H_4$ | $CH_3$ | $NCH_3$ | 2 | $CH_2$ | 4 | S | $C_6H_5$ | 0 | $CH_2$ | 1 | 2 | 2 | O | — |
| 246 | 3-$ClC_6H_4$ | 3-$ClC_6H_4$ | $CH_3$ | $NCH_3$ | 2 | $NCH_3$ | 4 | S | $C_6H_5$ | 0 | $CH_2$ | 1 | 2 | 2 | O | — |
| 247 | 3-$ClC_6H_4$ | 3-$ClC_6H_4$ | $CH_3$ | $NCH_3$ | 2 | O | 4 | S | $C_6H_5$ | 0 | $CH_2$ | 1 | 2 | 2 | O | — |
| 248 | 3-$ClC_6H_4$ | 3-$ClC_6H_4$ | $CH_3$ | $NCH_3$ | 2 | S | 4 | S | $C_6H_5$ | 2 | O | 2 | 2 | 2 | O | — |
| 249 | $C_6H_{11}$ | $C_6H_{11}$ | $C_6H_5$ | $CH_2$ | 4 | $CH_2$ | 4 | S | $NC_6H_5$ | 2 | $NCH_3$ | 2 | 2 | 2 | O | — |
| 250 | $C_6H_{11}$ | $C_6H_{11}$ | $C_6H_5$ | $CH_2$ | 4 | $NCH_3$ | 4 | S | $NC_6H_5$ | 0 | $CH_2$ | 1 | 2 | 2 | $NCH_3$ | — |
| 251 | $C_6H_{11}$ | $C_6H_{11}$ | $C_6H_5$ | $CH_2$ | 4 | O | 4 | S | $NC_6H_5$ | 2 | $CH_2$ | 1 | 2 | 2 | O | — |
| 252 | $C_6H_{11}$ | $C_6H_{11}$ | $C_6H_5$ | $CH_2$ | 4 | S | 4 | S | $NC_6H_5$ | 0 | $CH_2$ | 1 | 2 | 1 | $CH_2$ | — |
| 253 | 2-furanyl | 2-furanyl | H | S | 3 | $CH_2$ | 3 | $H_2$ | $CH_2CH(CH_3)_2$ | 0 | $CH_2$ | 1 | 2 | 3 | $CH_2$ | — |
| 254 | 2-furanyl | 2-furanyl | H | S | 3 | $NCH_3$ | 3 | $H_2$ | $CH_2CH(CH_3)_2$ | 0 | $CH_2$ | 1 | 2 | 2 | CO | — |
| 255 | 2-furanyl | 2-furanyl | H | S | 3 | O | 3 | $H_2$ | $CH_2CH(CH_3)_2$ | 0 | $CH_2$ | 1 | 2 | 2 | CO | — |
| 256 | 2-furanyl | 2-furanyl | H | S | 3 | S | 3 | $H_2$ | $CH_2CH(CH_3)_2$ | 0 | $CH_2$ | 1 | 3 | 0 | CO | — |
| 257 | $C_6H_{11}C_2H_4$ | $C_6H_{11}C_2H_4$ | $CH_3$ | $NCH_3$ | 2 | $CH_2$ | 2 | $H_2$ | $C_7H_{15}$ | 0 | $CH_2$ | 1 | 2 | 1 | C(=O)N$CH_3$ | — |
| 258 | $C_6H_{11}C_2H_4$ | $C_6H_{11}C_2H_4$ | $CH_3$ | $NCH_3$ | 2 | $NCH_3$ | 2 | $H_2$ | $C_7H_{15}$ | 0 | $CH_2$ | 1 | 2 | 1 | C(=O)O | — |
| 259 | $C_6H_{11}C_2H_4$ | $C_6H_{11}C_2H_4$ | $CH_3$ | $NCH_3$ | 2 | O | 2 | $H_2$ | $C_7H_{15}$ | 2 | $CH_2$ | 2 | 2 | 2 | C=O | — |
| 260 | $C_6H_{11}C_2H_4$ | $C_6H_{11}C_2H_4$ | $CH_3$ | $NCH_3$ | 2 | S | 2 | $H_2$ | $C_7H_{15}$ | 2 | $NCH_3$ | 2 | 2 | 1 | C(=O)O | — |

Footnotes to Table 3
[a]) $^1$H NMR (CDCl$_3$): 9.68(1H, s); 7.52–7.26(5H, m); 6.79(4H, d, J=8.8Hz); 6.73–6.55(2H, m); 3.79(6H, s); 3.75–3.67(4H, m); 3.42(4H, br s); 2.93(2H, t, J=6.4Hz); 2.64–2.58(6H, m); 1.80–1.44(6H, m).
[b]) $^1$H NMR (CDCl$_3$): 9.95(1H, br s); 7.60–7.20(11H, m); 6.76–6.62(3H, m); 3.64(4H, t, J=4.6Hz); 3.47(2H, t, J=5.9Hz); 3.39(2H, t, J=5.4Hz); 3.14(2H, t, J=5.7Hz); 2.85(2H, t, J=5.9Hz); 2.71(2H, t, J=5.7Hz); 2.56(2H, t, J=5.4Hz); 2.55–2.45(4H, m); 2.39(3H, s).
[c]) $^1$H NMR (CDCl$_3$): 7.53(4H, d, J=7.0Hz); 7.35–7.25(6H, m); 6.86(1H, br d, J=7.0Hz); 3.82(1H, m, J=6.6Hz); 3.68(4H, t, J=4.6Hz); 3.35(2H, t, J=6.6Hz); 3.19(2H, t, J=5.1Hz); 3.11(2H, t, J=5.7Hz); 2.84(2H, t, J=5.7Hz); 2.63(2H, t, J=6.6Hz); 2.49–2.41(6H, m); 2.36(3H, s); 1.11(6H, d, J=6.6Hz).

EXAMPLE 261

Preparation of N-(2-butoxyethyl)-N'-(2,4-difluorophenyl)-N-[5-(4,5-diphenyl-1H-imidazol-2-ylthio)pentyl]-urea Part A A solution of phosphorous tribromide (5.20 mL, 54.8 mmol) in 10 mL benzene was cooled to 0° C., and pyridine (2.3 mL) was slowly added. Then, after 5 minutes, a solution of 10 mL benzene, butyl cellosolve (20 mL, 153 mmol) and pyridine (0.8 mL, total 3.1 mL, 38.3 mmol) was added dropwise over 1 hour. The mixture was allowed to warm slowly to ambient temperature and stirred for 56 hours, then poured carefully into ice water (100 mL) and extracted with ethyl acetate (2×100 mL). The extracts were dried over brine, combined, dried over anhydrous potassium carbonate and evaporated. The resulting clear, colorless liquid, 1-butoxy-2-bromoethane (11.01 g, 61.1 mmol, 40%), was sufficiently pure for the next step. $^1$H NMR (300 MHz, CDCl$_3$): 3.67 (2H, t, J=6.4 Hz); 3.45–3.37 (4H, m); 1.56–1.45 (2H, m); 1.38–1.26 (2H, m); 0.86 (3H, t, J=7.3 Hz).

Part B

1-Butoxy-2-bromoethane (prepared above, 11.0 g, 61.1 mmol), sodium azide (5.27 g, 81.1 mmol), and sodium iodide (2.26 g, 15.1 mmol) were dissolved in 70 mL dry dimethylformamide, and heated to 60° C. for 18 hours. The mixture was then cooled and poured into 300 mL ethyl acetate, which was washed with water (2×300 mL), dried over anhydrous magnesium sulfate, and evaporated to afford the crude azide. This was taken up in 60 mL dry tetrahydrofuran, and cooled to 0° C. Solid triphenylphosphine (17.6 g, 67.3 mmol) was added in one portion, and the mixture was allowed to warm and stir overnight. Then, water (2.0 mL, 110 mmol) was added, and the mixture was stirred for an additional 20 hours. Solid potassium carbonate (14.3 g, 103 mmol) was added, and the mixture was allowed to stir and dry for 2 hours. Then, a 1:1 tetrahydrofuran solution of 5-bromopentanoyl chloride (10.0 mL, 75.2 mmol) was added dropwise over 30 minutes. The mixture was stirred for an additional 4 hours, then poured into water (400 mL) and extracted with ethyl acetate (2×400 mL). The extracts were combined, dried over anhydrous magnesium sulfate and evaporated. The product (N-(2-butoxyethyl)-5-bromopentanamide) was then purified by flash chromatography (1:1 ethyl acetate-hexane) as an oil (10.63 g, 37.94 mmol, 62% overall). $^1$H NMR (300 MHz, CDCl$_3$): 5.93 (1H, br s); 3.58–3.42 (8H, m); 2.23 (2H, t, J=7.1 Hz); 1.96–1.88 (2H, m); 1.88–1.77 (2H, m); 1.61–1.51 (2H, m); 1.43–1.26 (2H, m); 0.93 (3H, t, J=7.3 Hz).

Part C

N-(2-butoxyethyl)-5-bromopentanamide (3.89 g, 13.9 mmol), 4,5-diphenyl-1H-imidazole-2-thiol (3.57 g, 14.2 mmol), potassium carbonate (2.38 g, 17.2 mmol) and tetra-n-butylammonium iodide (1.50 g, 4.06 mmol) were mixed in 100 mL anhydrous tetrahydrofuran, and heated to reflux for 18 hours. After cooling, the mixture was poured into water (400 mL). This mixture was extracted with ethyl acetate (2×400 mL), and the extracts were combined, dried over anhydrous magnesium sulfate and evaporated. The residue was eluted through a short plug of silica gel (ethyl acetate), and evaporation afforded sufficiently pure N-(2-butoxyethyl)-5-(4,5-diphenyl-1H-imidazol-2-ylthio)-pentanamide (8.69 g).

This material was dissolved in 50 mL toluene, cooled to 0° C., and treated with a toluene solution of Red-Al ™ (15.0 mL, 3.4M, 51 mmol). The ice bath was removed, and the reaction mixture was heated to reflux for 30 hours. After cooling back to 0° C., the mixture was quenched with the addition of 15 mL 2N aqueous sodium hydroxide solution. The solution was washed with brine, dried over anhydrous potassium carbonate and evaporated to afford sufficiently pure N-(2-butoxyethyl)-4-(4,5-diphenyl-1H-imidazol-2-ylthio)pentanamine (4.98 g).

A portion of this amine (2.49 g) was dissolved in 100 mL 1:1 methylene chloride-toluene, and cooled to 0° C. 2,4-Difluorophenylisocyanate (0.7 mL, 5.91 mmol) was added slowly via syringe, and the mixture was slowly warmed and stirred for 20 hours. The solvent was evaporated, and the product, N-(2-butoxyethyl)-N'-(2,4-difluorophenyl)-N-[5-(4,5-diphenyl-1H-imidazol-2-ylthio) pentyl]-urea, was isolated by flash chromatography (1:3 ethyl acetate-hexane) as a solid, melting point: 69–71° C. (2.01 g, 3.39 mmol, 60%). $^1$H NMR (300 MHz, CDCl$_3$): 11.18 (1H, br s); 8.33 (1H, s); 7.62–7.50 (4H, m); 7.35 (1H, br s); 7.31–7.24 (6H, m); 6.72–6.64 (1H, m); 6.54–6.47 (1H, m); 3.63–3.44 (8H, m); 2.97 (2H, t, J=6.6 Hz); 1.81–1.72 (2H, m); 1.71–1.49 (6H, m); 1.42–1.28 (2H, m); 0.91 (3H, t, J=7.3 Hz). Elemental analysis: calculated C 66.87, H 6.46, N 9.45; found C 66.94, H 6.52, N 9.24.

EXAMPLE 283

Preparation of N-[5-(4,5-diphenyl-1H-imidazol-2-ylthio)-pentyl]-N-[2-(2-hydroxyethoxy)-ethyl]-N'-(1-methylethyl)-urea Part A A solution of hydroxyethoxyethylamine (10.0 mL, 139 mmol) and triethylamine (20.0 mL, 143 mmol) in tetrahydrofuran (100 mL) was cooled to −5° C., and treated with a solution of 5-bromopentanoyl chloride (10.0 mL, 75.2 mmol) in tetrahydrofuran (30 mL) dropwise over 30 minutes. The mixture was allowed to stir for 48 hours, then poured into water (400 mL) and extracted with methylene chloride (2×400 mL). The extracts were combined, dried over anhydrous magnesium sulfate and evaporated. The residue was separated by flash chromatography (1:1 acetone-hexane) to afford, first, N-[2-(2-(5-bromopentanoyloxy)-ethoxy)-ethyl]-5bromopentanamide (5.57 g, 12.9 mmol, 34%), then N-[2-(2-hydroxyethoxy)-ethyl]-5-bromopentanamide (6.43 g, 24.0 mmol, 32%). IR (NaCl): 3500, 3298, 1649 cm$^{-1}$.

Part B

The bromide from Part A (6.43 g, 24.0 mmol), 4,5-diphenyl-1H-imidazole-2-thiol (6.13 g, 24.3 mmol), anhydrous potassium carbonate (3.96 g, 28.7 mmol), and tetra-n-butylammonium iodide (1.77 g, 4.79 mmol) were mixed in anhydrous tetrahydrofuran (70 mL), and heated to reflux under nitrogen atmosphere for 20 hours. After being cooled to ambient temperature, the reaction mixture was poured into water (200 mL), and this was extracted with methylene chloride (2×200 mL). The extracts were combined, dried over anhydrous magnesium sulfate, and evaporated. The residual oil was separated by flash chromatography (1:1 acetone-hexane) to afford N-[2-(2-hydroxyethoxy)-ethyl]-5-(4,5-diphenyl-1H-imidazol-2-ylthio)-pentanamide (10.1 g, 23.0 mmol, 96%) as a solid, melting point 176°–178° C.

Part C

A solution of sodium bis(methoxyethoxy)aluminum hydride (47.6 mmol) in toluene (64 mL) was cooled to 0° C., and a solution of the amide prepared above in Part B (6.59 g, 15.0 mmol) in anhydrous tetrahydrofuran (60 mL) was added dropwise over 30 minutes. The ice bath was removed, and the mixture was heated to reflux for 24 hours. After being cooled to 0° C., the reaction was quenched with the addition of 15% aqueous sodium hydroxide solution (5 mL) and water (20 mL). The mixture was poured into 100 mL water, and the layers separated. The aqueous phase was neutralized to pH 7 with concentrated aqueous hydrochloric acid solution, saturated with sodium chloride, filtered, and reextracted with methylene chloride (120 mL). The organic phases were combined, dried over anhydrous potassium carbonate, and evaporated to afford the product amine (6.27 g, 14.7 mmol, 98%).

The crude amine thus obtained (3.35 g, 7.87 mmol) was dissolved in 30 mL methylene chloride, and cooled to 0° C. This solution was treated with isopropylisocyanate, and stirred for 18 hours. The solution was then evaporated, and the residue separated by flash chromatography (1:1 acetone-hexane) to afford the product (N-[5-(4,5-diphenyl-1H-imidazol-2-ylthio)-pentyl]-N-[2-(2-hydroxyethoxy)-ethyl]-N'-(1-methylethyl)-urea) as a gum (4.02 g, 7.87 mmol, 100%). $^1$H NMR (CDCl$_3$): 11.73 (1H, br s); 7.55 (4H, br s); 7.31–7.21 (6H, s); 5.47 (1H, d, J=6 Hz); 3.79–3.70 (3H, m); 3.64–3.58 (4H, m); 3.40–3.33 (4H, m); 2.98 (2H, t, J=7 Hz); 2.44 (1H, br s); 1.80–1.69 (2H, m); 1.61–1.46 (4H, m); 1.06 (6H, d, J=7 Hz). Elemental analysis: calculated C 65.85, H 7.50, N 10.98; found C 65.69, H 7.51, N 10.78.

Compounds 261–360 in Table 4 were prepared or could be prepared analogously by the procedures described in Examples 261 and 283 by employing the appropriately substituted starting materials. The compounds in Table 4 represent those analogues bearing an alkoxyalkyl group on the trisubstituted nitrogen atom.

TABLE 4

$$R^1\underset{R^2}{\overset{N}{\diagdown}}\underset{\underset{R^3}{|}}{N}-X-(CH_2)_m-A-(CH_2)_n-\underset{\underset{Z}{\overset{Y}{||}}}{N}-(CH_2)_p-O-(CH_2)_q-D$$

| Example | R¹ | R² | R³ | X | m | A | n | Y | Z | p | q | D | mp |
|---|---|---|---|---|---|---|---|---|---|---|---|---|---|
| 261 | C₆H₅ | C₆H₅ | H | S | 2 | CH₂ | 2 | O | NH-2,4-C₆H₃F₂ | 2 | 2 | C₂H₅ | 69-71 |
| 262 | C₆H₅ | C₆H₅ | H | S | 2 | CH₂ | 2 | O | NH-i-C₃H₇ | 2 | 2 | C₂H₅ | oil[a] |
| 263 | 4-CH₃OC₆H₄ | 4-CH₃OC₆H₄ | H | S | 2 | CH₂ | 2 | O | NH-2,4-C₆H₃F₂ | 2 | 2 | C₂H₅ | — |
| 264 | 4-CH₃OC₆H₄ | 4-CH₃OC₆H₄ | H | S | 2 | CH₂ | 2 | O | NH-i-C₃H₇ | 2 | 2 | C₂H₅ | — |
| 265 | 4-CH₃SC₆H₄ | 4-CH₃SC₆H₄ | H | S | 2 | CH₂ | 2 | O | NH-i-C₃H₇ | 2 | 2 | C₂H₅ | — |
| 266 | C₆H₅ | C₆H₅ | CH₃ | S | 2 | CH₂ | 2 | O | NH-i-C₃H₇ | 2 | 2 | C₂H₅ | — |
| 267 | 4-CH₃OC₆H₄ | 4-CH₃OC₆H₄ | H | SO₂ | 2 | CH₂ | 2 | O | NH-i-C₃H₇ | 2 | 2 | C₂H₅ | — |
| 268 | 4-CH₃OC₆H₄ | 4-CH₃OC₆H₄ | H | S | 2 | CH₂ | 2 | O | NH-i-C₃H₇ | 3 | 3 | C₂H₅ | — |
| 269 | 4-CH₃OC₆H₄ | 4-CH₃OC₆H₄ | H | S | 2 | CH₂ | 2 | O | OCH₂C₆H₅ | 2 | 2 | C₂H₅ | — |
| 270 | 4-CH₃OC₆H₄ | 4-CH₃OC₆H₄ | H | S | 2 | CH₂ | 2 | O | CH₂C₆H₁₃ | 2 | 2 | C₂H₅ | — |
| 271 | C₆H₅ | C₆H₅ | H | NCH₃ | 2 | CH₂ | 2 | NCH₃ | CH₂C₆H₁₃ | 2 | 2 | C₂H₅ | — |
| 272 | C₆H₅ | C₆H₅ | H | S | 2 | O | 2 | O | NH-i-C₃H₇ | 2 | 2 | C₂H₅ | — |
| 273 | C₆H₅ | C₆H₅ | H | S | 3 | O | 3 | O | NH-i-C₃H₇ | 2 | 2 | C₂H₅ | — |
| 274 | C₆H₅ | C₆H₅ | H | S | 2 | O | 2 | O | CH₂C₆H₅ | 2 | 2 | C₂H₅ | — |
| 275 | C₆H₅ | C₆H₅ | H | S | 2 | S | 2 | H₂ | NH-i-C₃H₇ | 2 | 2 | C₂H₅ | — |
| 276 | C₆H₅ | C₆H₅ | H | S | 3 | S | 3 | O | NH-i-C₃H₇ | 2 | 2 | C₂H₅ | — |
| 277 | C₆H₅ | C₆H₅ | H | S | 2 | S | 2 | H₂ | C₂H₅ | 2 | 2 | C₂H₅ | — |
| 278 | 4-(CH₃)₂NC₆H₄ | 4-(CH₃)₂NC₆H₄ | H | S | 2 | CH₂ | 2 | O | NH-i-C₃H₇ | 2 | 2 | C₂H₅ | — |
| 279 | 4-CH₃SC₆H₄ | 4-CH₃SC₆H₄ | H | S | 2 | CH₂ | 2 | O | NH-2-C₅H₄N | 2 | 2 | C₂H₅ | — |
| 280 | C₆H₅ | C₆H₅ | C₆H₅ | S | 2 | CH₂ | 2 | O | NH-i-C₃H₇ | 4 | 4 | C₂H₅ | — |
| 281 | C₆H₅ | C₆H₅ | H | S | 2 | CH₂ | 2 | O | NH-2,4-C₆H₃F₂ | 2 | 2 | OH | oil[b] |
| 282 | C₆H₅ | C₆H₅ | H | S | 2 | CH₂ | 2 | O | NH-i-C₃H₇ | 2 | 2 | OH | oil[c] |
| 283 | 4-CH₃OC₆H₄ | 4-CH₃OC₆H₄ | H | S | 2 | CH₂ | 2 | O | NH-2,4-C₆H₃F₂ | 2 | 2 | OH | oil[d] |
| 284 | 4-CH₃OC₆H₄ | 4-CH₃OC₆H₄ | H | S | 2 | CH₂ | 2 | O | NH-i-C₃H₇ | 2 | 2 | OH | oil[e] |
| 285 | 4-CH₃SC₆H₄ | 4-CH₃SC₆H₄ | H | S | 2 | CH₂ | 2 | O | NH-i-C₃H₇ | 2 | 2 | OH | — |
| 286 | C₆H₅ | C₆H₅ | CH₃ | S | 2 | CH₂ | 2 | O | NH-i-C₃H₇ | 2 | 2 | OH | — |
| 287 | 4-CH₃OC₆H₄ | 4-CH₃OC₆H₄ | H | SO₂ | 2 | CH₂ | 2 | O | NH-i-C₃H₇ | 2 | 2 | OH | — |
| 288 | 4-CH₃OC₆H₄ | 4-CH₃OC₆H₄ | H | S | 2 | CH₂ | 2 | O | NH-i-C₃H₇ | 3 | 3 | OH | — |
| 289 | 4-CH₃OC₆H₄ | 4-CH₃OC₆H₄ | H | S | 2 | CH₂ | 2 | O | OCH₂C₆H₅ | 2 | 2 | OH | — |
| 290 | 4-C₃OC₆H₄ | 4-C₃OC₆H₄ | H | S | 2 | CH₂ | 2 | O | CH₂C₆H₁₃ | 2 | 2 | OH | — |
| 291 | C₆H₅ | C₆H₅ | H | NCH₃ | 2 | CH₂ | 2 | NCH₃ | CH₂C₆H₁₃ | 2 | 2 | OH | — |
| 292 | C₆H₅ | C₆H₅ | H | S | 2 | O | 2 | O | NH-i-C₃H₇ | 2 | 2 | OH | — |
| 293 | C₆H₅ | C₆H₅ | H | S | 3 | O | 3 | O | NH-i-C₃H₇ | 2 | 2 | OH | — |
| 294 | C₆H₅ | C₆H₅ | H | S | 2 | O | 2 | O | CH₂C₆H₅ | 2 | 2 | OH | — |
| 295 | C₆H₅ | C₆H₅ | H | S | 2 | S | 2 | H₂ | NH-i-C₃H₇ | 2 | 2 | OH | — |
| 296 | C₆H₅ | C₆H₅ | H | S | 3 | S | 3 | O | NH-i-C₃H₇ | 2 | 2 | OH | — |
| 297 | C₆H₅ | C₆H₅ | H | S | 2 | S | 2 | H₂ | C₂H₅ | 2 | 2 | OH | — |
| 298 | 4-(CH₃)₂NC₆H₄ | 4-(CH₃)₂NC₆H₄ | H | S | 2 | CH₂ | 2 | O | NH-i-C₃H₇ | 2 | 2 | OH | — |
| 299 | 4-CH₃SC₆H₄ | 4-CH₃SC₆H₄ | H | S | 2 | CH₂ | 2 | O | NH-2-C₅H₄N | 2 | 2 | OH | — |
| 300 | C₆H₅ | C₆H₅ | H | S | 2 | CH₂ | 2 | O | NH-i-C₃H₇ | 4 | 4 | OH | — |
| 301 | C₆H₅ | C₆H₅ | H | S | 2 | CH₂ | 2 | O | NH-2,4-C₆H₃F₂ | 2 | 2 | OCH₃ | — |
| 302 | C₆H₅ | C₆H₅ | H | S | 2 | CH₂ | 2 | O | NH-i-C₃H₇ | 2 | 2 | OCH₃ | oil[f] |
| 303 | 4-CH₃OC₆H₄ | 4-CH₃OC₆H₄ | H | S | 2 | CH₂ | 2 | O | NH-2,4-C₆H₃F₂ | 2 | 2 | OCH₃ | oil[g] |
| 304 | 4-CH₃OC₆H₄ | 4-CH₃OC₆H₄ | H | S | 2 | CH₂ | 2 | O | NH-i-C₃H₇ | 2 | 2 | OCH₃ | — |
| 305 | 4-CH₃SC₆H₄ | 4-CH₃SC₆H₄ | H | S | 2 | CH₂ | 2 | O | NH-i-C₃H₇ | 2 | 2 | OCH₃ | — |

TABLE 4-continued

| # | | | | | | | | | | | |
|---|---|---|---|---|---|---|---|---|---|---|---|
| 306 | C$_6$H$_5$ | C$_6$H$_5$ | CH$_3$ | S | 2 | CH$_2$ | 2 | O | 2 | NH-i-C$_3$H$_7$ | OCH$_3$ | — |
| 307 | 4-CH$_3$OC$_6$H$_4$ | 4-CH$_3$OC$_6$H$_4$ | H | SO$_2$ | 2 | CH$_2$ | 2 | O | 2 | NH-i-C$_3$H$_7$ | OCH$_3$ | — |
| 308 | 4-CH$_3$OC$_6$H$_4$ | 4-CH$_3$OC$_6$H$_4$ | H | S | 3 | CH$_2$ | 3 | O | 3 | NH-i-C$_3$H$_7$ | OCH$_3$ | — |
| 309 | 4-CH$_3$OC$_6$H$_4$ | 4-CH$_3$OC$_6$H$_4$ | H | S | 2 | CH$_2$ | 2 | O | 2 | OCH$_2$C$_6$H$_5$ | OCH$_3$ | — |
| 310 | 4-CH$_3$OC$_6$H$_4$ | 4-CH$_3$OC$_6$H$_4$ | H | NCH$_3$ | 2 | CH$_2$ | 2 | O | 2 | CH$_2$C$_6$H$_{13}$ | OCH$_3$ | — |
| 311 | C$_6$H$_5$ | C$_6$H$_5$ | H | S | 2 | O | 2 | O | 2 | CH$_2$C$_6$H$_{13}$ | OCH$_3$ | — |
| 312 | C$_6$H$_5$ | C$_6$H$_5$ | H | S | 3 | O | 3 | O | 3 | NH-i-C$_3$H$_7$ | OCH$_3$ | — |
| 313 | C$_6$H$_5$ | C$_6$H$_5$ | H | S | 2 | O | 2 | O | 2 | NH-i-C$_3$H$_7$ | OCH$_3$ | — |
| 314 | C$_6$H$_5$ | C$_6$H$_5$ | H | S | 2 | S | 2 | H$_2$ | 2 | CH$_2$C$_6$H$_5$ | OCH$_3$ | — |
| 315 | C$_6$H$_5$ | C$_6$H$_5$ | H | S | 3 | S | 3 | O | 3 | NH-i-C$_3$H$_7$ | OCH$_3$ | — |
| 316 | C$_6$H$_5$ | C$_6$H$_5$ | H | S | 2 | S | 2 | H$_2$ | 2 | NH-i-C$_3$H$_7$ | OCH$_3$ | — |
| 317 | C$_6$H$_5$ | C$_6$H$_5$ | H | S | 2 | S | 2 | O | 2 | CH$_2$C$_6$H$_5$ | OCH$_3$ | — |
| 318 | 4-(CH$_3$)$_2$NC$_6$H$_4$ | 4-(CH$_3$)$_2$NC$_6$H$_4$ | H | S | 2 | CH$_2$ | 2 | O | 2 | NH-i-C$_3$H$_7$ | OCH$_3$ | — |
| 319 | 4-CH$_3$SC$_6$H$_4$ | 4-CH$_3$SC$_6$H$_4$ | H | S | 2 | CH$_2$ | 2 | O | 2 | NH-2-C$_3$H$_4$N | OCH$_3$ | oil[h] |
| 320 | C$_6$H$_5$ | C$_6$H$_5$ | C$_6$H$_5$ | S | 2 | CH$_2$ | 2 | O | 4 | NH-2,4-C$_6$H$_3$F$_2$ | OCH$_3$ | oil[i] |
| 321 | C$_6$H$_5$ | C$_6$H$_5$ | H | S | 2 | CH$_2$ | 2 | O | 2 | NH-i-C$_3$H$_7$ | OC$_2$H$_5$ | — |
| 322 | C$_6$H$_5$ | C$_6$H$_5$ | H | S | 2 | CH$_2$ | 2 | O | 2 | NH-2,4-C$_6$H$_3$F$_2$ | OC$_2$H$_5$ | oil[i] |
| 323 | 4-CH$_3$OC$_6$H$_4$ | 4-CH$_3$OC$_6$H$_4$ | H | S | 2 | CH$_2$ | 2 | O | 2 | NH-i-C$_3$H$_7$ | OC$_2$H$_5$ | — |
| 324 | 4-CH$_3$OC$_6$H$_4$ | 4-CH$_3$OC$_6$H$_4$ | H | S | 3 | CH$_2$ | 3 | O | 3 | NH-i-C$_3$H$_7$ | OC$_2$H$_5$ | — |
| 325 | 4-CH$_3$SC$_6$H$_4$ | 4-CH$_3$SC$_6$H$_4$ | H | S | 2 | CH$_2$ | 2 | O | 2 | NH-i-C$_3$H$_7$ | OC$_2$H$_5$ | — |
| 326 | C$_6$H$_5$ | C$_6$H$_5$ | CH$_3$ | S | 2 | CH$_2$ | 2 | O | 2 | NH-i-C$_3$H$_7$ | OC$_2$H$_5$ | — |
| 327 | 4-CH$_3$OC$_6$H$_4$ | 4-CH$_3$OC$_6$H$_4$ | H | SO$_2$ | 2 | CH$_2$ | 2 | O | 2 | OCH$_2$C$_6$H$_5$ | OC$_2$H$_5$ | — |
| 328 | 4-CH$_3$OC$_6$H$_4$ | 4-CH$_3$OC$_6$H$_4$ | H | S | 2 | CH$_2$ | 2 | O | 2 | CH$_2$C$_6$H$_5$ | OC$_2$H$_5$ | — |
| 329 | 4-CH$_3$OC$_6$H$_4$ | 4-CH$_3$OC$_6$H$_4$ | H | S | 3 | CH$_2$ | 3 | O | 3 | CH$_2$C$_6$H$_{13}$ | OC$_2$H$_5$ | — |
| 330 | 4-CH$_3$OC$_6$H$_4$ | 4-CH$_3$OC$_6$H$_4$ | H | NCH$_3$ | 2 | CH$_2$ | 2 | NCH$_3$ | 2 | CH$_2$C$_6$H$_{13}$ | OC$_2$H$_5$ | — |
| 331 | C$_6$H$_5$ | C$_6$H$_5$ | H | S | 2 | O | 2 | O | 2 | NH-i-C$_3$H$_7$ | OC$_2$H$_5$ | — |
| 332 | C$_6$H$_5$ | C$_6$H$_5$ | H | S | 3 | O | 3 | O | 3 | NH-i-C$_3$H$_7$ | OC$_2$H$_5$ | — |
| 333 | C$_6$H$_5$ | C$_6$H$_5$ | H | S | 2 | O | 2 | H$_2$ | 2 | NH-i-C$_3$H$_7$ | OC$_2$H$_5$ | — |
| 334 | C$_6$H$_5$ | C$_6$H$_5$ | H | S | 2 | S | 2 | O | 2 | NH-i-C$_3$H$_7$ | OC$_2$H$_5$ | — |
| 335 | C$_6$H$_5$ | C$_6$H$_5$ | H | S | 2 | S | 2 | H$_2$ | 2 | NH-i-C$_3$H$_7$ | OC$_2$H$_5$ | — |
| 336 | C$_6$H$_5$ | C$_6$H$_5$ | H | S | 2 | S | 2 | O | 2 | OCH$_2$C$_6$H$_5$ | OC$_2$H$_5$ | — |
| 337 | C$_6$H$_5$ | C$_6$H$_5$ | H | S | 2 | S | 2 | O | 2 | CH$_2$C$_6$H$_5$ | OC$_2$H$_5$ | — |
| 338 | 4-(CH$_3$)$_2$NC$_6$H$_4$ | 4-(CH$_3$)$_2$NC$_6$H$_4$ | H | S | 2 | CH$_2$ | 2 | O | 2 | NH-i-C$_3$H$_7$ | OC$_2$H$_5$ | — |
| 339 | 4-C$_3$SC$_6$H$_4$ | 4-C$_3$SC$_6$H$_4$ | H | S | 2 | CH$_2$ | 2 | O | 2 | NH-2-C$_3$H$_4$N | OC$_2$H$_5$ | — |
| 340 | C$_6$H$_5$ | C$_6$H$_5$ | C$_6$H$_5$ | S | 4 | CH$_2$ | 4 | O | 4 | NH-i-C$_3$H$_7$ | C$_2$H$_5$ | — |
| 341 | i-C$_3$H$_7$ | 4-CH$_3$OC$_6$H$_4$ | H | S | 2 | CH$_2$ | 2 | S | 2 | NHCH$_2$C$_6$H$_5$ | OH | — |
| 342 | i-C$_3$H$_7$ | 4-CH$_3$OC$_6$H$_4$ | H | S | 2 | CH$_2$ | 2 | S | 2 | NHCH$_2$C$_6$H$_5$ | OCH$_3$ | — |
| 343 | i-C$_3$H$_7$ | 4-CH$_3$OC$_6$H$_4$ | H | S | 2 | CH$_2$ | 2 | S | 2 | NHCH$_2$C$_6$H$_5$ | OC$_2$H$_5$ | — |
| 344 | i-C$_3$H$_7$ | 4-CH$_3$OC$_6$H$_4$ | H | S | 2 | CH$_2$ | 2 | S | 2 | NHCH$_2$C$_6$H$_5$ | OC$_2$H$_5$ | — |
| 345 | 3-ClC$_6$H$_4$ | 3-ClC$_6$H$_4$ | CH$_3$ | NCH$_3$ | 4 | O | 4 | S | 4 | C$_6$H$_5$ | OC$_2$H$_5$ | — |
| 346 | 3-ClC$_6$H$_4$ | 3-ClC$_6$H$_4$ | CH$_3$ | NCH$_3$ | 3 | O | 3 | S | 3 | C$_6$H$_5$ | OH | — |
| 347 | 3-ClC$_6$H$_4$ | 3-ClC$_6$H$_4$ | CH$_3$ | NCH$_3$ | 3 | O | 3 | S | 3 | C$_6$H$_5$ | OC$_3$ | — |
| 348 | 3-ClC$_6$H$_4$ | 3-ClC$_6$H$_4$ | CH$_3$ | NCH$_3$ | 2 | O | 2 | S | 2 | C$_6$H$_5$ | OC$_2$H$_5$ | — |
| 349 | C$_6$H$_{11}$ | C$_6$H$_{11}$ | C$_6$H$_5$ | CH$_2$ | 4 | CH$_2$ | 4 | H$_2$ | 4 | NC$_6$H$_5$ | C$_2$H$_5$ | — |
| 350 | C$_6$H$_{11}$ | C$_6$H$_{11}$ | C$_6$H$_5$ | CH$_2$ | 4 | CH$_2$ | 4 | H$_2$ | 4 | NC$_6$H$_5$ | OH | — |
| 351 | C$_6$H$_{11}$ | C$_6$H$_{11}$ | C$_6$H$_5$ | CH$_2$ | 4 | CH$_2$ | 4 | H$_2$ | 4 | NC$_6$H$_5$ | OCH$_3$ | — |
| 352 | C$_6$H$_{11}$ | C$_6$H$_{11}$ | C$_6$H$_5$ | CH$_2$ | 4 | CH$_2$ | 4 | H$_2$ | 4 | NC$_6$H$_5$ | OC$_2$H$_5$ | — |
| 353 | 2-furanyl | 2-furanyl | H | S | 3 | O | 3 | H$_2$ | 3 | CH$_2$CH(CH$_3$)$_2$ | C$_2$H$_5$ | — |
| 354 | 2-furanyl | 2-furanyl | H | S | 3 | O | 3 | H$_2$ | 3 | CH$_2$CH(CH$_3$)$_2$ | OH | — |
| 355 | 2-furanyl | 2-furanyl | H | S | 3 | O | 3 | H$_2$ | 3 | CH$_2$CH(CH$_3$)$_2$ | OCH$_3$ | — |
| 356 | 2-furanyl | 2-furanyl | H | S | 3 | O | 3 | H$_2$ | 3 | CH$_2$CH(CH$_3$)$_2$ | OC$_2$H$_5$ | — |
| 357 | C$_6$H$_{11}$C$_2$H$_4$ | C$_6$H$_{11}$C$_2$H$_4$ | CH$_3$ | NCH$_3$ | 2 | CH$_2$ | 2 | H$_2$ | 2 | C$_7$H$_{15}$ | OCH$_3$ | — |
| 358 | C$_6$H$_{11}$C$_2$H$_4$ | C$_6$H$_{11}$C$_2$H$_4$ | CH$_3$ | NCH$_3$ | 2 | CH$_2$ | 2 | H$_2$ | 2 | C$_7$H$_{15}$ | OH | — |

TABLE 4-continued

| | C₆H₁₁C₂H₄<br>C₆H₁₁C₂H₄ | CH₃<br>CH₃ | NCH₃<br>NCH₃ | 2<br>2 | CH₂<br>CH₂ | H₂<br>H₂ | C₇H₁₅<br>C₇H₁₅ | 4<br>2 | 4<br>2 | OCH₃<br>OC₂H₅ |
|---|---|---|---|---|---|---|---|---|---|---|
| 359 | | | | | | | | | | — |
| 360 | | | | | | | | | | — |

Footnotes to Table 4

*a)*1HNMR(CDCl₃): 12.12(1H, br s); 7.62(2H, d, J=8.1Hz); 7.52(2H, d, J=8.1Hz); 7.33–7.17(6H, m); 5.84(1H, d, J=7.4Hz); 3.70(1H, m, J=6.6Hz); 3.52(2H, t, J=4.2Hz); 3.45(2H, t, J=6.6Hz); 3.39(2H, t, J=6.6Hz); 3.3(2H, t, J=4.4Hz); 2.96(2H, t, J=6.4Hz); 1.78–1.68(2H, m); 1.61–1.37(8H, m); 1.01(6H, d, J=6.6Hz); 0.92(3H, t, J=7.3Hz).

*b)*1HNMR(CDCl₃): 8.09(1H, br s); 7.64(1H, td, J=9.2, 5.8Hz); 7.50–7.40(4H, m); 7.29–7.20(6H, m); 6.75–6.67(4H, m); 6.56(1H, br t, J=7.8Hz); 3.80(2H, t, J=4.6Hz); 3.72(2H, t, J=4.4Hz); 3.68(2H, t, J=5.1Hz); 3.53(2H, t, J=4.4Hz); 3.46(2H, t, J=7.0Hz); 3.01(2H, t, J=6.4Hz); 1.80–1.49(6H, m).

*c)*1HNMR(CDCl₃): 11.73(1H, br s); 7.55(4H, br s); 7.31–7.21(6H, m); 5.47(1H, d, J=6Hz); 3.79–3.70(3H, m); 3.64–3.58(4H, m); 3.40–3.33(4H, m); 2.98(2H, t, J=7Hz); 2.44(1H, br s); 1.80–1.69(2H, m); 1.61–1.46(4H, m); 1.06(6H, d, J=7Hz).

*d)*1HNMR(300MHz, CDCl₃): 11.18(1H, br s); 8.33(1H, s); 7.62–7.50(4H, m); 7.35 1H, br s); 7.31–7.24(6H, m); 6.72–6.64(1H, m); 6.54–6.47(1H, m); 3.63–3.44(8H, m); 2.97(2H, t, J=6.6Hz); 1.81–1.72(2H, m); 1.71–1.49(6H, m); 1.42–1.28(2H, m); 0.91(3H, t, J=7.3Hz).

*e)*1HNMR(CDCl₃): 7.45(4H, br d, J=8.5Hz); 6.83(4H, d, J=8.5Hz); 5.46(1H, br d, J=7.3Hz); 3.80(6H, s); 3.80–3.72(3H, m); 3.63–3.58(4H, m); 3.41–3.34(4H, m); 2.96(2H, t, J=6.4Hz); 1.79–1.66(2H, m); 1.63–1.46(4H, m); 1.05(6H, d, J=6.6Hz).

*f)*1HNMR(CDCl₃): 8.21(1H, br s); 7.60(1H, td, J=9.2, 5.9Hz); 7.54(2H, br s); 7.27(2H, br s); 6.80(4H, d, J=8.8Hz); 6.69(1H, dt, J=8.4, 2.5Hz); 6.60–6.51(1H, m); 3.80(6H, s); 3.76–3.69(4H, m); 3.59–3.51(4H, m); 3.45(2H, t, J=6.4Hz); 3.32(3H, s); 2.97(2H, t, J=6.4Hz); 1.80–1.51(6H, m).

*g)*1HNMR(CDCl₃): 11.81(1H, br s); 7.44(4H, br s); 6.82(4H, d, J=8.4Hz); 5.65(1H, d, J=7.4Hz); 3.80(6H, s); 3.75(1H, m, J=6.2Hz); 3.65–3.51(6H, m); 3.36(3H, s); 3.36–3.30(4H, m); 2.94(2H, t, J=7.2Hz); 1.78–1.68(2H, m); 1.59–1.43(4H, m); 1.04(6H, d, J=6.2Hz).

*h)*1HNMR(CDCl₃): 11.28(1H, s); 8.25(1H, s); 7.64–7.52(3H, m); 7.39–7.30(2H, m); 7.27–7.17(6H, m); 6.71–6.63(1H, m); 6.55–6.49(1H, m); 3.73–3.69(4H, m); 3.67–3.59(2H, m); 3.56–3.43(6H, m); 2.97(2H, t, J=6.6Hz); 1.80–1.71(2H, m); 1.70–1.60(2H, m); 1.59–1.47(2H, m); 1.13(3H, t, J=7.0Hz).

*i)*1HNMR(CDCl₃): 7.52–7.42(4H, m); 7.27–7.16(7H, M); 5.62(1H, d, J=6.9Hz); 3.73(1H, m, J=6.6Hz); 3.60–3.52(6H, m); 3.49(2H, q, J=7.0Hz); 3.32–3.26(4H, m); 2.95(2H, t, J=6.9Hz); 1.71–1.63(6H, m); 1.55–1.46(2H, m); 1.43–1.36(2H, m); 1.20(3H, t, J=7.0Hz); 1.03(TH, d, J=6.6Hz).

*j)*1HNMR(CDCl₃): 7.50(4H, d, J=8.5Hz); 7.15(4H, d, J=8.0Hz); 5.90–5.80(1H, m); 3.70–3.30(14H, m); 3.05–2.95(2H, m); 2.50(6H, s); 1.80–1.70(2H, m); 1.65–1.25(5H, m); 1.20(3H, t, J=7.0Hz); 1.05(5H, d J=6.6Hz).

EXAMPLE 363

Preparation of
N-[2-[2-[4,5-bis(4-methoxyphenyl)-1H-imidazol-2-ylthio]ethoxy]ethyl]-N-heptyl-N'-(1-methylethyl)-urea Part A An 80 mL tetrahydrofuran solution of heptanoyl chloride (20.00 mL, 129 mmol) was cooled to 0° C., and a 200 mL tetrahydrofuran solution of (aminoethoxy)ethanol (10.00 mL, 139 mmol) and triethylamine (20.00 mL, 143 mmol) was added dropwise over 30 minutes. After slow warming to ambient temperature overnight, the mixture was poured into 400 mL water, and extracted with ether. The aqueous phase was reextracted with an equal volume of methylene chloride, and the extracts were washed with brine (400 mL), combined, dried over anhydrous magnesium sulfate and evaporated. $^1$H NMR analysis of the crude mixture showed a mixture of N-[2-(2-hydroxyethoxy)ethyl]-heptanamide and N-[2-(2-(heptanoyloxy) ethoxy)ethyl]-heptanamide (25.8 g).

This crude mixture (16.11 g) was dissolved in 100 mL tetrahydrofuran, and added dropwise to an ice-cooled 100 mL tetrahydrofuran slurry of lithium aluminum hydride (9.21 g, 243 mmol) under nitrogen atmosphere. After the addition was complete, the mixture was warmed to reflux for 18 hours. After cooling to 0° C., the mixture was quenched by the slow, dropwise addition of 10 mL water, 30 mL of 15% aqueous sodium hydroxide, and 30 mL water. The resulting white precipitate was removed by filtration, and the filtrate was dried over anhydrous potassium carbonate and evaporated to afford crude (N-heptylaminoethyl)ethoxyethanol (13.26 g, 65.22 mmol).

The crude product from above (6.63 g, 32.6 mmol) was dissolved in methylene chloride (50 mL), and cooled to 0° C. under nitrogen atmosphere. A solution of isopropylisocyanate (3.20 mL, 32.6 mmol) in hexane (50 mL) was added dropwise over 30 minutes. The mixture was allowed to warm slowly to 20° C. and stirred for 14 hours. The reaction mixture was evaporated, and the residual oil was separated by flash chromatography (1:1 ethyl acetate-hexane) to afford N-heptyl-N-[2-[2-hydroxy-ethoxy]ethyl]-N'-(1-methylethyl)-urea as an oil (4.71 g, 16.3 mmol, 50%). $^1$H NMR (CDCl$_3$): 5.01 (1H, br s); 3.94–3.88 (1H, m); 3.75 (2H, t, J=5.0 Hz); 3.20 (2H, t, J=7.7 Hz); 2.43 (1H, br s); 1.57–1.50 (2H, m); 1.35–1.26 (8H, m); 1.13 (6H, d, J=6.6 Hz); 0.88 (3H, t, J=5.6 Hz).

Part B

The alcohol prepared above (3.81 g, 13.2 mmol) and carbon tetrabromide (5.39 g, 16.3 mmol) were dissolved in methylene chloride (30 mL), and treated with a solution of triphenylphosphine (4.29 g, 16.4 mmol) in methylene chloride (20 mL) over 30 minutes. After stirring for 14 hours, the reaction mixture was evaporated, and the residual oil was separated by flash chromatography (3:7 ethyl acetate-hexane) to afford N-[2-[2-bromoethoxy]ethyl]-N-heptyl-N'-(1-methylethyl)-urea as an clear, colorless syrup (4.20 g, 11.9 mmol, 90%). $^1$H NMR (CDCl$_3$): 5.03 (1H, br s); 3.91 (1H, heptet, J=6.5 Hz); 3.79 (2H, t, J=6.0 Hz); 3.62 (2H, t, J=5.0 Hz); 3.46 (2H, t, J=5.9 Hz); 3.39 (2H, t, J=5.0 Hz); 3.22 (2H, dd, J=8.1, 7.3 Hz); 1.58–1.51 (2H, m); 1.39–1.30 (8H, m); 1.15 (6H, d, J=6.5 Hz); 0.88 (3H, t, J=6.6 Hz).

Part C

The bromide prepared above (1.00 g, 2.85 mmol), 4,5-bis(4-methoxyphenyl)-1H-imidazole-2-thiol (624 mg, 2.00 mmol), potassium carbonate (407 mg, 2.94 mmol) and tetra-n-butylammonium iodide (215 mg, 0.58 mmol) were mixed in dry tetrahydrofuran (25 mL), and the mixture was stirred at 20° C. for 14 hours then heated to reflux for 2 hours. This mixture was then cooled, and poured into water (100 mL). This mixture was extracted with ethyl acetate (2×100 mL), and the organic extracts were washed with brine, combined, dried over anhydrous magnesium sulfate and evaporated. The residue was separated by flash chromatography (1:1 ethyl acetate-hexane) to afford the product (N-[2-[2-[4,5-bis(4-methoxyphenyl)-1H-imidazol-2-ylthio]ethoxy]ethyl]-N-heptyl-N'-(1-methylethyl)-urea) as a gum, which foamed upon vacuum pumping to a solid (1.11 g, 1.90 mmol, 95%), melting point: 85–87° C. $^1$H NMR (300 MHz, CDCl$_3$): 7.44 (4H, d, J=8.6 Hz); 6.84 (4H, d, J=8.6 Hz); 4.77 (1H, d, J=6.6 Hz); 3.83 (1H, m, J=6.6 Hz); 3.80 (6H, s); 3.73 (2H, t, J=5.8 Hz); 3.61 (2H, t, J=5.1 Hz); 3.41 (2H, t, J=5.1 Hz); 3.18 (2H, t, J=5.8 Hz); 3.12 (2H, t, J=7.6 Hz); 1.55–1.43 (2H, m); 1.30–1.18 (8H, m); 1.10 (6H, d, J=6.6 Hz); 0.87 (3H, t, J=6.8 Hz). Elemental analysis: calculated C 65.95, H 7.96, N 9.61; found C 65.86, H 8.01, N 9.42.

Compounds 361–420 in Table 5 were prepared or could be prepared analogously by the procedures described in Example 363 by employing the appropriately substituted starting materials. The compounds in Table 5 represent those analogues employing an ether oxygen atom as a linking element in the chain between the imidazole group and the trisubstituted nitrogen atom.

TABLE 5

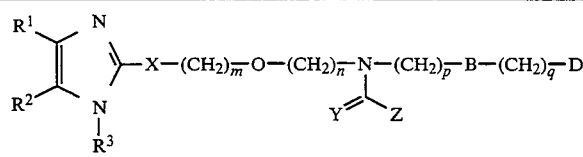

| Example | R$^1$ | R$^2$ | R$^3$ | X | m | n | Y | Z | p | B | q | D | mp |
|---|---|---|---|---|---|---|---|---|---|---|---|---|---|
| 361 | C$_6$H$_5$ | C$_6$H$_5$ | H | S | 2 | 2 | O | NH-2,4-C$_6$H$_3$F$_2$ | 2 | CH$_2$ | 2 | C$_2$H$_5$ | 106–108 |
| 362 | C$_6$H$_5$ | C$_6$H$_5$ | H | S | 2 | 2 | O | NH-i-C$_3$H$_7$ | 2 | CH$_2$ | 2 | C$_2$H$_5$ | 92–93 |
| 363 | 4-CH$_3$OC$_6$H$_4$ | 4-CH$_3$OC$_6$H$_4$ | H | S | 2 | 2 | O | NH-i-C$_3$H$_7$ | 2 | CH$_2$ | 2 | C$_2$H$_5$ | 85–87 |
| 364 | 4-CH$_3$OC$_6$H$_4$ | 4-CH$_3$OC$_6$H$_4$ | H | S | 2 | 2 | O | NH-2,4-C$_6$H$_3$F$_2$ | 2 | CH$_2$ | 2 | C$_2$H$_5$ | 100–102 |
| 365 | 4-CH$_3$SC$_6$H$_4$ | 4-CH$_3$SC$_6$H$_4$ | H | S | 2 | 2 | O | NH-i-C$_3$H$_7$ | 2 | CH$_2$ | 2 | C$_2$H$_5$ | — |
| 366 | 4-(CH$_3$)$_2$NC$_6$H$_4$ | 4-(CH$_3$)$_2$NC$_6$H$_4$ | H | S | 2 | 2 | O | NH-i-C$_3$H$_7$ | 2 | CH$_2$ | 2 | C$_2$H$_5$ | — |
| 367 | 4-CH$_3$OC$_6$H$_4$ | 4-CH$_3$OC$_6$H$_4$ | H | S | 2 | 2 | O | OCH$_2$C$_6$H$_5$ | 2 | CH$_2$ | 2 | C$_2$H$_5$ | — |
| 368 | 4-CH$_3$OC$_6$H$_4$ | 4-CH$_3$OC$_6$H$_4$ | H | S | 3 | 3 | O | NH-i-C$_3$H$_7$ | 2 | CH$_2$ | 2 | C$_2$H$_5$ | — |
| 369 | 4-CH$_3$OC$_6$H$_4$ | 4-CH$_3$OC$_6$H$_4$ | H | S | 2 | 2 | S | NH-i-C$_3$H$_7$ | 2 | CH$_2$ | 2 | C$_2$H$_5$ | — |
| 370 | 4-CH$_3$OC$_6$H$_4$ | 4-CH$_3$OC$_6$H$_4$ | CH$_3$ | NCH$_3$ | 2 | 2 | O | NH-i-C$_3$H$_7$ | 2 | CH$_2$ | 2 | C$_2$H$_5$ | — |
| 371 | C$_6$H$_5$ | C$_6$H$_5$ | H | S | 2 | 2 | O | NH-2,4-C$_6$H$_3$F$_2$ | 4 | S | 1 | H | — |

TABLE 5-continued

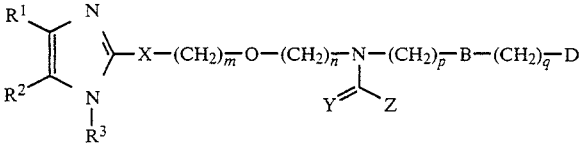

| Example | R[1] | R[2] | R[3] | X | m | n | Y | Z | p | B | q | D | mp |
|---|---|---|---|---|---|---|---|---|---|---|---|---|---|
| 372 | $C_6H_5$ | $C_6H_5$ | H | S | 2 | 2 | O | $NH\text{-}i\text{-}C_3H_7$ | 4 | S | 1 | H | — |
| 373 | $4\text{-}CH_3OC_6H_4$ | $4\text{-}CH_3OC_6H_4$ | H | S | 2 | 2 | O | $NH\text{-}i\text{-}C_3H_7$ | 4 | S | 1 | H | — |
| 374 | $4\text{-}CH_3OC_6H_4$ | $4\text{-}CH_3OC_6H_4$ | H | S | 2 | 2 | O | $NH\text{-}2,4\text{-}C_6H_3F_2$ | 4 | S | 1 | H | — |
| 375 | $4\text{-}CH_3SC_6H_4$ | $4\text{-}CH_3SC_6H_4$ | H | S | 2 | 2 | O | $NH\text{-}i\text{-}C_3H_7$ | 4 | S | 1 | H | — |
| 376 | $4\text{-}(CH_3)_2NC_6H_4$ | $4\text{-}(CH_3)_2NC_6H_4$ | H | S | 2 | 2 | O | $NH\text{-}i\text{-}C_3H_7$ | 4 | S | 1 | H | — |
| 377 | $4\text{-}CH_3OC_6H_4$ | $4\text{-}CH_3OC_6H_4$ | H | S | 2 | 2 | O | $OCH_2C_6H_5$ | 4 | S | 1 | H | — |
| 378 | $4\text{-}CH_3OC_6H_4$ | $4\text{-}CH_3OC_6H_4$ | H | S | 3 | 3 | O | $NH\text{-}i\text{-}C_3H_7$ | 4 | S | 1 | H | — |
| 379 | $4\text{-}CH_3OC_6H_4$ | $4\text{-}CH_3OC_6H_4$ | H | S | 2 | 2 | S | $NH\text{-}i\text{-}C_3H_7$ | 4 | S | 1 | H | — |
| 380 | $4\text{-}CH_3OC_6H_4$ | $4\text{-}CH_3OC_6H_4$ | $CH_3$ | $NCH_3$ | 2 | 2 | O | $NH\text{-}i\text{-}C_3H_7$ | 4 | S | 1 | H | — |
| 381 | $C_6H_5$ | $C_6H_5$ | H | S | 2 | 2 | O | $NH\text{-}2,4\text{-}C_6H_3F_2$ | 1 | $C(=O)\text{-}NCH_3$ | 4 | H | — |
| 382 | $C_6H_5$ | $C_6H_5$ | H | S | 2 | 2 | O | $NH\text{-}i\text{-}C_3H_7$ | 1 | $C(=O)\text{-}NCH_3$ | 4 | H | — |
| 383 | $4\text{-}CH_3OC_6H_4$ | $4\text{-}CH_3OC_6H_4$ | H | S | 2 | 2 | O | $NH\text{-}i\text{-}C_3H_7$ | 1 | $C(=O)\text{-}NCH_3$ | 4 | H | — |
| 384 | $4\text{-}CH_3OC_6H_4$ | $4\text{-}CH_3OC_6H_4$ | H | S | 2 | 2 | O | $NH\text{-}2,4\text{-}C_6H_3F_2$ | 1 | $C(=O)\text{-}NCH_3$ | 4 | H | — |
| 385 | $4\text{-}CH_3SC_6H_4$ | $4\text{-}CH_3SC_6H_4$ | H | S | 2 | 2 | O | $NH\text{-}i\text{-}C_3H_7$ | 1 | $C(=O)\text{-}NCH_3$ | 4 | H | — |
| 386 | $4\text{-}(CH_3)_2NC_6H_4$ | $4\text{-}(CH_3)_2NC_6H_4$ | H | S | 2 | 2 | O | $NH\text{-}i\text{-}C_3H_7$ | 1 | $C(=O)\text{-}NCH_3$ | 4 | H | — |
| 387 | $4\text{-}CH_3OC_6H_4$ | $4\text{-}CH_3OC_6H_4$ | H | S | 2 | 2 | O | $OCH_2C_6H_5$ | 1 | $C(=O)\text{-}NCH_3$ | 4 | H | — |
| 388 | $4\text{-}CH_3OC_6H_4$ | $4\text{-}CH_3OC_6H_4$ | H | S | 3 | 3 | O | $NH\text{-}i\text{-}C_3H_7$ | 1 | $C(=O)\text{-}NCH_3$ | 4 | H | — |
| 389 | $4\text{-}CH_3OC_6H_4$ | $4\text{-}CH_3OC_6H_4$ | H | S | 2 | 2 | S | $NH\text{-}i\text{-}C_3H_7$ | 1 | $C(=O)\text{-}NCH_3$ | 4 | H | — |
| 390 | $4\text{-}CH_3OC_6H_4$ | $4\text{-}CH_3OC_6H_4$ | $CH_3$ | $NCH_3$ | 2 | 2 | O | $NH\text{-}i\text{-}C_3H_7$ | 1 | $C(=O)\text{-}NCH_3$ | 4 | H | — |
| 391 | $C_6H_5$ | $C_6H_5$ | H | S | 2 | 2 | O | $NH\text{-}2,4\text{-}C_6H_3F_2$ | 3 | $OC(=O)$ | 3 | H | — |
| 392 | $C_6H_5$ | $C_6H_5$ | H | S | 2 | 2 | O | $NH\text{-}i\text{-}C_3H_7$ | 3 | $OC(=O)$ | 3 | H | — |
| 393 | $4\text{-}CH_3OC_6H_4$ | $4\text{-}CH_3OC_6H_4$ | H | S | 2 | 2 | O | $NH\text{-}i\text{-}C_3H_7$ | 3 | $OC(=O)$ | 3 | H | — |
| 394 | $4\text{-}CH_3OC_6H_4$ | $4\text{-}CH_3OC_6H_4$ | H | S | 2 | 2 | O | $NH\text{-}2,4\text{-}C_6H_3F_2$ | 3 | $OC(=O)$ | 3 | H | — |
| 395 | $4\text{-}CH_3SC_6H_4$ | $4\text{-}CH_3SC_6H_4$ | H | S | 2 | 2 | O | $NH\text{-}i\text{-}C_3H_7$ | 3 | $OC(=O)$ | 3 | H | — |
| 396 | $4\text{-}(CH_3)_2NC_6H_4$ | $4\text{-}(CH_3)_2NC_6H_4$ | H | S | 2 | 2 | O | $NH\text{-}i\text{-}C_3H_7$ | 3 | $OC(=O)$ | 3 | H | — |
| 397 | $4\text{-}CH_3OC_6H_4$ | $4\text{-}CH_3OC_6H_4$ | H | S | 2 | 2 | O | $OCH_2C_6H_5$ | 3 | $OC(=O)$ | 3 | H | — |
| 398 | $4\text{-}CH_3OC_6H_4$ | $4\text{-}CH_3OC_6H_4$ | H | S | 3 | 3 | O | $NH\text{-}i\text{-}C_3H_7$ | 3 | $OC(=O)$ | 3 | H | — |
| 399 | $4\text{-}CH_3OC_6H_4$ | $4\text{-}CH_3OC_6H_4$ | H | S | 2 | 2 | S | $NH\text{-}i\text{-}C_3H_7$ | 3 | $OC(=O)$ | 3 | H | — |
| 400 | $4\text{-}CH_3OC_6H_4$ | $4\text{-}CH_3OC_6H_4$ | $CH_3$ | $NCH_3$ | 2 | 2 | O | $NH\text{-}i\text{-}C_3H_7$ | 3 | $OC(=O)$ | 3 | H | — |
| 401 | $i\text{-}C_3H_7$ | $4\text{-}CH_3OC_6H_4$ | H | S | 4 | 2 | S | $NHCH_2C_6H_5$ | 2 | $CH_2$ | 2 | $C_2H_5$ | — |
| 402 | $i\text{-}C_3H_7$ | $4\text{-}CH_3OC_6H_4$ | H | S | 4 | 2 | S | $NHCH_2C_6H_5$ | 2 | S | 2 | H | — |
| 403 | $i\text{-}C_3H_7$ | $4\text{-}CH_3OC_6H_4$ | H | S | 4 | 2 | S | $NHCH_2C_6H_5$ | 4 | $C(=O)\text{-}NCH_3$ | 4 | H | — |
| 404 | $i\text{-}C_3H_7$ | $4\text{-}CH_3OC_6H_4$ | H | S | 4 | 2 | S | $NHCH_2C_6H_5$ | 2 | $OC(=O)$ | 2 | H | — |
| 405 | $3\text{-}ClC_6H_4$ | $3\text{-}ClC_6H_4$ | $CH_3$ | $NCH_3$ | 2 | 4 | S | $C_6H_5$ | 2 | $CH_2$ | 2 | $C_2H_5$ | — |
| 406 | $3\text{-}ClC_6H_4$ | $3\text{-}ClC_6H_4$ | $CH_3$ | $NCH_3$ | 2 | 4 | S | $C_6H_5$ | 2 | S | 2 | H | — |
| 407 | $3\text{-}ClC_6H_4$ | $3\text{-}ClC_6H_4$ | $CH_3$ | $NCH_3$ | 2 | 4 | S | $C_6H_5$ | 4 | $C(=O)\text{-}NCH_3$ | 4 | H | — |
| 408 | $3\text{-}ClC_6H_4$ | $3\text{-}ClC_6H_4$ | $CH_3$ | $NCH_3$ | 2 | 4 | S | $C_6H_5$ | 2 | $OC(=O)$ | 2 | H | — |
| 409 | $C_6H_{11}$ | $C_6H_{11}$ | $C_6H_5$ | $CH_2$ | 4 | 4 | S | $NC_6H_5$ | 2 | $CH_2$ | 2 | $C_2H_5$ | — |
| 410 | $C_6H_{11}$ | $C_6H_{11}$ | $C_6H_5$ | $CH_2$ | 4 | 4 | S | $NC_6H_5$ | 2 | S | 2 | H | — |
| 411 | $C_6H_{11}$ | $C_6H_{11}$ | $C_6H_5$ | $CH_2$ | 4 | 4 | S | $NC_6H_5$ | 4 | $C(=O)\text{-}NCH_3$ | 4 | H | — |
| 412 | $C_6H_{11}$ | $C_6H_{11}$ | $C_6H_5$ | $CH_2$ | 4 | 4 | S | $NC_6H_5$ | 2 | $OC(=O)$ | 2 | H | — |
| 413 | 2-furanyl | 2-furanyl | H | S | 3 | 3 | $H_2$ | $CH_2CH(CH_3)_2$ | 2 | $CH_2$ | 2 | $C_2H_5$ | — |
| 414 | 2-furanyl | 2-furanyl | H | S | 3 | 3 | $H_2$ | $CH_2CH(CH_3)_2$ | 2 | S | 2 | H | — |
| 415 | 2-furanyl | 2-furanyl | H | S | 3 | 3 | $H_2$ | $CH_2CH(CH_3)_2$ | 4 | $C(=O)\text{-}NCH_3$ | 4 | H | — |
| 416 | 2-furanyl | 2-furanyl | H | S | 3 | 3 | $H_2$ | $CH_2CH(CH_3)_2$ | 2 | $OC(=O)$ | 2 | H | — |
| 417 | $C_6H_{11}C_2H_4$ | $C_6H_{11}C_2H_4$ | $CH_3$ | $NCH_3$ | 2 | 2 | $H_2$ | $C_7H_{15}$ | 2 | $CH_2$ | 2 | $C_2H_5$ | — |
| 418 | $C_6H_{11}C_2H_4$ | $C_6H_{11}C_2H_4$ | $CH_3$ | $NCH_3$ | 2 | 2 | $H_2$ | $C_7H_{15}$ | 2 | S | 2 | H | — |
| 419 | $C_6H_{11}C_2H_4$ | $C_6H_{11}C_2H_4$ | $CH_3$ | $NCH_3$ | 2 | 2 | $H_2$ | $C_7H_{15}$ | 4 | $C(=O)\text{-}NCH_3$ | 4 | H | — |
| 420 | $C_6H_{11}C_2H_4$ | $C_6H_{11}C_2H_4$ | $CH_3$ | $NCH_3$ | 2 | 2 | $H_2$ | $C_7H_{15}$ | 2 | $OC(=O)$ | 2 | H | — |

EXAMPLE 422

Preparation of
N-[2-[2-(4,5-bis(4-methoxyphenyl)-1H-imidazol-2-ylthio)-acetoxy]-ethyl]-N'-(2,4-difluorophenyl)-N-heptyl-urea Part A A solution of ethanolamine (8.00 mL, 133 mmol) and triethylamine (20.0 mL, 143 mmol) in tetrahydrofuran (200 mL) was cooled to 0° C., and a solution of heptanoyl chloride (20.0 mL, 129 mmol) in tetrahydrofuran (50 mL) was added dropwise over 30 minutes. After stirring an additional 18 hours, the reaction mixture was poured into water (400 mL), and extracted with methylene chloride (2×300 mL). The extracts were combined, dried over anhydrous magnesium sulfate and evaporated to afford the solid product (N-(2-hydroxyethyl)-heptanamide), which was recrystallized to purity from ether-hexane (22.3 g, 129 mmol, 100%), melting point 91°–93° C. 1H NMR (CDCl$_3$): 6.31 (1H, br s); 3.75–3.68 (2H, m); 3.55–3.39 (3H, m); 2.21 (2H, t, J=7.2 Hz); 1.69–1.58 (2H, m); 1.39–1.24 (6H, m); 0.88 (3H, t, J=6.6 Hz).

Part B

A slurry of lithium aluminum hydride (10.35 g, 273 mmol) in anhydrous tetrahydrofuran (100 mL) was cooled to 0° C., and treated dropwise with a solution of the amide prepared in Part A above (16.0 g, 92.1 mmol) in tetrahydrofuran (100 mL) over 1 hour. The solution was then heated to reflux for 20 hours, cooled back to 0° C., and quenched by the careful, sequential addition of water (11 mL), 15% aqueous sodium hydroxide (33 mL), and water (33 mL). This mixture was filtered through a plug of celite with copious tetrahydrofuran washing, and the filtrate was dried over anhydrous potassium carbonate and evaporated. The oil thus obtained (5.49 g, 34.5 mmol, 37%) was sufficiently pure N-heptylethanolamine. 1H NMR (CDCl$_3$): 3.61 (2H, t, J=5.3 Hz); 2.84 (2H, br s); 2.73 (2H, t, J=5.3 Hz); 2.57 (2H, t, J=7.7 Hz); 1.55–1.42 (2H, m); 1.35–1.21 (8H, m); 0.85 (3H, t, J=7.0 Hz).

Part C

The amino alcohol prepared in Part B above (2.80 g, 17.6 mmol) was dissolved in methylene chloride (40 mL), and cooled to 0 C. The solution was treated with neat 2,4-difluorophenylisocyanate (2.10 mL, 17.7 mmol), and stirred for 18 hours. The solution was cooled again to 0° C., and treated with triethylamine (2.70 mL, 19.4 mmol). A solution of chloroacetyl chloride (1.50 mL, 18.8 mmol) in methylene chloride (10 mL) was added dropwise, and the reaction mixture was allowed to stir for an additional 18 hours. After filtration and evaporation of the reaction mixture, the resulting oily residue was purified by elution through a plug of silica gel (1:1 ethyl acetate-hexane) to afford, after evaporation, N-[2-(2-chloroacetoxy)-ethyl]-N'-(2,4-diflourophenyl)-N-heptyl-urea (6.28 g, 16.1 mmol, 91%). 1H NMR (CDCl$_3$): 8.04–7.95 (1H, m); 6.85 (2H, t, J=8.8 Hz); 6.66 (1H, br s); 4.39 (2H, t, J=5.4 Hz); 4.10 (2H, s); 3.65 (2H, t, J=5.4 Hz); 3.33 (2H, t, J=7.7 Hz); 1.71–1.61 (2H, m); 1.38–1.24 (8H, m); 0.89 (3H, t, J 6.6 Hz).

Part D

A solution of the chloride prepared above, 4,5-bis(4-methoxyphenyl)-1H-imidazole-2-thiol (5.24 g, 16.8 mmol), and anhydrous potassium carbonate (3.21 g, 23.2 mmol) in tetrahydrofuran (60 mL) was heated to reflux for 18 hours. The mixture was cooled to 0° C., and poured into water (200 mL). This mixture was extracted with methylene chloride (2×200 mL), and the extracts were combined, dried over anhydrous magnesium sulfate and evaporated. The residual oil was separated by flash chromatography (1:1 ethyl acetate-hexane) to afford the product, N'-[2-[2-(4,5-bis(4-methoxyphenyl)-1H-imidazol-2-ylthio)-acetoxy]-ethyl]-N'-(2,4-difluorophenyl)-N-heptyl-urea, as an amorphous solid. 1H NMR (CDCl$_3$): 7.81 (1H, dt, J=9.2, 5.9 Hz); 7.39 (4H, br d, J=7 Hz); 6.82 (4H, d, J=8.7 Hz); 6.81–6.69 (3H, m); 4.33 (2H, t, J=5.2 Hz); 3.85–3.77 (2H, m); 3.79 (6H, s); 3.74–3.65 (2H, m); 3.65 (2H, m); 3.29 (2H, t, J=7.7 Hz); 1.70–1.59 (2H, m); 1.35–1.25 (8H, m); 0.88 (3H, t, J=7.0 Hz). Elemental analysis: calculated C 63.05, H 6.05, N 8.40; found C 63.15, H 5.97, N 8.14.

Compounds 421–480 in Table 6 were prepared or could be prepared analogously by the procedures described in Example 422 by employing the appropriately substituted starting materials. The compounds in Table 6 represent those analogues employing a carboxylic ester or amide as a linking element in the chain between the imidazole group and the trisubstituted nitrogen atom.

TABLE 6

$$\begin{array}{c}R^1\\R^2\end{array}\!\!\!\!\!\!\!\!\!\!\!\!\!\!\!\!\begin{array}{c}N\\\\N\\|\\R^3\end{array}\!\!\!\!\!\!\!\!\!\!\!-X-(CH_2)_{\overline{m}}A-(CH_2)_{\overline{n}}N-(CH_2)_{\overline{p}}B-(CH_2)_{\overline{q}}D$$

$$\begin{array}{c}Y\!\!\diagup\!\!\diagdown\!\! Z\end{array}$$

| Ex. | R$^1$ | R$^2$ | R$^3$ | X | m | A | n | Y | Z | p | B | q | D | mp |
|---|---|---|---|---|---|---|---|---|---|---|---|---|---|---|
| 421 | C$_6$H$_5$ | C$_6$H$_5$ | H | S | 1 | C(=O)O | 2 | O | NH-2,4-C$_6$H$_3$F$_2$ | 1 | CH$_2$ | 1 | H | 67–69 |
| 422 | 4-CH$_3$OC$_6$H$_4$ | 4-CH$_3$OC$_6$H$_4$ | H | S | 1 | C(=O)O | 2 | O | NH-2,4-C$_6$H$_3$F$_2$ | 2 | CH$_2$ | 2 | C$_2$H$_5$ | oil$^a$ |
| 423 | 4-(CH$_3$)$_2$NC$_6$H$_4$ | 4-(CH$_3$)$_2$NC$_6$H$_4$ | H | S | 1 | C(=O)O | 2 | O | NH-i-C$_3$H$_7$ | 2 | CH$_2$ | 2 | C$_2$H$_5$ | — |
| 424 | C$_6$H$_5$ | C$_6$H$_5$ | H | S | 1 | C(=O)O | 2 | O | NH-i-C$_3$H$_7$ | 2 | O | 2 | C$_2$H$_5$ | — |
| 425 | C$_6$H$_5$ | C$_6$H$_5$ | H | S | 1 | C(=O)O | 2 | O | NH-i-C$_3$H$_7$ | 2 | O | 2 | OCH$_3$ | — |
| 426 | C$_6$H$_5$ | C$_6$H$_5$ | H | S | 1 | C(=O)O | 2 | O | NH-i-C$_3$H$_7$ | 2 | O | 2 | OH | — |
| 427 | C$_6$H$_5$ | C$_6$H$_5$ | H | S | 1 | C(=O)O | 2 | O | NH-i-C$_3$H$_7$ | 2 | NCH$_3$ | 2 | C$_2$H$_5$ | — |
| 428 | C$_6$H$_5$ | C$_6$H$_5$ | CH$_3$ | SO$_2$ | 1 | C(=O)O | 2 | H$_2$ | C$_2$H$_5$ | 3 | O | 3 | OCH$_3$ | — |
| 429 | C$_6$H$_5$ | C$_6$H$_5$ | H | S | 1 | C(=O)O | 2 | O | NH-i-C$_3$H$_7$ | 2 | S | 2 | C$_2$H$_5$ | — |
| 430 | C$_6$H$_5$ | C$_6$H$_5$ | H | SO$_2$ | 1 | C(=O)O | 2 | O | NH-i-C$_3$H$_7$ | 2 | SO$_2$ | 2 | C$_2$H$_5$ | — |
| 431 | C$_6$H$_5$ | C$_6$H$_5$ | H | S | 1 | C(=O)NH | 2 | O | NH-2,4-C$_6$H$_3$F$_2$ | 1 | CH$_2$ | 1 | H | — |
| 432 | 4-CH$_3$OC$_6$H$_4$ | 4-CH$_3$OC$_6$H$_4$ | H | S | 1 | C(=O)NH | 2 | O | NH-2,4-C$_6$H$_3$F$_2$ | 2 | CH$_2$ | 2 | C$_2$H$_5$ | 66–70 |
| 433 | 4-(CH$_3$)$_2$NC$_6$H$_4$ | 4-(CH$_3$)$_2$NC$_6$H$_4$ | H | S | 1 | C(=O)NH | 2 | O | NH-i-C$_3$H$_7$ | 2 | CH$_2$ | 2 | C$_2$H$_5$ | — |
| 434 | C$_6$H$_5$ | C$_6$H$_5$ | H | S | 1 | C(=O)NH | 2 | O | NH-i-C$_3$H$_7$ | 2 | O | 2 | C$_2$H$_5$ | — |
| 435 | C$_6$H$_5$ | C$_6$H$_5$ | H | S | 1 | C(=O)NH | 2 | O | NH-i-C$_3$H$_7$ | 2 | O | 2 | OCH$_3$ | — |
| 436 | C$_6$H$_5$ | C$_6$H$_5$ | H | S | 1 | C(=O)NH | 2 | O | NH-i-C$_3$H$_7$ | 2 | O | 2 | OH | — |

TABLE 6-continued $$R^1, R^2 \text{ substituted pyrimidine} - X-(CH_2)_{\overline{m}}A-(CH_2)_{\overline{n}}N-(CH_2)_{\overline{p}}B-(CH_2)_{\overline{q}}D$$ with $Y=Z$ group on N, and $R^3$ on ring N

| Ex. | R¹ | R² | R³ | X | m | A | n | Y | Z | p | B | q | D | mp |
|---|---|---|---|---|---|---|---|---|---|---|---|---|---|---|
| 437 | C₆H₅ | C₆H₅ | H | S | 1 | C(=O)NH | 2 | O | NH-i-C₃H₇ | 2 | NCH₃ | 2 | C₂H₅ | — |
| 438 | C₆H₅ | C₆H₅ | CH₃ | SO₂ | 1 | C(=O)NH | 2 | H₂ | C₂H₅ | 3 | O | 3 | OCH₃ | — |
| 439 | C₆H₅ | C₆H₅ | H | S | 1 | C(=O)NH | 2 | O | NH-i-C₃H₇ | 2 | S | 2 | C₂H₅ | — |
| 440 | C₆H₅ | C₆H₅ | H | SO₂ | 1 | C(=O)NH | 2 | O | NH-i-C₃H₇ | 2 | SO₂ | 2 | C₂H₅ | — |
| 441 | C₆H₅ | C₆H₅ | H | S | 2 | OC(=O) | 1 | O | NH-2,4-C₆H₃F₂ | 1 | CH₂ | 1 | H | — |
| 442 | 4-CH₃OC₆H₄ | 4-CH₃OC₆H₄ | H | S | 2 | OC(=O) | 1 | O | NH-2,4-C₆H₃F₂ | 2 | CH₂ | 2 | C₂H₅ | — |
| 443 | 4-(CH₃)₂NC₆H₄ | 4-(CH₃)₂NC₆H₄ | H | S | 2 | OC(=O) | 1 | O | NH-i-C₃H₇ | 2 | CH₂ | 2 | C₂H₅ | — |
| 444 | C₆H₅ | C₆H₅ | H | S | 2 | OC(=O) | 1 | O | NH-i-C₃H₇ | 2 | O | 2 | C₂H₅ | — |
| 445 | C₆H₅ | C₆H₅ | H | S | 2 | OC(=O) | 1 | O | NH-i-C₃H₇ | 2 | O | 2 | OCH₃ | — |
| 446 | C₆H₅ | C₆H₅ | H | S | 2 | OC(=O) | 1 | O | NH-i-C₃H₇ | 2 | O | 2 | OH | — |
| 447 | C₆H₅ | C₆H₅ | H | S | 2 | OC(=O) | 1 | O | NH-i-C₃H₇ | 2 | NCH₃ | 2 | C₂H₅ | — |
| 448 | C₆H₅ | C₆H₅ | CH₃ | SO₂ | 2 | OC(=O) | 1 | H₂ | C₂H₅ | 3 | O | 3 | OCH₃ | — |
| 449 | C₆H₅ | C₆H₅ | H | S | 2 | OC(=O) | 1 | O | NH-i-C₃H₇ | 2 | S | 2 | C₂H₅ | — |
| 450 | C₆H₅ | C₆H₅ | H | SO₂ | 2 | OC(=O) | 1 | O | NH-i-C₃H₇ | 2 | SO₂ | 2 | C₂H₅ | — |
| 451 | C₆H₅ | C₆H₅ | H | S | 2 | NHC(=O) | 1 | O | NH-2,4-C₆H₃F₂ | 1 | CH₂ | 1 | H | — |
| 452 | 4-CH₃OC₆H₄ | 4-CH₃OC₆H₄ | H | S | 2 | NHC(=O) | 1 | O | NH-2,4-C₆H₃F₂ | 2 | CH₂ | 2 | C₂H₅ | — |
| 453 | 4-(CH₃)₂NC₆H₄ | 4-(CH₃)₂NC₆H₄ | H | S | 2 | NHC(=O) | 1 | O | NH-i-C₃H₇ | 2 | CH₂ | 2 | C₂H₅ | — |
| 454 | C₆H₅ | C₆H₅ | H | S | 2 | NHC(=O) | 1 | O | NH-i-C₃H₇ | 2 | O | 2 | C₂H₅ | — |
| 455 | C₆H₅ | C₆H₅ | H | S | 2 | NHC(=O) | 1 | O | NH-i-C₃H₇ | 2 | O | 2 | OCH₃ | — |
| 456 | C₆H₅ | C₆H₅ | H | S | 2 | NHC(=O) | 1 | O | NH-i-C₃H₇ | 2 | O | 2 | OH | — |
| 457 | C₆H₅ | C₆H₅ | H | S | 2 | NHC(=O) | 1 | O | NH-i-C₃H₇ | 2 | NCH₃ | 2 | C₂H₅ | — |
| 458 | C₆H₅ | C₆H₅ | CH₃ | SO₂ | 2 | NHC(=O) | 1 | H₂ | C₂H₅ | 3 | O | 3 | OCH₃ | — |
| 459 | C₆H₅ | C₆H₅ | H | S | 2 | NHC(=O) | 1 | O | NH-i-C₃H₇ | 2 | S | 2 | C₂H₅ | — |
| 460 | C₆H₅ | C₆H₅ | H | SO₂ | 2 | NHC(=O) | 1 | O | NH-i-C₃H₇ | 2 | SO₂ | 2 | C₂H₅ | — |
| 461 | i-C₃H₇ | 4-CH₃OC₆H₄ | H | S | 4 | C(=O)O | 2 | S | NHCH₂C₆H₅ | 2 | C₂H₅ | 2 | H | — |
| 462 | i-C₃H₇ | 4-CH₃OC₆H₄ | H | S | 4 | C(=O)NH | 2 | S | NHCH₂C₆H₅ | 2 | CH₃ | 4 | H | — |
| 463 | i-C₃H₇ | 4-CH₃OC₆H₄ | H | S | 4 | OC(=O) | 2 | S | NHCH₂C₆H₅ | 4 | CH₃ | 2 | NHC₆H₅ | — |
| 464 | i-C₃H₇ | 4-CH₃OC₆H₄ | H | S | 4 | NHC(=O) | 2 | S | NHCH₂C₆H₅ | 2 | CH₃ | 2 | OCH₃ | — |
| 465 | 3-ClC₆H₄ | 3-ClC₆H₄ | CH₃ | NCH₃ | 2 | C(=O)O | 4 | S | C₆H₅ | 2 | C₂H₅ | 2 | H | — |
| 466 | 3-ClC₆H₄ | 3-ClC₆H₄ | CH₃ | NCH₃ | 2 | C(=O)NH | 4 | S | C₆H₅ | 2 | CH₃ | 4 | H | — |
| 467 | 3-ClC₆H₄ | 3-ClC₆H₄ | CH₃ | NCH₃ | 2 | OC(=O) | 4 | S | C₆H₅ | 4 | CH₃ | 2 | NHC₆H₅ | — |
| 468 | 3-ClC₆H₄ | 3-ClC₆H₄ | CH₃ | NCH₃ | 2 | NHC(=O) | 4 | S | C₆H₅ | 2 | CH₃ | 2 | OCH₃ | — |
| 469 | C₆H₁₁ | C₆H₁₁ | C₆H₅ | CH₂ | 4 | C(=O)O | 4 | S | NC₆H₅ | 2 | C₂H₅ | 2 | H | — |
| 470 | C₆H₁₁ | C₆H₁₁ | C₆H₅ | CH₂ | 4 | C(=O)NH | 4 | S | NC₆H₅ | 2 | CH₃ | 4 | H | — |
| 471 | C₆H₁₁ | C₆H₁₁ | C₆H₅ | CH₂ | 4 | OC(=O) | 4 | S | NC₆H₅ | 4 | CH₃ | 2 | NHC₆H₅ | — |
| 472 | C₆H₁₁ | C₆H₁₁ | C₆H₅ | CH₂ | 4 | NHC(=O) | 4 | S | NC₆H₅ | 2 | CH₃ | 2 | OCH₃ | — |
| 473 | 2-furanyl | 2-furanyl | H | S | 3 | C(=O)O | 3 | H₂ | CH₂CH(CH₃)₂ | 2 | C₂H₅ | 2 | H | — |
| 474 | 2-furanyl | 2-furanyl | H | S | 3 | C(=O)NH | 3 | H₂ | CH₂CH(CH₃)₂ | 2 | CH₃ | 4 | H | — |
| 475 | 2-furanyl | 2-furanyl | H | S | 3 | OC(=O) | 3 | H₂ | CH₂CH(CH₃)₂ | 4 | CH₃ | 2 | NHC₆H₅ | — |
| 476 | 2-furanyl | 2-furanyl | H | S | 3 | NHC(=O) | 3 | H₂ | CH₂CH(CH₃)₂ | 2 | CH₃ | 2 | OCH₃ | — |
| 477 | C₆H₁₁C₂H₄ | C₆H₁₁C₂H₄ | CH₃ | NCH₃ | 2 | C(=O)O | 2 | H₂ | C₇H₁₅ | 2 | C₂H₅ | 2 | H | — |
| 478 | C₆H₁₁C₂H₄ | C₆H₁₁C₂H₄ | CH₃ | NCH₂ | 2 | C(=O)NH | 2 | H₂ | C₇H₁₅ | 2 | CH₃ | 4 | H | — |
| 479 | C₆H₁₁C₂H₄ | C₆H₁₁C₂H₄ | CH₃ | NCH₃ | 2 | OC(=O) | 2 | H₂ | C₇H₁₅ | 4 | CH₃ | 2 | NHC₆H₅ | — |
| 480 | C₆H₁₁C₂H₄ | C₆H₁₁C₂H₄ | CH₃ | NCH₃ | 2 | NHC(=O) | 2 | H₂ | C₇H₁₅ | 2 | CH₃ | 2 | OCH₃ | — |

Footnotes to Table 6
*a*¹H NMR(CDCl₃): 7.81(1H, dt, J=9.2, 5.9Hz); 7.39(4H, br d, J=7Hz); 6.82(4H, d, J=8.7Hz); 6.81–6.69(3H, m); 4.33(2H, t, J=5.2Hz); 3.85–3.77(2H, m); 3.79(6H, s); 3.74–3.65(2H, m); 3.65(2H, m); 3.29(2H, t, J=7.7Hz); 1.70–1.59(2H, m); 1.35–1.25(8H, m); 0.88(3H, t, J=7.0Hz).

Utility

The comopunds of the invetion are effective antiatherosclerotic agents that act in a variety of ways. The compounds may be inhibitors of the enzyme acyl CoA:-cholesterol acyl transferase (ACAT). Inhibition of ACAT has a variety of antiatherosclerotic effects, including inhibiting esterification and transport of chloesterol across the intestinal wall. In addition, by inhibiting cholesterol ester formation, the compounds may be useful in preventing the formation of cholesterol ester rich macrophages (foam cells) in the arterial wall. Foam cells are a source of the large quantity of cholesterol ester found in atheromatous lesions, as compared to the surrounding undiseased tissue. Other compounds of the invention may be inhibitors of cholesterol biosynthesis in the liver. Some compounds of the invention are both ACAT inhibitors and inhibitors of cholesterol biosynthesis.

A. Assay of the Inhibition of Acyl-CoA: Cholesterol Acyltransferase (ACAT) in Hepatic Microsomes The ability of the compounds to inhibit ACAT, the enzyme responsible for the intracellular synthesis of cholesteryl esters, was tested as follows. Male Sprague Dawley rats weighing 150–300 g, were fed rat chow ad libitum. The animals were fasted for twenty-four hours prior to being sacrificed by decapitation. The livers were perfused in situ with 50 ml of cold 0.25M sucrose, excised, and homogenized in three volumes of 0.1M phosphate buffer, pH 7.4, that contained 0.5 mM EDTA (ethylenediaminetetraacetic acid), 1.0 mM glutathione, 0.25M sucrose and 20 mM leupeptin. Microsomes were obtained by differential centrifugation; the supernatant from an initial spin at 15,000×g for 15 minutes was centrifuged at 105,000×g for 1 hour to pellet the microsomes. The microsomes were suspended in homogenization buffer, reisolated by centrifugation, and stored at −70° C. Microsomes were used within one month of preparation.

The control assay in a final volume of 200 μl consisted of 200 μg of microsomal protein, 75μ<$^{14}$C-oleoyl-CoA (10,000 dpm/nmol) in 0.1M phosphate, pH 7.4, that contained 1 mM glutathione. Compounds were added in 5 μl of DMSO (dimethyl sulfoxide) and additional controls were run with DMSO only. All components, except the oleoyl-CoA, were preincubated for 15 min. at 37° C. prior to the initiation of the reaction by the addition of oleoyl-CoA. The assay was terminated after 10 min. by the addition of 4 ml of chloroform:methanol (2:1, v/v). 20,000 dpm of 3H-choledsteryl oleate and 10 μg of unlabeled cholesteryl oleate and oleic acid were added as an internal standard and carriers, respectively. After allowing 10 min. for lipid extraction, 0.8 ml of deionized water was added to separte the solution into two phases. The lower chloroform phase was collected, dried under nitrogen and resuspended in 2 ml of hexane:diethyl ether (97:3 v/v). The lipids were then loaded onto BAKERSBOND spe* silica gel columns. Extracts were collected in scintillation vials and counted for radioactivity. The specific activity of ACAT in the control incubation averaged 260 pmol/min/mg microsomal protein. The inhibition of ACAT activity by the compounds is shown in Table 7; the data are expressed as the concentration at which ACAT activity is inhibited by 50% ($IC_{50}$).

B. Assays of the Inhibition of Cholesterol Esterification in Mammalian Cells

The esterification of cholesterol was determined in the murine macrophage-like cell line J774.A1. Cells were seeded in 35 mm wells at a density of 300,000 cells per well in 2 mls of Dulbecco's Eagle Medium (DMEM) supplemented with 10% fetal bovine serum (FBS). Cells were incubated at 37° C. in an atmosphere of 5% $CO_2$ and 93% humidity. After 234 hours the media was changed to 0.68 mls 10% FBS-DMEM containing 34 μg of acetylated human low density lipoprotein (ac-LDL) to increase the intracellular concentration of cholesterol and promote esterification. At 41 hours, various inhibitors were added to the cells in DMSO (10 μl/ml maximum). At 43 hours, the cells were pulsed with 0.1 mM $^{14}$C-oleic acid (10,000 dpm/nmol) complexed with BSA (bovine serum albumin) to follow cholesterol ester formation. The experiment was terminated at 45 hours by washing the monolayers 3 times with 3 ml of Tris-buffered saline at 4° C. The lipids were extracted by incubating the monolayers with 1.5 ml of hexane: isopropanol (3:2, v/v) for 30 min. under gentle agitation. During this period, 10,000 dpm $^3$H-cholesterol oleate and 10 μg of unlabeled cholesteryl oleate, oleic acid, triolein and cholesterol were added as an intgernal standard and carriers. The organic solvent was removed and the cells were washed with an additional 1.0 ml of hexane: isopropanol which was combined with the original extract. The cells were allowed to dry overnight, digested with 2.0 ml of 0.2N sodium hydroxide for 1 hour and an aliquot of the solubilized protein used for protein determination using the Lowry method. The organic extract was taken to dryness, then resuspended in 2 ml of hexane:diethyl ether (97:3, v/v) and loaded onto BAKERSBOND spe* silica gel columns. Extracts were collected in scintillation vials to determine the amount of radioactivity. The conversion of oleic acid to cholesteryl ester in the control averaged 0.54 mmol/hour/mg protein and was increased upon the addition of ac-LDL to about 10.689±0.69 mmol/hour/mg protein. The inhibition of esterification by the compounds is shown in Table 8; the data are expressed as the concentration at which ACAT activity is inhibited by 50% ($IC_{50}$).

TABLE 7

Inhibition of In Vitro Hepatic ACAT Activity by Various Compounds

| Compound of Example No. | Inhibition of Cholesterol Esterification ($IC_{50}$, μM) |
| --- | --- |
| 1 | 0.66 |
| 2 | 0.08 |
| 32 | 1.50 |
| 101 | 0.17 |
| 102 | 0.26 |
| 161 | 0.066 |
| 162 | 0.27 |
| 181 | 0.24 |
| 183 | 0.35 |
| 261 | 0.07 |
| 262 | 0.19 |
| 281 | 0.04 |
| 282 | 0.09 |
| 283 | 0.23 |
| 284 | 0.48 |
| 303 | 0.34 |
| 304 | 0.50 |
| 321 | 0.05 |
| 322 | 0.03 |
| 325 | 0.28 |
| 361 | 0.08 |
| 362 | 0.19 |
| 363 | 0.85 |
| 364 | 2.30 |
| 421 | 4.10 |
| 422 | 2.60 |
| 432 | 3.75 |

TABLE 8

Inhibition of Cholesterol Esterification in Macrophage by Various Compounds

| Compound of Example No. | Inhibition of Cholesterol Esterification ($IC_{50}$, μM) |
| --- | --- |
| 1 | 0.58 |
| 2 | 2.18 |
| 32 | 0.63 |
| 101 | 1.47 |
| 102 | 2.40 |
| 161 | 0.88 |
| 162 | 1.34 |
| 181 | 2.74 |
| 183 | 6.28 |
| 261 | 1.75 |
| 262 | 0.84 |
| 281 | 6.74 |
| 282 | 6.84 |
| 283 | 0.84 |
| 284 | 2.42 |
| 303 | 0.25 |
| 304 | 0.36 |
| 321 | 4.01 |
| 322 | 3.02 |
| 325 | 0.041 |
| 361 | 3.98 |
| 362 | 0.99 |
| 364 | 0.50 |
| 421 | 3.68 |
| 422 | 2.39 |
| 432 | 0.80 |

Dosage Forms:

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspension. The active ingredient can be administered alone, but is generally administered with a pharmaceutical carrier. A valuable treatise with respect to pharmaceutical dosage forms is *Remington's Pharmaceutical Sciences*, 16th Edition, 1980.

In their therapeutic use as antihypercholesterolemic and/or antiatherosclerotic agents, the compounds of the invention are administered to the patient at dosage levels of 1 to 28 g per day. For a normal male adult human of approximately 70 kg of body weight, this translates into a dosage of 14 to 400 mg per kilogram body weight per day. The dosage administered will, of course, vary depending upon known factors such as the age, health, and weight of the recipient; nature and extent of symptoms, kind of concurrent treatment, frequency of treatment, and the effect desired. Useful pharmaceutical dosage forms for administration of the compounds of this invention can be illustrated as follows:

Tablets

Tablets are prepared by conventional procedures so that the dosage unit is 500 milligrams of active ingredient, 150 milligrams of lactose, 50 milligrams of cellulose and 10 milligrams of magnesium stearate.

Capsules

Capsules are prepared by conventional procedures so that the dosage unit is 500 milligrams of active ingredient, 100 milligrams of cellulose and 10 milligrams of magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |

| -continued | |
|---|---|
| Resuspendable Powder | |
| | Wt. % |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogeneous paste.

The term "consisting essentially of" in the present disclosure is intended to have its customary meaning, namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited publications and applications may provide further useful information, however, these cited materials are hereby incorporated by reference.

What is claimed is:

1. A compound of the formula (I):

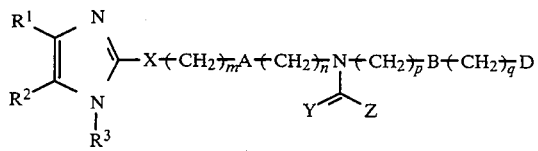

wherein
A is selected from the group O, or —C(=O)O—;
B is selected from the group —CH$_2$, —O—, NR$^6$ or —S(O)$_r$;
D is selected from the group

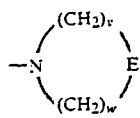

wherein
E is =CH$_2$=, O, =NR$^7$, =C=O, —C(=O)NR$^7$—, or —C(=O)O—, and v and w are independently 0–4, with the proviso that v and w cannot both be 0;
X is S(O)$_r$, or —CH$_2$, where r is 0–2;
Y is O or, H$_2$;
Z is NHR$^4$, OR$^4$ or R$^4$;
R$^1$ and R$^2$ are selected independently from phenyl unsubstituted or substituted with 1 to 3 groups selected from F, C$_1$–C$_4$ alkoxy, C$_1$–C$_4$ alkyl, C$_3$–C$_8$ branched alkyl, CH$_3$S(O)$_r$, or NR$^7$R$^8$;
R$^3$ is —H, —CH$_3$ or phenyl;
R$^4$ is C$_1$–C$_8$ alkyl, C$_3$–C$_8$ branched alkyl, C$_3$–C$_7$ cycloalkyl, C$_4$–C$_{10}$ cycloalkylalkyl, C$_7$–C$_{14}$ aralkyl, phenyl unsubstituted or substituted with 1 to 3 groups selected from C$_1$–C$_4$ alkyl, C$_3$–C$_8$ branched alkyl, F, C$_1$–C$_4$ alkoxy, or —CN, benzyl unsubstituted or substituted with 1 to 3 groups selected from —CH$_3$, —CH$_3$O, —F, or —CN, pyridyl, pyrrolyl, pyrimidyl, or imidazolyl;
R$^5$ is H, CH$_3$, or phenyl;
R$^6$, R$^7$ and R$^8$ are selected independently from H or C$_1$–C$_4$ alkyl;
n, p and q are independently 0–4; and m is 1 or 2;
or a pharmaceutically acceptable salt thereof.

2. A compound of the formula (I):

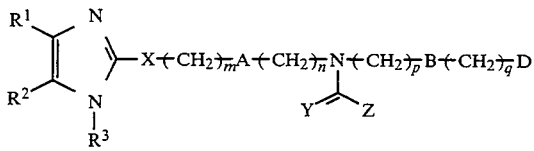

wherein
A is O, or —C(=O)O—;
B is —NR$^6$, —S(O)r where r is 0–2 or —N(R$^6$)C(=O)—;
D is

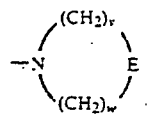

wherein

E is O, and v and w are each 2;
X is S(O)$_r$, or CH$_2$, where r is 0–2;
Y is O, S, H$_2$ or NR$_5$;
Z is NHR$^4$, OR$^4$ or R$^4$;
R$^1$ and R$^2$ are selected independently from phenyl unsubstituted or substituted with 1 to 3 groups selected from F, Cl, Br, OH, C$_1$–C$_4$ alkoxy, C$_1$–C$_4$ alkyl, C$_3$–C$_8$ branched alkyl, CH$_3$S(O)$_r$, NO$_2$, CF$_3$, or NR$^7$R$^8$;
R$^3$ is H;
R$^4$ is C$_1$–C$_8$ alkyl, C$_3$–C$_8$ branched alkyl, or C$_3$–C$_7$ cycloalkyl;
R$^5$ is H or CH$_3$;
R$^6$ is H or C$_1$–C$_8$ alkyl;
n, p and q are 0–4; and
m is 1 or 2.

3. A compound of claim 1 wherein:
R$^1$ and R$^2$ are selected independently from H or phenyl unsubstituted or substituted with 1 to 3 groups selected from CH$_3$O, CH$_3$S(O)$_r$ or (CH$_3$)$_2$N);
R$^4$ is C$_1$–C$_8$ alkyl, C$_3$–C$_8$ branched alkyl, or phenyl unsubstituted or substituted with 1 to 3 groups selected from CH$_3$, CH(CH$_3$)$_2$, F, CH$_3$O, or CN);
Z is NHR$^4$ or R$^4$; and
m, n and p are 2.

4. The compound which is N'-(2,4-difluorophenyl)-N-[5-(4,5-diphenyl-1H-imidazol-2-ylthio)pentyl]-N-[2-(4-morpholinyl)ethyl]-urea.

5. A pharmaceutical composition comprising an effective ACAT inhibiting amount or antihypercholesterolemic amount or antiatherosclerotic amount of a compound of claim 1 and a pharmaceutically acceptable carrier.

6. A pharmaceutical composition comprising an effective ACAT inhibiting amount or antihypercholesterolemic amount or antiatherosclerotic amount of a compound of claim 2 and a pharmaceutically acceptable carrier.

7. A pharmaceutical composition comprising an effective ACAT inhibiting amount or antihypercholesterolemic amount or antiatherosclerotic amount of a compound of claim 3 and a pharmaceutically acceptable carrier.

8. A pharmaceutical composition comprising an effective ACAT inhibiting amount or antihypercholesterolemic amount or antiatherosclerotic amount of a compound of claim 4 and a pharmaceutically acceptable carrier.

9. A method of treating hypercholesterolemia or atherosclerosis in a mammal comprising administering to the mammal a therapeutically effective amount of a compound of claim 1.

10. A method of treating hypercholesterolemia or atherosclerosis in a mammal comprising administering to the mammal a therapeutically effective amount of a compound of claim 2.

11. A method of treating hypercholesterolemia or atherosclerosis in a mammal comprising administering to the mammal a therapeutically effective amount of a compound of claim 3.

12. A method of treating hypercholesterolemia or atherosclerosis in a mammal comprising administering to the mammal a therapeutically effective amount of a compound of claim 4.

* * * * *